(12) United States Patent
Sivan et al.

(10) Patent No.: US 8,354,066 B2
(45) Date of Patent: *Jan. 15, 2013

(54) ARTIFICIAL RECEPTORS

(75) Inventors: Uri Sivan, Haifa (IL); Yoram Reiter, Haifa (IL); Arbel Artzy-Schnirman, Haifa (IL)

(73) Assignee: Technion Research & Development Foundation Ltd., Haifa (IL)

( * ) Notice: Subject to any disclaimer, the term of this patent is extended or adjusted under 35 U.S.C. 154(b) by 523 days.

This patent is subject to a terminal disclaimer.

(21) Appl. No.: 12/311,216

(22) PCT Filed: Sep. 20, 2007

(86) PCT No.: PCT/IL2007/001159
§ 371 (c)(1),
(2), (4) Date: Aug. 10, 2009

(87) PCT Pub. No.: WO2008/035343
PCT Pub. Date: Mar. 27, 2008

(65) Prior Publication Data
US 2009/0306578 A1 Dec. 10, 2009

Related U.S. Application Data

(63) Continuation-in-part of application No. 11/524,264, filed on Sep. 21, 2006.

(51) Int. Cl.
*B01J 19/12* (2006.01)
*C07K 16/00* (2006.01)
(52) U.S. Cl. ............................. 422/186.04; 530/387.9
(58) Field of Classification Search ............. 422/185.04; 530/387.9
See application file for complete search history.

(56) References Cited

U.S. PATENT DOCUMENTS

| | | | |
|---|---|---|---|
| 5,639,505 | A | 6/1997 | Kossovsky et al. |
| 5,716,854 | A | 2/1998 | Löfås et al. |
| 5,728,532 | A | 3/1998 | Ackley |
| 6,325,904 | B1 | 12/2001 | Peeters |
| 6,342,347 | B1 | 1/2002 | Bauer |
| 6,824,974 | B2 | 11/2004 | Pisharody et al. |
| 6,870,234 | B2 | 3/2005 | Brewer et al. |
| 2001/0053535 | A1 | 12/2001 | Bashir et al. |
| 2002/0028440 | A1 | 3/2002 | Willner et al. |
| 2008/0076670 | A1 | 3/2008 | Sivan et al. |

FOREIGN PATENT DOCUMENTS

| | | |
|---|---|---|
| WO | WO 98/00107 | 1/1998 |
| WO | WO 99/66322 | 12/1999 |
| WO | WO 01/02858 | 1/2001 |
| WO | WO 02/13785 | 2/2002 |
| WO | WO 03/021268 | 3/2003 |
| WO | WO 2004/067191 | 8/2004 |
| WO | WO 2005/090981 | 9/2005 |
| WO | WO 2008/035343 | 3/2008 |

OTHER PUBLICATIONS

Office Action Dated Oct. 28, 2010 From the Israeli Patent Office Re.: Application No. 178266 and Its Translation Into English.
Communication Pursuant to Article 94(3) EPC Dated Jan. 27, 2011 From the European Patent Office Re.: Application No. 05718906.0.
Examiner's Report Dated Mar. 24, 2010 From the Australian Government, IP Australia Re.: Application No. 2006220422.
Response Dated Mar. 10, 2010 to Communication Pursuant to Article 94(3) EPC of Sep. 16, 2009 From the European Patent Office Re.: Application No. 05718906.0.
Response Dated May 19, 2011 to Communication Pursuant to Article 94(3) EPC of Jan. 27, 2011 From the European Patent Office Re.: Application No. 05718906.0.
Official Action Dated Jun. 14, 2011 From the US Patent and Trademark Office Re.: U.S. Appl. No. 11/524,264.
Hodneland et al. "Biomolecular Surfaces That Release Ligands Under Electrochemical Control", Journal of the American Chemical Society, 122: 4235-4236, 2000.
Response Dated Sep. 20, 2010 to Official Action of Mar. 18, 2010 From the US Patent and Trademark Office Re.: U.S. Appl. No. 11/524,264.
Response Dated Oct. 11, 2011 to Official Action of Jun. 14, 2011 From the US Patent and Trademark Office Re.: U.S. Appl. No. 11/524,264.
Communication Pursuant to Article 94(3) EPC Dated Sep. 16, 2009 From the European Patent Office Re.: Application No. 05718906.0.
Communication Relating to the Results of the Partial International Search Dated May 26, 2008 From the International Searching Authority Re.: Application No. PCT/IL2007/001159.
International Preliminary Report on Patentability Dated Apr. 2, 2009 From the International Bureau of WIPO Re.: Application No. PCT/IL2007/001159.
International Preliminary Report on Patentability Dated Oct. 5, 2006 From the International Bureau of WIPO Re.: Application No. PCT/IL2005/000333.
International Search Report Dated Sep. 7, 2005 From the International Searching Authority Re.: Application No. PCT/IL2005/000333.
International Search Report Dated Sep. 23, 2008 From the International Searching Authority Re.: Application No. PCT/IL2007/001159.
Office Action Dated Jun. 18, 2009 From the Israeli Patent Office Re.: Application No. 178266 and Its Translation Into English.
Official Action Dated Aug. 12, 2009 From the US Patent and Trademark Office Re.: U.S. Appl. No. 11/524,264.
Official Action Dated Feb. 20, 2009 From the US Patent and Trademark Office Re.: U.S. Appl. No. 11/524,264.
Response Dated Dec. 7, 2009 to Office Action of Jun. 18, 2009 From the Israel Patent Office Re.: Application No. 178266.
Response Dated Dec. 11, 2009 to Official Action of Aug. 12, 2009 From the US Patent and Trademark Office Re.: U.S. Appl. No. 11/524,264.
Response Dated Dec. 14, 2009 to Official Action of Aug. 12, 2009 From the US Patent and Trademark Office Re.: U.S. Appl. No. 11/524,264.

(Continued)

*Primary Examiner* — Lynn Bristol

(57) ABSTRACT

Antibodies are provided. For as example, an antibody capable of binding an artificial receptor which comprises a hydroquinone monolayer and is incapable of binding the artificial receptor when comprising a benzoquinone monolayer. Also provided are methods and systems using same for control delivery of a molecule-of-interest into a tissue.

13 Claims, 13 Drawing Sheets
(11 of 13 Drawing Sheet(s) Filed in Color)

OTHER PUBLICATIONS

Written Opinion Dated Sep. 7, 2005 From the International Searching Authority Re.: Application No. PCT/IL2005/000333.
Written Opinion Dated Sep. 23, 2008 From the International Searching Authority Re.: Application No. PCT/IL2007/001159.
Caruso et al. "DNA Binding and Hybridization on gold and Derivatized Surfaces", Sensors and Actuators B, 41(1-3): 189-197, 1997.
Estrela et al. "Electrical Detection of Biomolecular Interactions With Metal-Insulator-Semiconductor Diodes", Biosensors and Bioelectronics, 20(8): 15801586, 2005.
Goede et al. "Binding Specificity of a Peptide on Semiconductor Surfaces", Nano Letters, 4(11): 2115-2120, 2004.
Krajevski et al. "Albumin Adhesion on Some Biological and Non-Biological Glasses and Connection With Their Z-Potentials ", Biomaterials, 17(1): 53-60, Jan. 1996. Abstract.
Rombach et al. "Detection of Benzoquinone Adducts to Rat Liver Protein Sulfhydryl Groups Using Specific Antibodies", Chemical Research in Toxicology, XP002474765, 10(12): 1407-1411, Dec. 1997. p. 1409, r-h Col.
Shastri et al. "Biomedical Applications of Electroactive Polymers", Electrical and Optical Polymer Systems, XP000874992, p. 1031-1051, Jan. 1, 1998.
Whaley et al. "Selection of Peptides With Semiconductor Binding Specificity for Directed Nanocrystal Assembly", Nature, 405: 665-668, 2000.
Official Action Dated Mar. 18, 2010 From the US Patent and Trademark Office Re.: U.S. Appl. No. 11/524,264.
Official Action Dated Mar. 7, 2012 From the US Patent and Trademark Office Re.: U.S. Appl. No. 11/524,264.

b | Cleave wafer c | magnified view of cleaved edge a - Grow alternating layers of AB d | magnified view of cleaved edge after coated with glass and holes etched in the glass

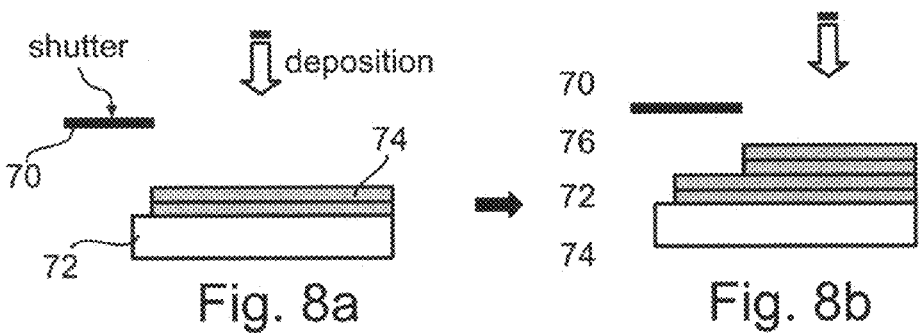
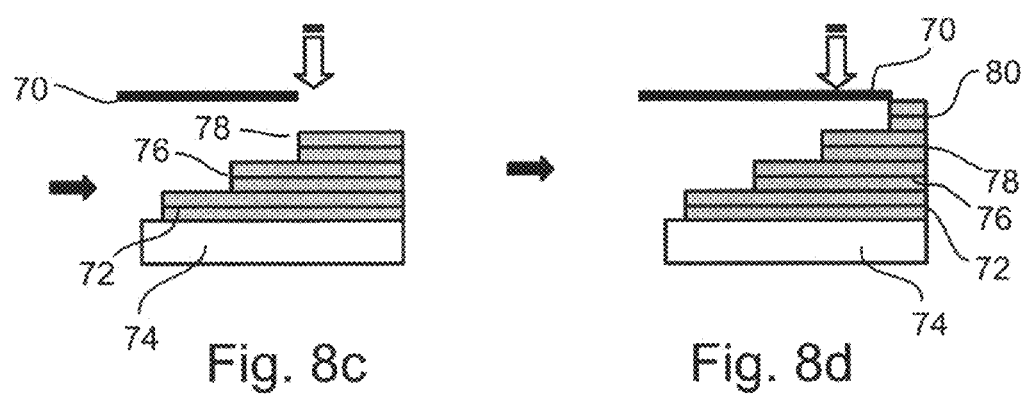
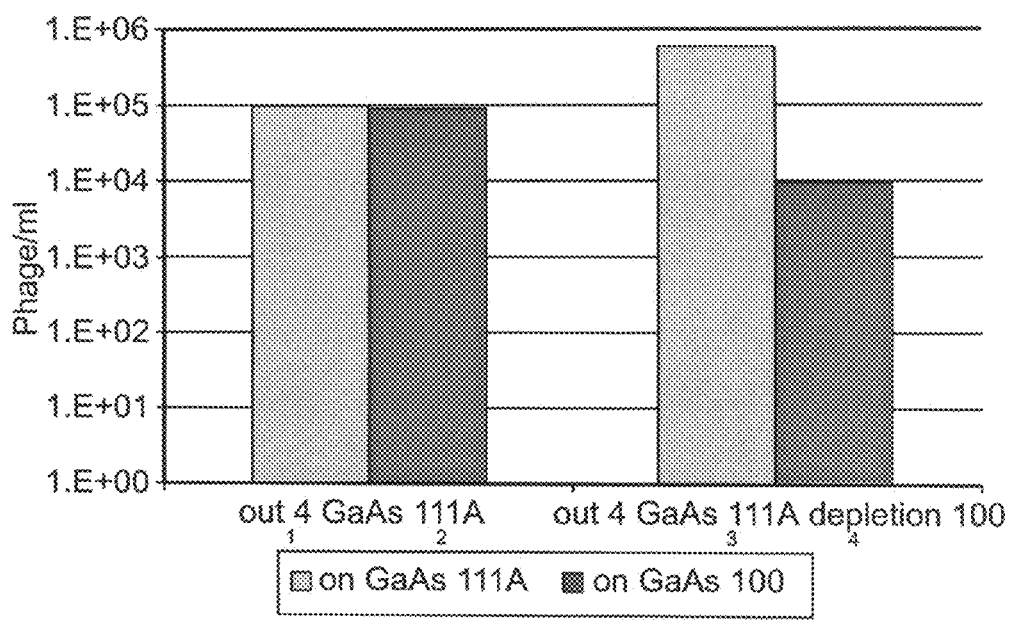

ARTIFICIAL RECEPTORS

RELATED APPLICATIONS

This Application is a National Phase of PCT Patent Application No. PCT/IL2007/001159 having International filing date of Sep. 20, 2007, which is a continuation-in-part of U.S. patent application Ser. No. 11/524,264 filed on Sep. 21, 2006. The contents of the above Applications are all incorporated herein by reference.

FIELD AND BACKGROUND OF THE INVENTION

The invention relates to an artificial receptor capable of binding specific biological moieties, and more particularly, to methods of using same for typing ligands, determining binding domains in proteins, targeted delivery and release of drug molecules, and gaining electrical control over biological processes.

Electrostatic interactions underlie the basis of various biological processes involving the recognition and binding of macromolecules such as DNA, RNA, proteins and carbohydrates to each other. For example, alien macromolecules are identified through molecular recognition between an antibody molecule and the intruding molecule, generally denoted antigen. Likewise, ligands such as hormones bind to their cellular receptors and thus activate cellular responses.

The mammalian immune system offers a vast repertoire of antibody molecules capable of binding selectively an immense number of molecules presented to the body by invading pathogens such as bacteria, viruses, and parasites. Albeit the fact that this repertoire evolved to target mostly bio-molecules, it may potentially contain selective binders to other targets or be expanded to include such binders. Indeed, injection of cholesterol and 1,4-dinitrobenzen (Perl-Treves, D., et al., 1996; Bromberg, R., et al., 1998) microscopic crystals as well as $C_{60}$ conjugated to bovine thyroglobulin to mice (Braden, B. C. et al. 2000) have resulted in generation of antibodies against these materials by the immune system of the injected animal.

Characterization of the domain structures involved in protein-protein interactions such as those between ligands and receptors or antibodies and antigens is crucial for gaining control over such biological processes. Such a characterization can be performed using site directed mutagenesis, in which targeted mutations are introduced into DNA sequences encoding specific proteins (e.g., a receptor) and the effect of the mutation is tested in vitro following the expression of the mutated DNA in suitable cells in the presence of a test molecule (e.g., a labeled ligand). Another approach for characterizing binding domain in a protein is crystallography of a purified protein in the presence of a labeled ligand. Such experiments often results in determination of the amino acids involved in binding the ligand. However, while the first approach is limited by the specific mutations introduced, the latter approach is relatively expensive due to the need of substantial purification steps of the protein of interest.

Most drug molecules are administered using oral or intravenous administration which often result in various unwanted side effects. Such effects result from the interaction of the drug molecule with tissues or organs not intended to be treated by the drug. To overcome such limitations, various targeted drug delivery approaches were developed. These include, viral infection, temperature-sensitive liposome formulations (Viglianti B L, et al., Magn Reson Med. 2004, 51: 1153-62), magnetoliposomes (Kullberg M. et al., Med. Hypotheses. 2005, 64: 468-70), ultrasound-mediated microbubbles (Tsutsui J M, et al., Cardiovasc Ultrasound. 2004, 2: 23) and the like.

There is thus a widely recognized need for, and it would be highly advantageous to have, methods of gaining control over biological processes, characterizing domain structures for protein-protein interactions and efficient targeted drug delivery devoid of the above limitations.

SUMMARY OF THE INVENTION

According to one aspect of the invention there is provided an antibody comprising an antigen binding domain which comprises complementarity determining regions (CDRs) as set forth by SEQ ID NOs:99-104.

According to another aspect of the invention there is provided an antibody comprising an antigen binding domain which comprises complementarity determining regions (CDRs) as set forth by SEQ ID NOs:87-92.

According to yet another aspect of the invention there is provided an antibody comprising an antigen binding domain which comprises complementarity determining regions (CDRs) as set forth by SEQ ID NOs:42, 52, 11, 22, 32 and 1.

According to a further aspect of the invention there is provided an antibody comprising an antigen binding domain which comprises complementarity determining regions (CDRs) as set forth by SEQ ID NOs:46, 56, 12, 26, 36 and 2.

According to still a further aspect of the invention there is provided an antibody comprising an antigen binding domain which comprises complementarity determining regions (CDRs) as set forth by SEQ ID NOs:48, 58, 13, 28, 38, and 3.

According to still a further aspect of the invention there is provided an antibody comprising an antigen binding domain which comprises complementarity determining regions (CDRs) as set forth by SEQ ID NOs:49, 59, 14, 29, 39, and 4.

According to still a further aspect of the invention there is provided an antibody comprising an antigen binding domain which comprises complementarity determining regions (CDRs) as set forth by SEQ ID NOs:45, 55, 15, 25, 35 and 5.

According to still a further aspect of the invention there is provided an antibody comprising an antigen binding domain which comprises complementarity determining regions (CDRs) as set forth by SEQ ID NOs:44, 54, 16, 24, 34, and 6.

According to still a further aspect of the invention there is provided an antibody comprising an antigen binding domain which comprises complementarity determining regions (CDRs) as set forth by SEQ ID NOs:43, 53, 17, 23, 33, and 7.

According to still a further aspect of the invention there is provided an antibody comprising an antigen binding domain which comprises complementarity determining regions (CDRs) as set forth by SEQ ID NOs:41, 51, 18, 21, 31 and 8.

According to still a further aspect of the invention there is provided an antibody comprising an antigen binding domain which comprises complementarity determining regions (CDRs) as set forth by SEQ ID NOs:47, 57, 19, 27, 37 and 9.

According to still a further aspect of the invention there is provided an antibody comprising an antigen binding domain which comprises complementarity determining regions (CDRs) as set forth by SEQ ID NOs:50, 60, 20, 30, 40 and 10.

According to still a further aspect of the invention there is provided an antibody comprising an antigen binding domain which comprises complementarity determining regions (CDRs) as set forth by SEQ ID NOs:93, 94, 95, 96, 97 and 98.

According to yet another aspect of the invention there is provided a system for controllable delivery of a molecule-of-interest to a tissue comprising: (i) the molecule-of-interest conjugated to the antibody of the invention, and; (ii) an artificial receptor which comprises a surface having an extent, the surface comprises a hydroquinone and a switching functionality for controllably modifying unique electrical properties of the surface; wherein the antigen binding domain of the antibody is capable of binding the surface.

According to still another aspect of the invention there is provided a method of controlling a delivery of a molecule-of-interest to a tissue of a subject, comprising: (a) contacting the tissue with the system of the invention in the subject, and; (b) modifying the unique electrical properties of the surface to thereby control a binding or a release of the antibody from the artificial receptor; thereby controlling the delivery of the molecule-of-interest to the tissue.

According to further features in the embodiments of the invention described below, the molecule-of-interest is selected from the group consisting of a drug, a toxin and a detectable moiety.

According to still further features in the described embodiments the system configured for implantation in a subject in need thereof.

According to still further features in the described embodiments modifying is effected using a remote switching unit.

According to still further features in the described embodiments hydroquinone comprises a hydroquinone monolayer.

According to still further features in the described embodiments surface further comprises gold, and whereas the hydroquinone is attached to the surface by conjugating to the gold.

According to still further features in the described embodiments modification of the unique electrical properties of the surface results in a conformation change of the hydroquinone to a benzoquinone and whereas the antibody is incapable of binding the surface following the modification.

According to still further features in the described embodiments the switching functionality is obtained by carbon nanotubes and/or silicone nanowires.

According to still further features in the described embodiments the artificial receptor further comprises a laminate including a plurality of independently electrifiable layers, the surface being formed from a cross-section of the laminate such that the independently electrifiable layers form respective ones of the regions.

According to still further features in the described embodiments the switching functionality comprises a selector for selecting a voltage level for each of the independently electrifiable layers, to thereby allow the electrical field to be varied to provide specific binding of the antigen binding domain.

According to an additional aspect of the invention there is provided an artificial receptor comprising: a surface having an extent, the surface at least partly comprising regions from the group consisting of a metal region and a region comprising metallic particles; the surface having unique surface electrical properties that vary over the extent, the electrical properties being such as to configure an electrical field about the surface to provide specific binding for a target moiety.

According to yet an additional aspect of the invention there is provided an artificial receptor comprising: a surface having an extent, the surface having configurable surface electrical properties that vary over the extent, the configurable electrical properties being such as to configure an electrical field about the surface to provide specific binding for a target moiety.

According to still an additional aspect of the invention there is provided an artificial receptor comprising: a surface having an extent, the surface having unique surface electrical properties that vary over the extent, the variable electrical properties being such as to configure an electrical field about the surface to provide specific binding for a target moiety, the surface comprising at least one substance attached thereto, the at least one substance being capable of modifying at least one of a redox state and molecular conformation.

According to a further aspect of the invention there is provided an artificial receptor comprising: a surface having an extent, the surface having unique surface electrical properties that vary over the extent, the variable electrical properties being such as to configure an electrical field about the surface to provide specific binding for a target moiety, the surface comprising at least one substance attached thereto, the at least one substance being capable of modifying at least one of a hydrophobic property, charged state, hydrophilic property, redox state, molecular conformation and the electrical property of the surface.

According to yet a further aspect of the invention there is provided an artificial receptor comprising: a surface having an extent, the surface having unique surface electrical properties that vary over the extent, the electrical properties being such as to configure an electrical field about the surface to provide specific binding for a target moiety, and wherein the surface comprising a piezoelectric substance attached thereto, and configurable to alter a local electrical field, thereby to alter the unique surface electrical properties.

According to yet a further aspect of the invention there is provided an artificial receptor comprising: a superlattice comprising a surface having an extent, the surface having unique surface electrical properties that vary over the extent, the electrical properties being such as to configure an electrical field about the surface to provide specific binding for a target moiety, and wherein the superlattice is a metal-insulator superlattice comprising metal and insulative layers.

According to yet a further aspect of the invention there is provided an artificial receptor comprising: a surface having an extent, the surface having unique surface electrical properties that vary over the extent, the electrical properties being such as to configure an electrical field about the surface to provide specific binding for a target moiety, and wherein the surface comprises switching functionality for controllably allowing changes to the unique surface electrical properties.

According to yet a further aspect of the invention there is provided an artificial receptor comprising: a surface having an extent, the surface having a unique surface electrical properties that vary over the extent, the electrical properties being such as to configure an electrical field about the surface to provide specific binding for a target moiety.

According to yet a further aspect of the invention there is provided an artificial receptor comprising: a structure having a plurality of layers and a surface having an extent, the surface being in a plane substantially cross-sectional to the plurality of layers, and at least some of the layers being independently electrifiable, such as to produce an electrical field of predetermined form about the surface.

According to yet a further aspect of the invention there is provided an artificial receptor comprising: a surface having an extent, the surface comprising switchable electrical conductive tracks, the conductive tracks being switchable to configure an electrical field about the surface to provide specific binding for a target moiety.

According to still a further aspect of the invention there is provided an array comprising a plurality of addressable locations each including an artificial receptor configured capable of a unique surface electrical property enabling the artificial receptor to specifically bind a ligand.

According to still a further aspect of the invention there is provided a kit for typing ligands comprising an artificial receptor configured capable of a unique surface electrical property enabling to specifically bind a ligand and reagents for qualifying binding of the ligands to the plurality of artificial receptors.

According to still a further aspect of the invention there is provided a method of identifying a small molecule capable of mimicking a binding function of a ligand, the method comprising: (a) exposing the ligand to at least one electrode configured capable of a unique surface electrical property enabling a specific binding of the ligand thereto, thereby identifying at least one electrode capable of specifically binding the ligand; and (b) identifying a small molecule of a plurality of small molecules capable of binding the at least one electrode being identified as capable of specifically binding the ligand, the small molecule being capable of mimicking the binding function of the ligand.

According to still a further aspect of the invention there is provided a method of isolating a specific ligand from a mixed population of ligands, the method comprising exposing the mixed population of ligands to at least one electrode configured capable of a unique surface electrical property enabling a specific binding of a ligand thereto, thereby isolating the specific ligand from the mixed population of ligands.

According to still a further aspect of the invention there is provided a device for controllable delivery of a drug molecule to a tissue comprising a device body including at least one electrode configured capable of a unique surface electrical property enabling a specific binding of a ligand thereto; the ligand being attached to the drug, the unique surface electrical property capable of being modified by a switching unit to control a binding or a release of the ligand and thereby controllably deliver the drug molecule to the tissue.

According to still a further aspect of the invention there is provided a method of controlling a delivery of a drug molecule to a tissue of a subject, comprising: (a) contacting the tissue with a device body including at least one electrode configured capable of a unique surface electrical property enabling a specific binding of a ligand thereto, the ligand being attached to the drug; (b) modifying the unique surface electrical property to thereby control a binding or a release of the ligand and thereby controllably deliver the drug molecule to the tissue.

According to still a further aspect of the invention there is provided an artificial receptor comprising: a structure having a plurality of semiconductor nanocrystals, the nanocrystals comprising P—N junctions, and a surface, the crystals extending over the surface, and at least some of the nanocrystals being independently electrifiable, such as to produce an electrical field of predetermined form about the surface.

According to still a further aspect of the invention there is provided a method of activating or suppressing a biological pathway in cells of a subject, the method comprising: (a) contacting the cells with a device body including at least one electrode configured capable of a unique surface electrical property enabling a specific binding of a ligand thereto, the ligand being capable of activating or suppressing the biological pathway; (b) modifying the unique surface electrical property to thereby control a binding or a release of the ligand and thereby controllably activating or suppressing the biological pathway in the cells of the subject.

According to still a further aspect of the invention there is provided a method of activating or suppressing a biological pathway in cells of a subject, the method comprising: (a) contacting the cells with a device body including at least one electrode configured capable of a unique surface electrical property enabling a specific binding of the antibody thereto, the antibody or a molecule-of-interest attached thereto being capable of activating or suppressing the biological pathway; (b) modifying the unique surface electrical property to thereby control a binding or a release of the antibody and thereby controllably activating or suppressing the biological pathway in the cells of the subject.

According to further features in preferred embodiments of the invention described below, the artificial receptor further comprising a structure having a plurality of layers, wherein the surface being in a plane substantially cross-sectional to the plurality of layers, and at least some of the layers being independently electrifiable, such as to produce an electrical field of predetermined form about the surface.

According to still further features in the described preferred embodiments the surface further comprises zero dimension, one dimension, two dimensions and/or three dimensions.

According to still further features in the described preferred embodiments the at least one substance comprises a molecular monolayer.

According to still further features in the described preferred embodiments the insulative layers comprise one member of the group consisting of a metal oxide, a semiconductor and a ceramic.

According to still further features in the described preferred embodiments the switching functionality is obtained by carbon nanotubes and/or silicone nanowires.

According to still further features in the described preferred embodiments the artificial receptor comprising a laminate including a plurality of independently electrifiable layers, the surface being formed from a cross-section of the laminate such that the independently electrifiable layers form respective ones of the regions.

According to still further features in the described preferred embodiments the switching functionality comprises a selector for selecting a voltage level for each of the independently electrifiable layers, thereby to allow the electrical field to be varied to provide specific binding to different targeted biological moieties.

According to still further features in the described preferred embodiments the target moiety is a biological moiety.

According to still further features in the described preferred embodiments the target moiety is a chemical moiety.

According to still further features in the described preferred embodiments the chemical moiety comprises a polymer and/or a small molecule.

According to still further features in the described preferred embodiments the surface further comprises at least one substance attached to the surface, the at least one substance being capable of modifying hydrophobic property, charged state, hydrophilic property, redox state, molecular conformation and/or the electrical property of the surface.

According to still further features in the described preferred embodiments the at least one substance capable of modifying hydrophobic interaction, hydrophilic interaction, hydrogen bonding and van der waals interaction of the surface with the target moiety.

According to still further features in the described preferred embodiments the at least one substance is an organic substance.

According to still further features in the described preferred embodiments the organic substance is selected from the group consisting hydroquinone, rotaxane and ferrocene.

According to still further features in the described preferred embodiments the at least one substance is a biological substance.

According to still further features in the described preferred embodiments the biological substance is a peptide, a protein, a lipid, a carbohydrate and/or a nucleic acid.

According to still further features in the described preferred embodiments the at least one substance is a Ferroelectric substance.

According to still further features in the described preferred embodiments the Ferroelectric substance is PLZT, and/or BaTiO3.

According to still further features in the described preferred embodiments the at least one substance is a Pyroelectric substance.

According to still further features in the described preferred embodiments the Pyroelectric substance is Li—Ta—O3, polyvinylidene fluoride (PVDF), and/or lead Titanate (PT).

According to still further features in the described preferred embodiments the at least one substance is a Piezoelectric substance.

According to still further features in the described preferred embodiments the Piezoelectric substance is PZT.

According to still further features in the described preferred embodiments the surface comprises a plurality of regions over the extent, each region having a predetermined electrostatic field strength.

According to still further features in the described preferred embodiments each of the regions comprises a respective material selected for electrostatic properties thereof.

According to still further features in the described preferred embodiments the respective material is selected from the group consisting of a ceramic and a semiconductor.

According to still further features in the described preferred embodiments the respective material is selected from the group consisting of a Ferroelectric material, a Pyroelectric material, and a Piezoelectric material.

According to still further features in the described preferred embodiments the Ferroelectric material is PLZT and/or BaTiO3.

According to still further features in the described preferred embodiments the Pyroelectric material is Li—Ta—O3, polyvinylidene fluoride (PVDF), and/or lead Titanate (PT).

According to still further features in the described preferred embodiments the Piezoelectric material is PZT.

According to still further features in the described preferred embodiments the regions are on the order of magnitude of nanometer, Angstrom or tens of nanometer.

According to still further features in the described preferred embodiments the regions are in the order of magnitude of five to ten lattice constants.

According to still further features in the described preferred embodiments variable electrical fields are applied to the regions.

According to still further features in the described preferred embodiments the regions comprise crystals or polycrystals placed in between electrodes.

According to still further features in the described preferred embodiments the crystal comprises a high dielectric constant ceramic.

According to still further features in the described preferred embodiments the high dielectric constant ceramic comprises PLZT.

According to still further features in the described preferred embodiments the artificial receptor further comprises a laminate including a plurality of independently electrifiable layers, the surface being formed from a cross-section of the laminate such that the independently electrifiable layers form respective ones of the regions.

According to still further features in the described preferred embodiments the artificial receptor further comprises a selector for selecting a voltage level for each of the independently electrifiable layers, thereby to allow the electrical field to be varied to provide specific binding to different targeted biological moieties.

According to still further features in the described preferred embodiments the surface comprises an electronically controllable hydrophobic coating, thereby to allow controllable hydrophobic properties per independently electrifiable layer.

According to still further features in the described preferred embodiments the artificial receptor further comprises insulating layers between the independently conductive layers.

According to still further features in the described preferred embodiments the artificial receptor further comprises a covering layer located over the laminate.

According to still further features in the described preferred embodiments the covering layer comprises glass.

According to still further features in the described preferred embodiments the covering layer comprises cavitation.

According to still further features in the described preferred embodiments the surface comprises switchable wiring, the wiring being switchable to provide the unique electrical properties.

According to still further features in the described preferred embodiments the wiring is variably switchable, thereby to provide the specific binding to different target biological moieties as desired.

According to still further features in the described preferred embodiments the plurality of layers comprise alternately insulating layers and conductive layers over at least part of the surface.

According to still further features in the described preferred embodiments the artificial receptor further comprises a switching unit for switching the layers such as to configure an electrical field about the surface to provide specific binding for a target moiety.

According to still further features in the described preferred embodiments the artificial receptor further comprises a covering layer over the surface.

According to still further features in the described preferred embodiments the covering layer comprises electrical insulation.

According to still further features in the described preferred embodiments the covering layer comprises cavitation.

According to still further features in the described preferred embodiments the cavitation is substantially at the nanometer or Angstrom scale.

According to still further features in the described preferred embodiments the artificial receptor plurality of layers have a transverse direction and a longitudinal direction at the surface and wherein the surface has a transverse direction and a longitudinal direction and wherein the layers are aligned about the surface such that the layer transverse direction lies along the surface longitudinal direction.

According to still further features in the described preferred embodiments the widths of the layers in the layer transverse direction are substantially at the nanometer or Angstrom scale.

According to still further features in the described preferred embodiments the artificial receptor further comprises a switching control for switching the conductive tracks such as to reconfigure an electrical field about the surface to provide specific binding for a target moiety.

According to still further features in the described preferred embodiments the widths of the conductive tracks are substantially in the nanometer or Angstrom order of magnitude.

According to still further features in the described preferred embodiments the artificial receptor includes at least one electrode selected of a size, shape or makeup enabling the unique surface electrical property.

According to still further features in the described preferred embodiments the least one electrode comprises a non-biological material.

According to still further features in the described preferred embodiments the at least one electrode is selected of a size or shape enabling binding of a biological moiety thereto.

According to still further features in the described preferred embodiments the at least one electrode is a plurality of electrodes whereas a combined surface electrical property of the plurality of electrodes is capable of binding a specific biological moiety.

According to still further features in the described preferred embodiments the at least one electrode includes a non-biological crystal structure having the unique surface electrical property.

According to still further features in the described preferred embodiments the at least one electrode includes a crystal structure having the unique surface electrical property.

According to still further features in the described preferred embodiments the at least one electrode is a semi-conductive electrode.

According to still further features in the described preferred embodiments the at least one electrode is composed of conductive and non-conductive layers.

According to still further features in the described preferred embodiments the array is constructed such that the unique surface electrical property of the electrode is modifiable.

According to still further features in the described preferred embodiments the size of each of the plurality of electrodes is in a nanometer range.

According to still further features in the described preferred embodiments the distance between each of the plurality of electrodes is smaller than 50 nanometer.

According to still further features in the described preferred embodiments the distance between each of the plurality of electrodes is smaller than 20 nanometer.

According to still further features in the described preferred embodiments the biological moiety is selected from the group consisting of a protein, a peptide, a DNA, an RNA, a carbohydrate and a lipid.

According to still further features in the described preferred embodiments the at least one electrode is a plurality of electrodes whereas a combined surface electrical property of the plurality of electrodes is capable of binding the ligand thereto.

According to still further features in the described preferred embodiments each of the plurality of electrodes is selected of a size or shape enabling binding of the ligand thereto.

According to still further features in the described preferred embodiments the combined surface electrical property of the plurality of electrodes is capable of binding the ligand thereto.

According to still further features in the described preferred embodiments the plurality of electrodes includes a non-biological crystal structure having the unique surface electrical property.

According to still further features in the described preferred embodiments each of the plurality of electrodes includes a crystal structure having the unique surface electrical property.

According to still further features in the described preferred embodiments each of the plurality of electrodes is a semi-conductive electrode.

According to still further features in the described preferred embodiments each of the plurality of electrodes is composed of conductive and non-conductive layers.

According to still further features in the described preferred embodiments each of the plurality of electrodes is constructed such that the unique surface electrical property of each electrode is modifiable.

According to still further features in the described preferred embodiments the size of each of the plurality of electrodes is in a nanometer range.

According to still further features in the described preferred embodiments the ligand is selected from the group consisting of a protein, a peptide, a DNA, an RNA, a carbohydrate and a lipid.

According to still further features in the described preferred embodiments the at least one electrode is selected of a size or shape enabling binding of the ligand thereto.

According to still further features in the described preferred embodiments the at least one electrode is constructed such that the unique surface electrical property is modifiable.

According to still further features in the described preferred embodiments the size of the at least one electrode is in a nanometer range.

According to still further features in the described preferred embodiments the ligand is selected from a phage display antibody library.

According to still further features in the described preferred embodiments the small molecule is a peptide and/or a peptide mimetic.

According to still further features in the described preferred embodiments the ligand is a biological moiety selected from the group consisting of a protein, a peptide, a DNA, an RNA, a carbohydrate and a lipid.

According to still further features in the described preferred embodiments modifying is effected using a remote switching unit.

According to still further features in the described preferred embodiments the method further comprises administering the drug molecule to the subject.

According to still further features in the described preferred embodiments the method further comprises administering the ligand to the subject.

According to still further features in the described preferred embodiments administering is effected by intravenous administration and/or oral administration.

According to still further features in the described preferred embodiments the semiconductor nanocrystals are remotely electrifiable via incident radiation.

According to still further features in the described preferred embodiments the artificial receptor further comprises a substance storage and release mechanism associated with the surface, such that a given change in the electric field is operable to affect the storage and release mechanism to effect release of a substance stored therein.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
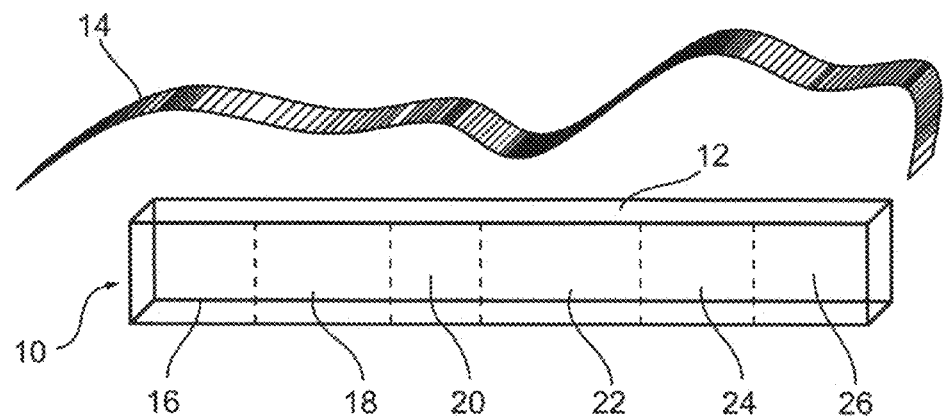
Figure 2B:
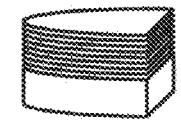
Figure 2C:
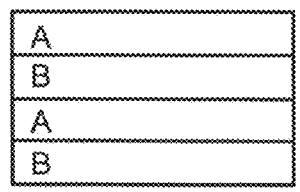
Figure 2A:
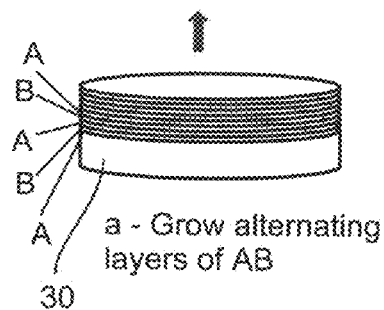
Figure 2D:
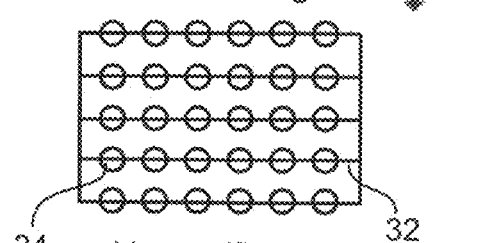
Figure 3:
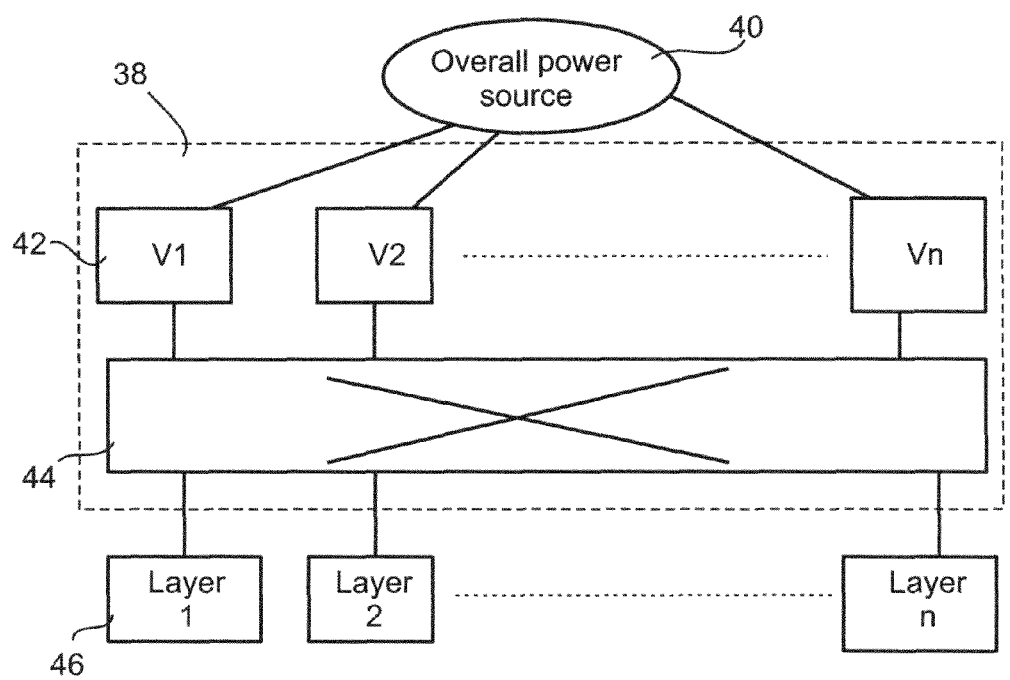
Figure 4:
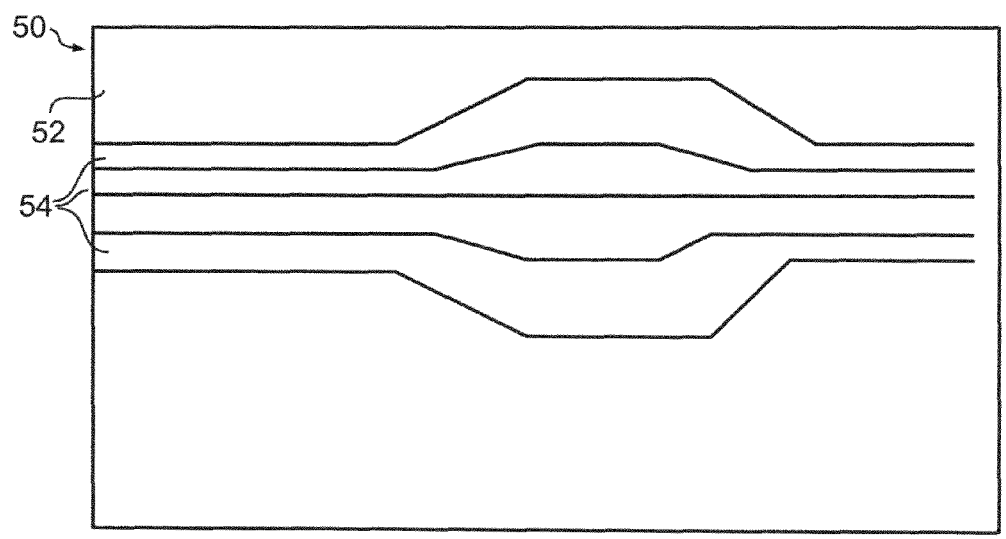
Figure 5:
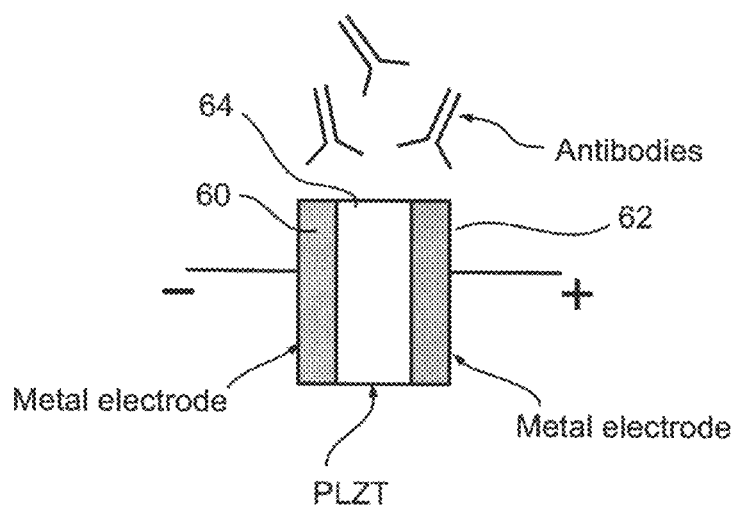
Figure 6:
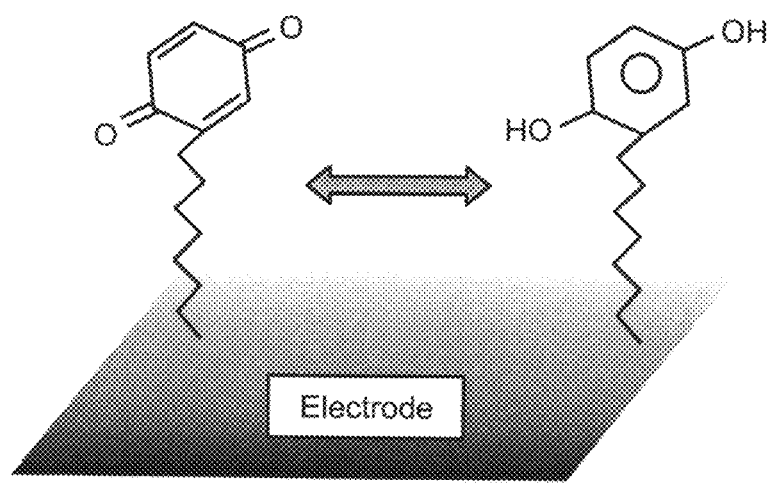
Figure 7:
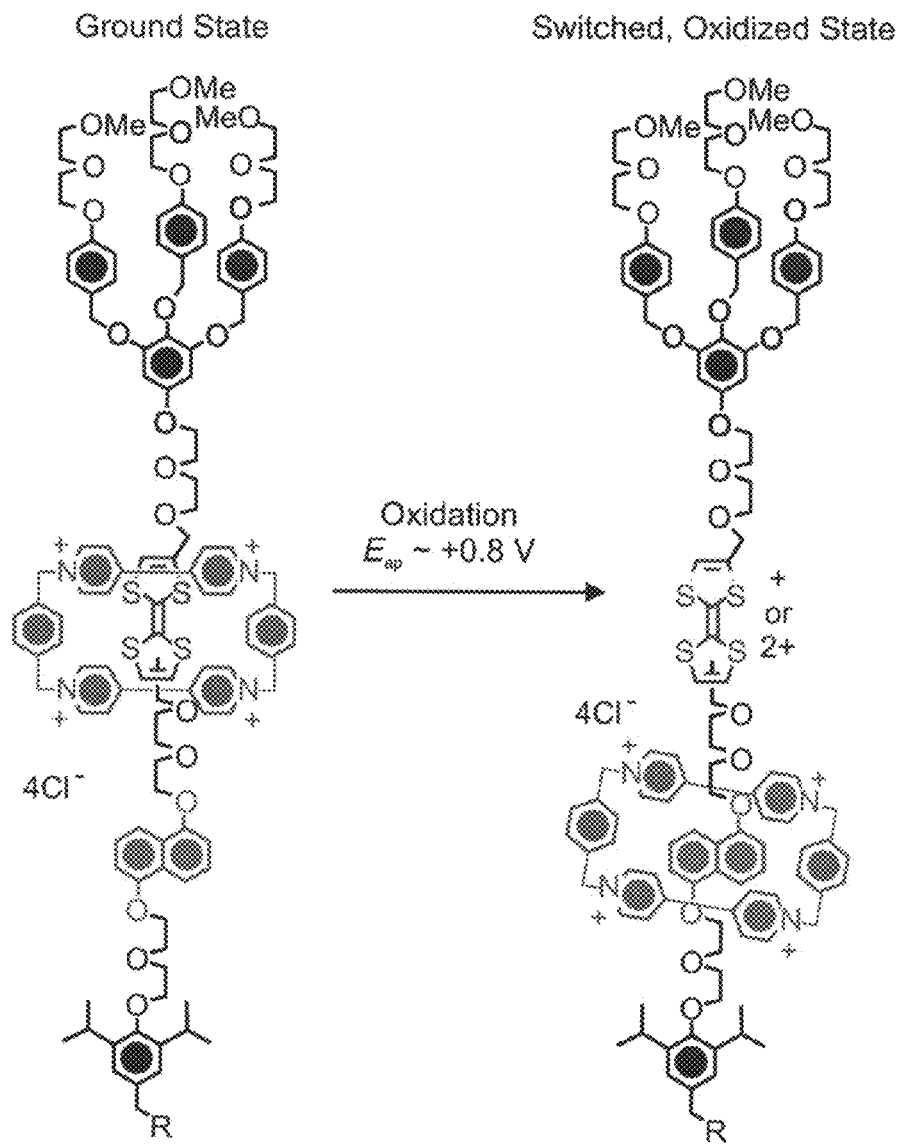

FIG. 1 is a schematic illustration of a specific artificial receptor device according to a first preferred embodiment of the invention; a device 10 is set up with a surface 12 and an electric field about that surface. An isoelectric contour 14 illustrates a possible shape for the electrostatic potential. The surface includes a plurality of regions (16-26), each having a predetermined electrostatic field strength determined, e.g. by the voltage applied to it;

FIGS. 2*a-d* are schematic illustrations showing the construction of a programmable artificial receptor device according to a second preferred embodiment of the invention. FIG. 2*a* illustrates growing of alternating layers of conducting (A) and insulating (B) materials, e.g., GaAs/AlGaAs or metal/metal oxide. FIG. 2*b* illustrates cleaving of the wafer. FIG. 2*c* illustrates the cleaved surface comprises alternating strips with atomically sharp interfaces. FIG. 2*d* shows the cleaved edge coated with glass and holes being etched in the glass, just on top of the A/B interfaces;

FIG. 3 is a simplified diagram showing a preferred switching arrangement for switching the layers of the device of FIGS. 2*a-d* to provide different voltage levels at the layers and a variable overall electrical field at the surface. Device or selector 38 allows selecting the voltage levels for each of the independently electrifiable layers. Power source 40 (may be a battery or a main fed power supply) supplies a series of voltage regulated power sources 42.1 . . . 42.*n*, each set at different voltage levels. A switching matrix 44 then connects any one of the layers 46.1 . . . 46.*n* to any one of the regulated power sources;

FIG. 4 is a simplified diagram showing a programmable artificial receptor device according to a third preferred embodiment of the invention. Device 50 comprises a conventional semiconductor wafer surface 52 on which are patterned conductive tracks 54 using conventional semiconductor manufacturing techniques. The conductive tracks are switched using transistors in the conventional manner;

FIG. 5 is a schematic illustration of an artificial receptor based on a PLZT ferroelectric ceramics. The ceramics (64) is held between to two electrodes (60 and 62) and the application of field by the electrodes on the ceramics changes its unit cell structure. Antibodies selected against either unit cell structure bind to one configuration and do not bind the other configuration;

FIG. 6 is a schematic illustration depicting the effect of application of an electric field on the molecular structure of Hydroquinone. Under a certain electric field the hydroquinone molecule looses two hydrogen (H) molecules and a double bond (=) with oxygen (O) is formed;

FIG. 7 is a schematic illustration depicting the effect of application of an electric field on the molecular structure of Rotaxane; Under a certain electric field the mobile molecular ring translocates into a different position in the molecule (James R. Heath, 2005, J. AM. CHEM. SOC., 127, 1563-1575).

FIGS. 8*a-d* are a sequence of schematic illustrations showing successive stages in the manufacture of electrode layers to enable each layer to have a separate electrical contact. Note the receding shutter whose purpose is to leave exposed conducting segments of the conducting layers for later electrical contact;

FIG. 9 is a histogram depicting the density of recovered binders to GaAs (111A) after three panning cycles. Depletion was performed at the second and third rounds of panning by exposing the phage display library to the GaAs (100) surface prior to exposing the same phages to the GaAs (111A) surface. The number of phages bound to each surface following the fourth round of panning is presented. Columns 1 and 2 correspond to binding to GaAs (111A) (column 1) or GaAs (100) (column 2) after selection on GaAs (111A) without depletion. Columns 3 and 4 correspond to binding to GaAs (111A) (column 3) or GaAs (100) (column 4) after selection on GaAs (111A) with depletion on GaAs (100). Note the specific enrichment (by almost two orders of magnitudes) of scFv phage binders to GaAs (111A) following a selection process which included two depletion cycles on GaAs (100).

Figure 10:
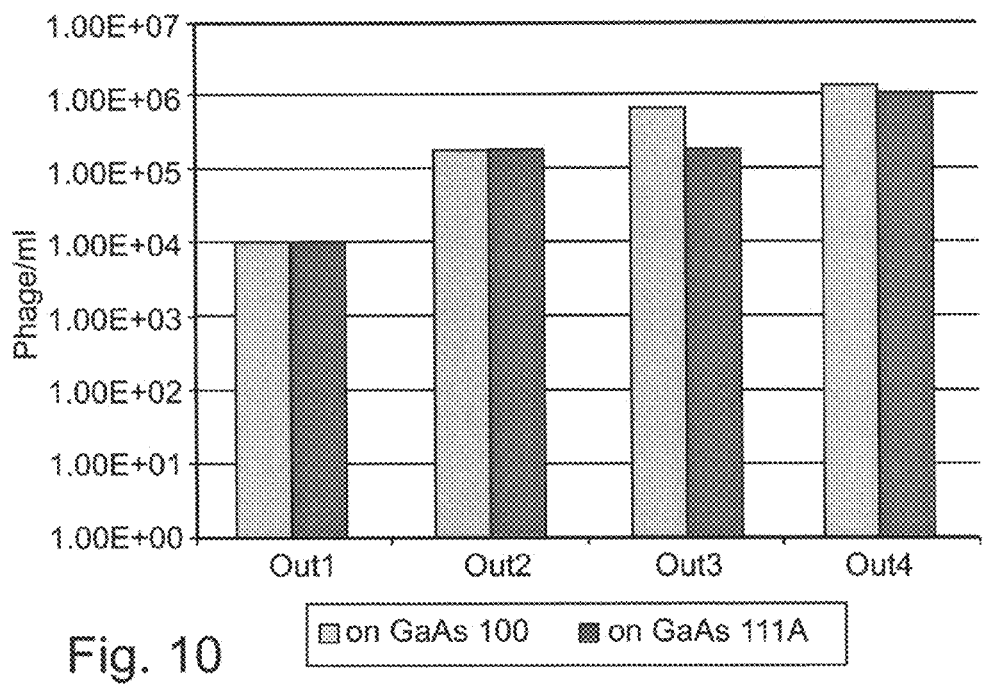

FIG. 10 is a bar graph depicting the enrichment of peptide binders to GaAs (100) and GaAs (111A) surfaces following each panning round.

Figure 11:
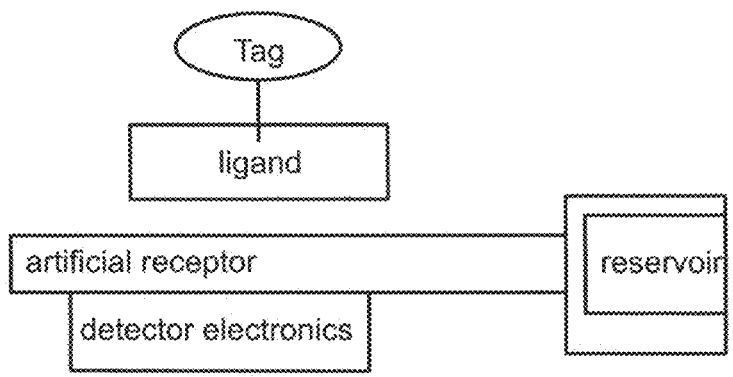

FIG. 11 is a schematic illustration depicting a controlled drug release. A quantity of the drug to be released is held in a reservoir, and in the meantime a molecule for which the artificial receptor has an affinity is released into the bloodstream. The molecule that is released has a magnetic particle attached thereto, thus enabling the attachment of the particle to be sensed at the device. The molecule with the magnetic particle reaches the artificial receptor and binds thereto. The magnetic particle is detected via its magnetic field. Detection of the magnetic particle triggers release of the drug. The reservoirs can be placed with the devices deep inside the body at the points where drug administration is required. The particles can then be systematically administered to control release of the drug at the device. The particles can be used to ensure that a given quantity of the drug is released using timing based say on the half-life of the drug within the body.

Figure 12:
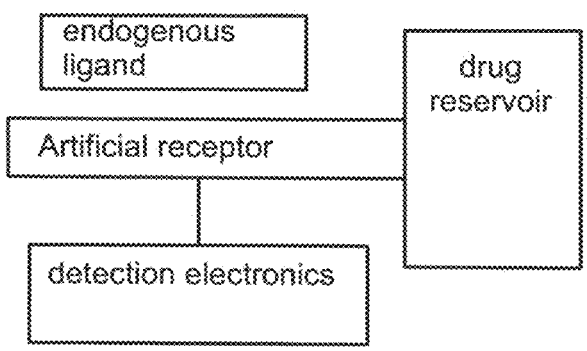

FIG. 12 a schematic illustration depicting a binding of an endogenous ligand to the artificial receptor. Binding of the ligand affects the electric field of the device temporarily and may cause a temporary signal spike which may be detected following suitable noise reduction. The ligand may be selected to be representative of biological activity that it is desired to monitor. For example the ligand may be an antibody, and the presence or level of too many of the antibodies may indicate a certain condition. The condition may be treatable with a given drug which can be part of a controllable release feature as before.

Figure 13:
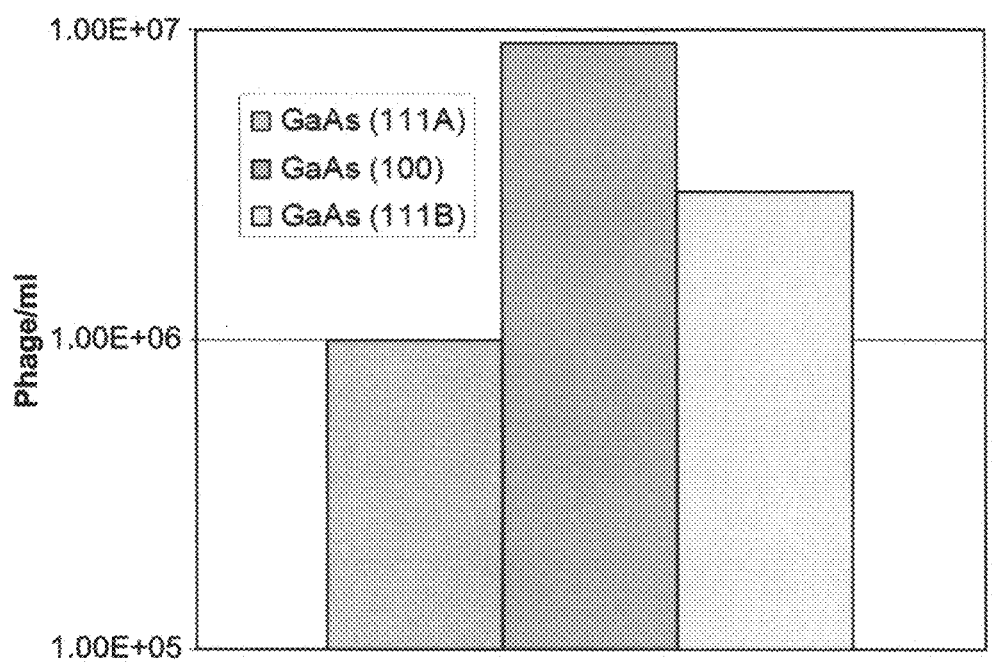

FIG. 13 is a histogram depicting the density of M13KO7 non specific binding to the various substrates: GaAs (111A), GaAs (100) and GaAs (111B). Note the higher binding of M13KO7 helper phage to GaAs (100) compared to GaAs (111A).

Figures 14A, 14B, 14C:
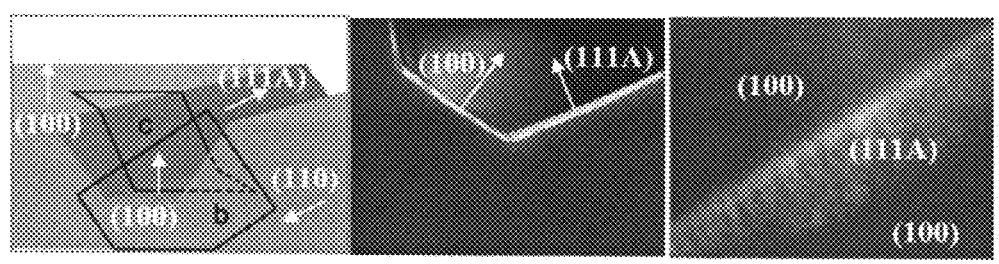

FIGS. 14a-c depict selective binding of the scFv fragment to the crystalline facets. FIG. 14a—A schematic diagram of the etched trench labeled with the various crystalline facets. Black frames correspond to the views depicted in FIGS. 14b and c. FIG. 14b—SEM image of a cut across the trench. FIG. 14c—Fluorescence image of the trench viewed from the top. Fluorescence is confined to the (111A) slopes proving selective binding of the scFv fragments to that facet. Note the negligible binding of antibody molecules to the (100) facets.

Figure 15:
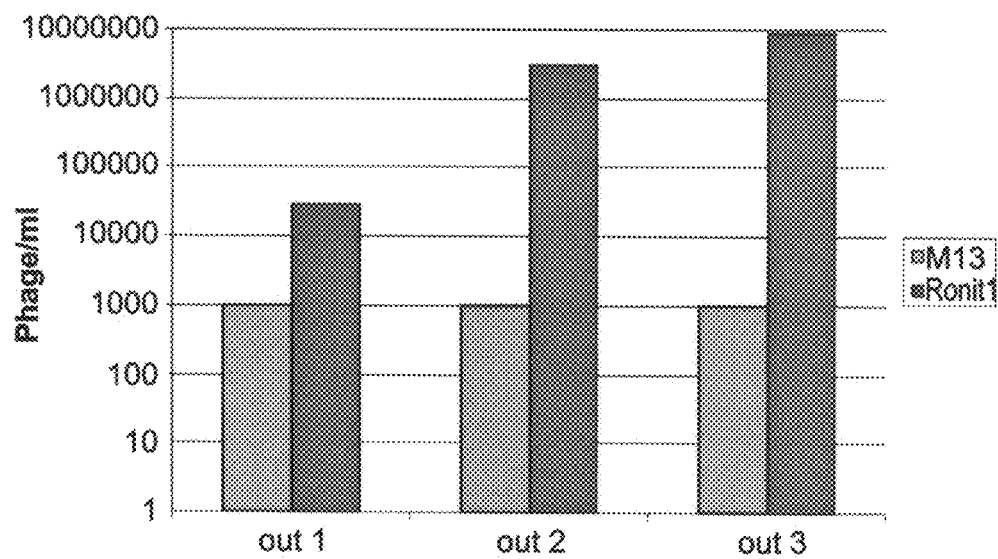

FIG. 15 is a histogram depicting the enrichment of anti-GaAs (111A) phages carrying scFv fragments vs. panning cycle. Phage concentration has been deduced by counting colonies of E. coli bacteria infected with different dilutions of the phages recovered after each cycle. Shown is the number of phage/ml following the three panning cycles (cycle 1—out 1; cycle 2—out 2; and cycle 3—out 3). The monotonic increase in binding of phages carrying scFv (Ronit1) is contrasted with the much weaker, non-specific binding of similar phages lacking the scFv antibody (M13). The value of 1000 phages/ml in the phages lacking the scFv antibody sets an experimental upper limit on their binding. The actual values are likely to be smaller.

Figure 16:
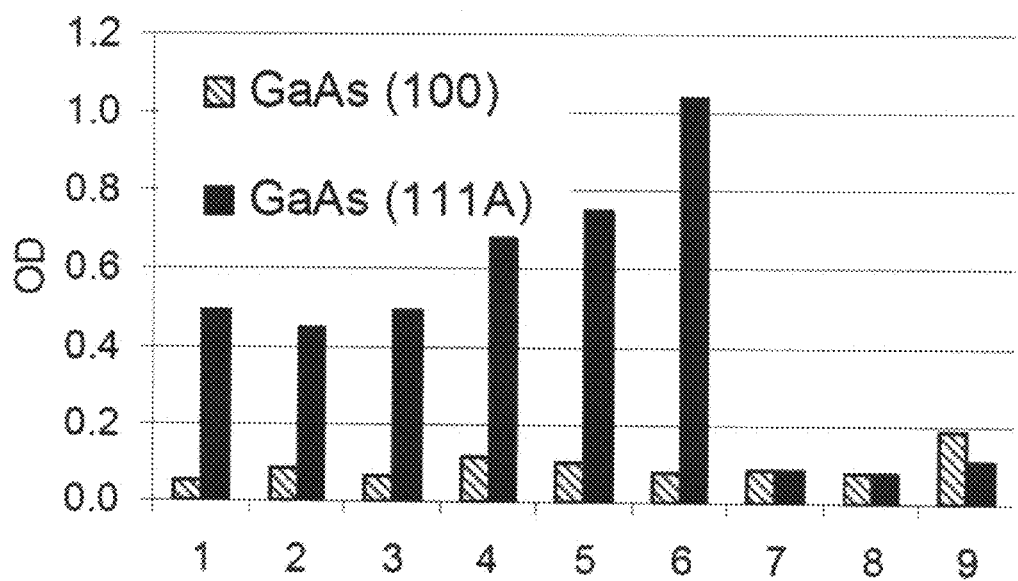

FIG. 16 is a histogram depicting binding of the soluble EB scFv molecule on GaAs (111A) and GaAs (100). Bars 1-6 display the results of 6 comparative ELISA assays of the EB scFv molecule on GaAs (111A) and GaAs (100) substrates pieces, 4×4 mm each. After washing the substrates, the bound antibodies were reacted with anti-human Horseradish Peroxidase (HRP) and binding was quantified by adding tetramethylbenzidin (TMB) colorimetric substrate, and reading the resulting O.D. at 450 nm. The O.D. reflects the number of bound molecules in arbitrary units. Bars 7-9 display the results of three control experiments and can be used to estimate the background signal, about 0.1 O.D, coming from sources other than selective binding of the scFv to the semiconductor substrates. Bars 7 quantified non-specific binding of the secondary anti-human HRP to the ELISA plate in the absence of the EB scFv and semiconductor substrates. Bars 8 corresponded to non-specific binding of the scFv to the plate, and bars 9 to non-specific binding of the secondary antibodies to the semiconductor substrates.

Figure 17:
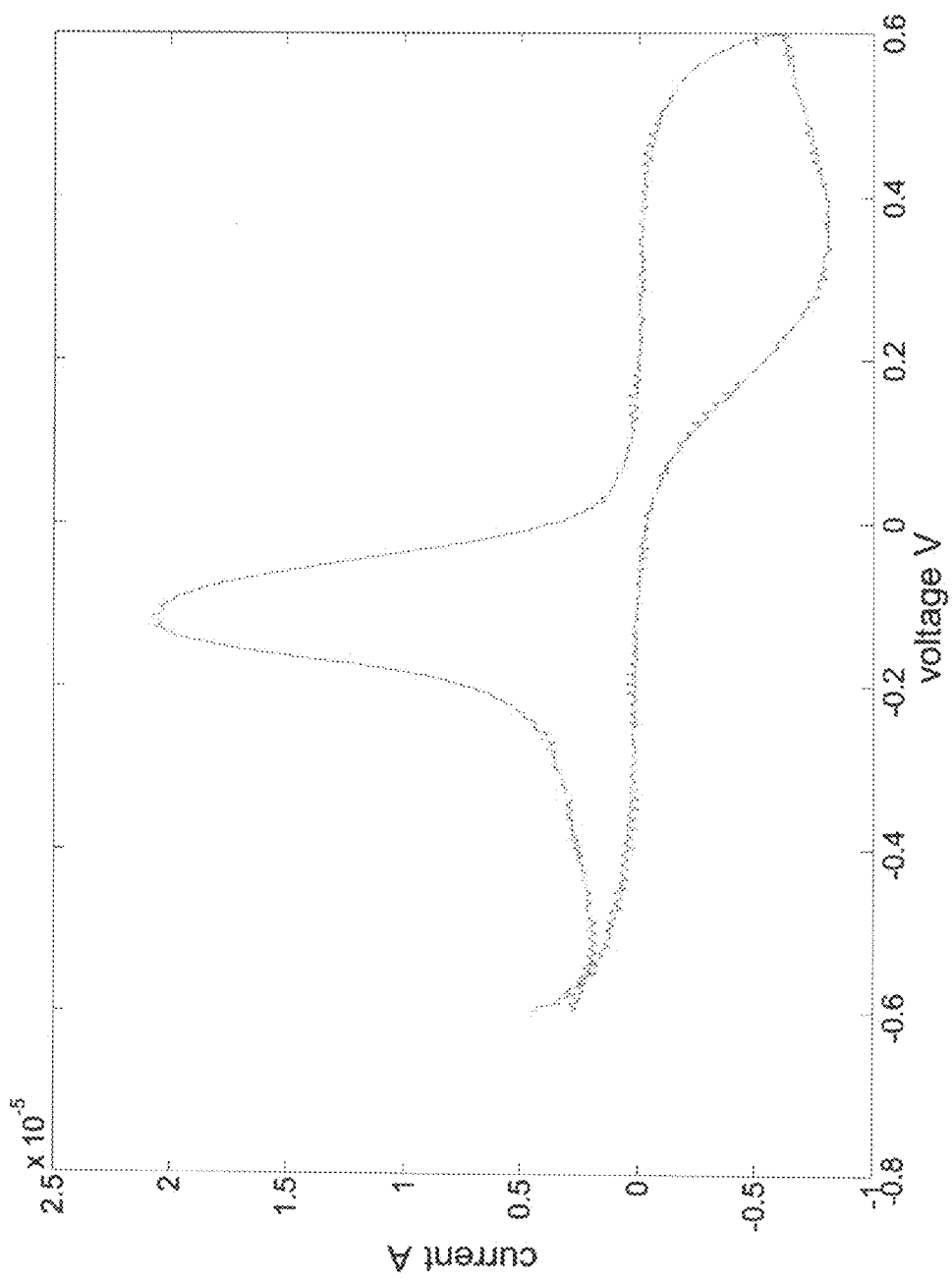

FIG. 17 is a graph depicting current as a function of voltage of the HQ/BQ monolayer. When scanning from −0.6 V to 0.6 V and back (red line), two peaks are shown, the first centered at 0.4 V is due to the oxidation of the HQ to BQ, the second peak centered at −0.3 V is due to the reduction of the BQ to HQ. The CV (cyclic voltammetry) curve is highly stable and repeated scans reproduce the same curve.

Figures 18A, 18B:
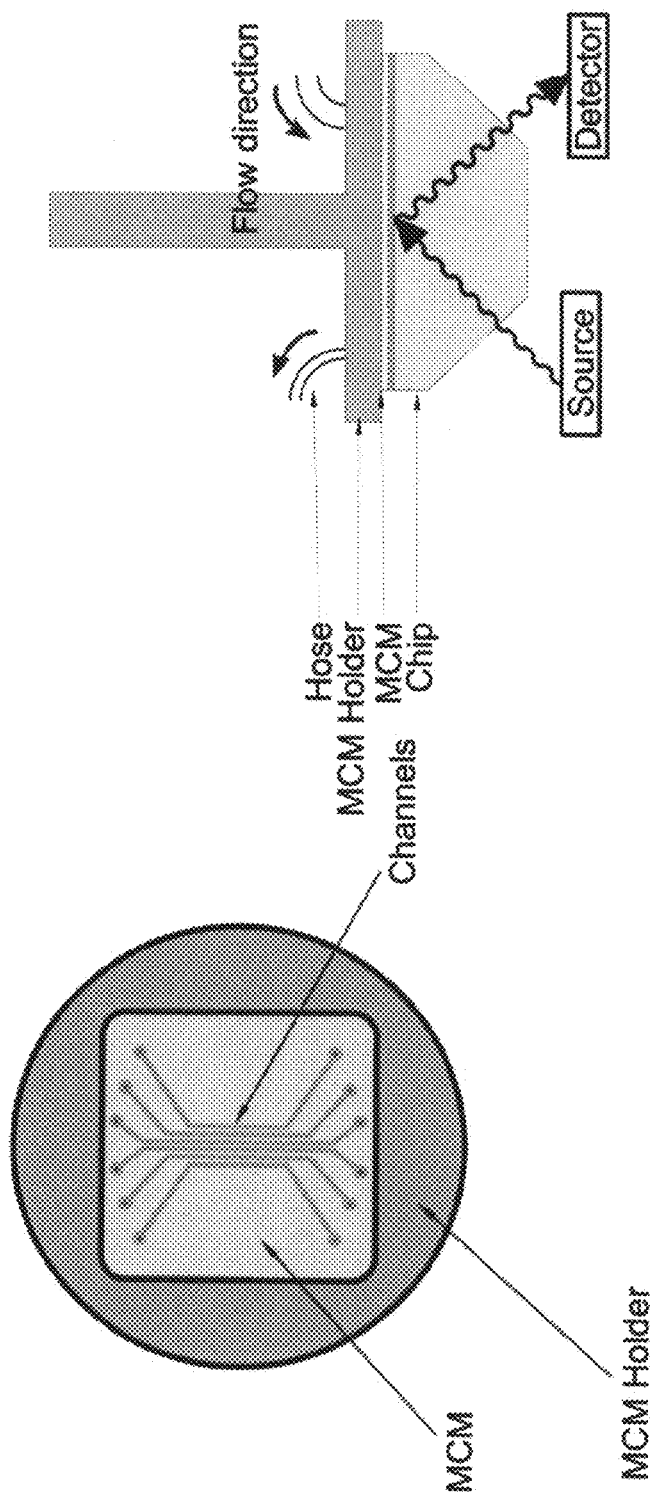

FIGS. 18a-b schematically depict a configuration of chip design. FIG. 18a—MCM (micro channel module) made of RTV casting of the six channels through which solution flows. FIG. 18b shows a measuring system consisting of the chip, MCM, and hoses.

Figure 19A:
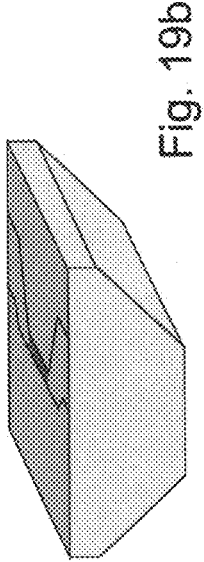
Figure 19B:
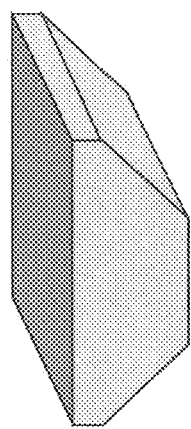
Figure 19D:
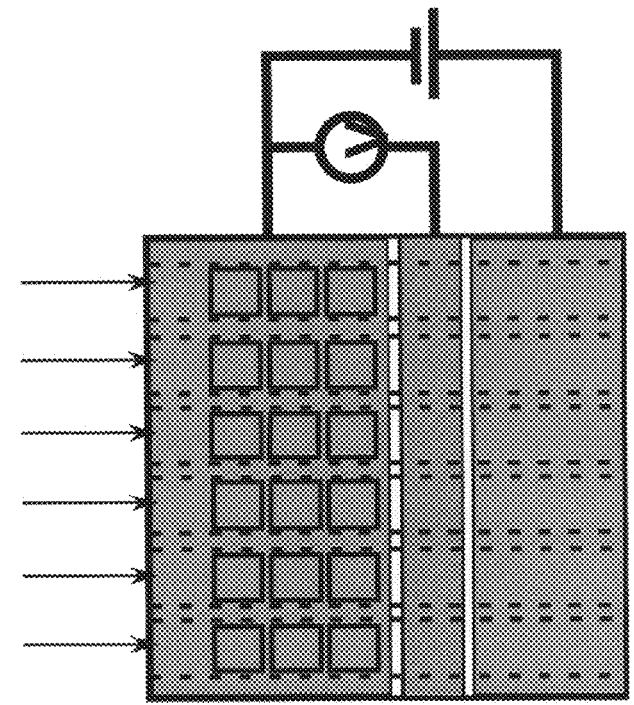
Figure 19C:
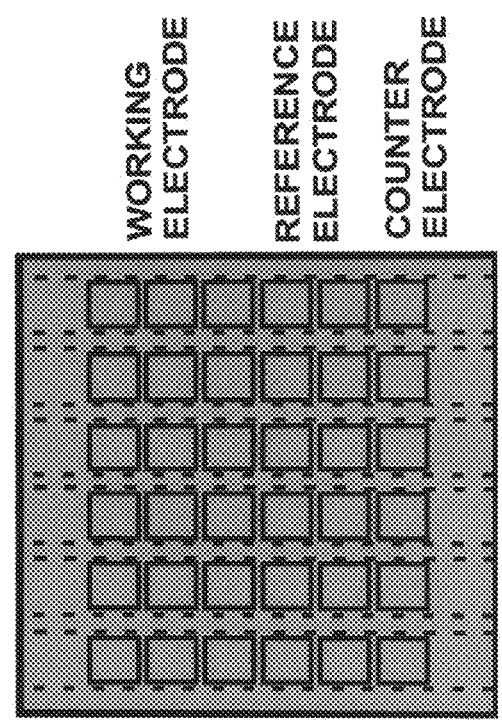

FIGS. 19a-d schematically depict a configuration of a modified chip consisting of three insulated electrodes. FIGS. 19a-b—The chip as a whole containing a prism on which chromium (not shown) and gold layer are deposited. The original chip is shown in FIG. 19a and the modified one is shown in FIG. 19b. FIGS. 19c-d-Monitored area of both the original (FIG. 19c) and modified (FIG. 19d) chip. Signified by dashed lines are the six channels. AOIs (areas of interest) are denoted by squares. Also, the electric circuit used in this study is schematically shown.

Figure 20:
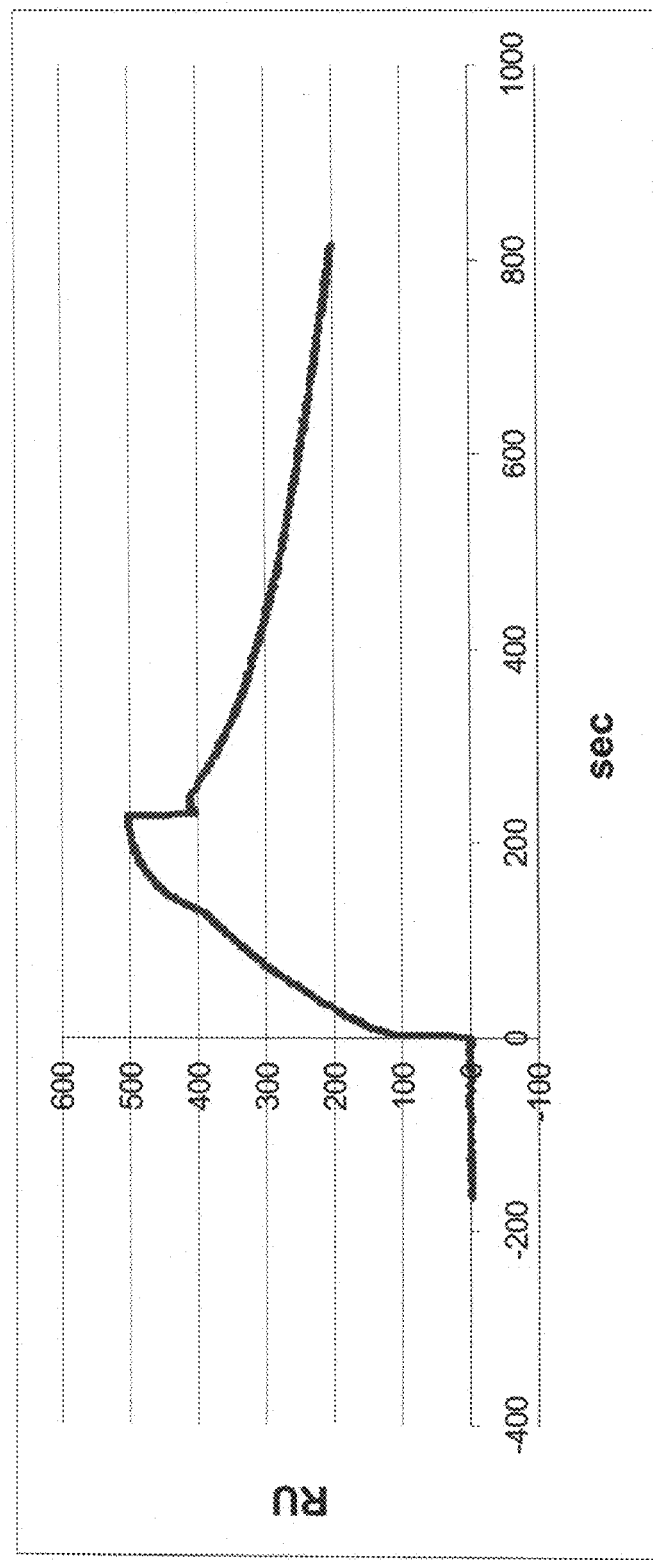

FIG. 20 is a graph depicting the binding of the soluble 12A scFv antibody to the HQ monolayer as determined in SPR [presented in RU as a function of time (seconds)]. The four binding channels were injected at t=0 sec with the soluble 12A scFv antibody solution, in PBS pH 7.2. At t-=230 sec, antibody injection was terminated and a decline had set when pure PBS buffer pH 7.2 was injected instead. As can be seen after the washing the antibodies remained bound to the hydroquinone monolayer.

Figure 21:
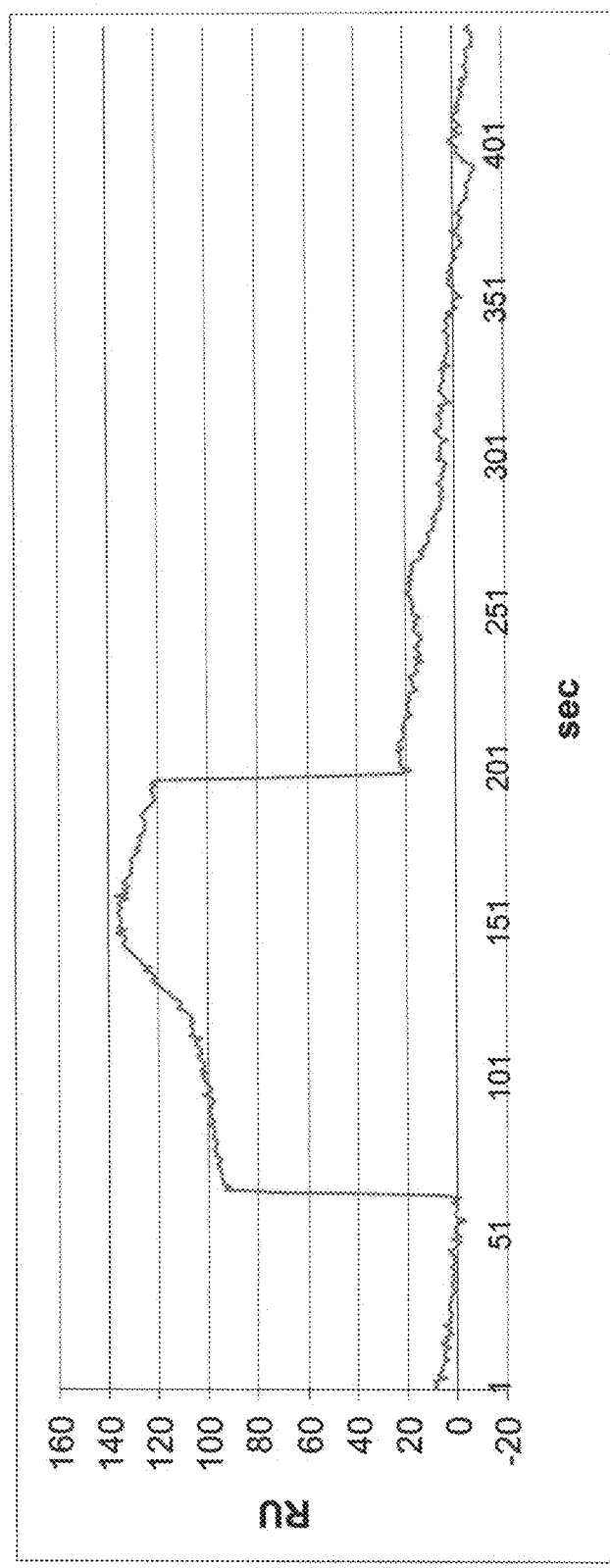

FIG. 21 is a graph depicting the lack of binding of the soluble 12A scFv antibody to the BQ monolayer. Binding was determined using SPR and is presented in RU as a function of time (seconds). In order to generate a BQ monolayer, potential pulses of +0.6 V applied for 30 seconds were employed. At t=0 seconds the soluble 12A scFv antibody was injected to the binding channel. At t=125 seconds, antibody injection was terminated and a decline had set when pure PBS buffer pH 7.2 was injected instead. As can be seen, after the washing all the antibodies dissociate from the benzoquinone monolayer.

DESCRIPTION OF THE EMBODIMENTS OF THE INVENTION

The invention relates to antibodies capable of specifically binding an artificial receptor which comprises hydroquinone on its surface but is incapable of binding the artificial receptor when comprising a benzoquinone. In addition, the invention relates to methods and system using same for controllably delivering a molecule-of-interest (e.g., drug) to a tissue. The invention further relates to methods of using the artificial receptor for typing ligands, determining binding domains in proteins, targeted delivery of drug molecules, electronic capture and release of drugs, and electronic triggering and suppression of biological reactions such as gene expression.

The principles and operation of an artificial receptor device according to the invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While reducing the invention to practice, the present inventors have uncovered that individually contacted nano-scale electrodes, each biased to an individual set potential, can be used as artificial receptors capable of binding biological moieties and that such receptors can be used in any application which is based on molecular recognition involving electrostatic interactions such as to type ligands, identify binding domains of proteins and target delivery of drugs.

As is shown in Examples 1-4 of the Examples section which follows, the present inventors have shown that a specific facet of a semiconductor can differentially bind phage display antibodies as well as soluble antibodies (which are detached from the phages) and thus can be used to control the binding of biological moieties thereto.

Thus, according to one aspect of the invention there is provided an artificial receptor. The artificial receptor comprising a non-biological surface having an extent, the surface having unique surface electrical properties that vary over the extent, the electrical properties being such as to configure an electrical field about the surface to provide specific binding for a target moiety.

The phrase "artificial receptor" which is interchangeably used herein also as "an electrode" refers to a specific device made of a material (e.g., crystal) such as a semiconducting or a conducting material, which is configured to exhibit a unique surface electrical properties to provide specific binding as described hereinbelow for a target moiety such as a target biological moiety.

The embodiments use electric fields which are configured to specifically bind biological moieties. A first embodiment has a permanent electric field pattern preset for a specific molecule. A second and a third embodiment are programmable to bind and release specific molecules at pre-determined times.

Referring now to the drawings, FIG. 1 illustrates a first preferred embodiment of the invention in which a device 10 is set up a surface 12 and an electric field about that surface. An isoelectric contour 14 illustrates a possible shape for the field.

Surface 12 of device 10 preferably includes a plurality of regions 16-26, each having a predetermined electrostatic field strength. Regions 16-26 within device 10 are constructed with built-in static electric fields that between them give the overall contour 14. The unique contour 14 is capable of binding a specific biological moiety as described hereinbelow (e.g., a protein). More particularly, the field binds a specific sub-region of the protein just as an antibody binds an antigen (e.g., epitope) or an enzyme's active site binds a corresponding site on a substrate.

It will be appreciated that since the specific interaction between biological moieties such as proteins often involves a unique three-dimensional binding site having a size of a few nanometers up to a few Angstroms, the regions defining the surface of the artificial receptor of the invention are preferably in the Angstrom order of magnitude, more preferably, in the nanometer or tens of nanometer order of magnitude, so as to enable specific binding of biological moieties thereto.

Surface 12 of device 10 can be made of various materials having selected electrostatic properties. Non-limiting examples of such materials include ceramics and semiconductors (e.g., crystals or polycrystals such as PZT, GaAs and silicon). It will be appreciated that when a specific region is made of a crystal, the size of the region is preferably in the magnitude of five to ten lattice constants.

For example, device 10, is preferably constructed from ceramic bearing ferroelectric particles, allowing the ceramic to be pre-electrified with the desired field strength.

The result is an artificial receptor whose surface has defined and unique electrical properties that vary over its extent, the properties giving rise to an electrical field over the surface which provides specific binding for the target moiety such as a biological moiety or a chemical moiety (e.g., polymer and/or small molecule).

It should be appreciated that the electrodes need not be planar. They may comprise, for instance, carbon nanotubes and/or silicone nanowires sticking out of the plane. The same is true for the gaps between electrodes.

Binding of the biological moiety to the surface is of a proximity and orientation which mimics the equivalent biological binding pair and the resultant affinity is of a $K_D$ range of preferably $10^{-5}$-$10^{-15}$ M, preferably at least $10^{-6}$ M, preferably at least $10^{-7}$ M, preferably at least $10^{-8}$ M, preferably at least $10^{-9}$ M, preferably at least $10^{-10}$ M preferably at least $10^{-11}$ M, preferably at least $10^{-12}$ M, preferably at least $10^{-13}$ M, preferably at least $10^{-14}$ M, preferably at least $10^{-15}$ M.

It will be appreciated that determination of such affinity can be performed using methods known in the art, such as, by scatchard analysis.

It will be appreciated that to enable the binding of a wide selection of molecules (e.g., biological moieties or chemical moieties) to the artificial receptor of the invention and to control the binding of such molecules, the artificial receptor of the invention is preferably programmable to provide different electrical fields as desired.

Such programming can be achieved by configuring at least one electrode capable of being biased to a unique electrical property.

An example for such configuration is presented in FIGS. 2a-d. A semiconductor wafer laminate 30 is constructed of layers of semiconductor. The layers are alternate conductors A and insulators B (e.g., GaAs/AlGaAs or metal/metal oxide; FIG. 2a). The wafer may then be sliced along a transverse cross section to provide a surface in which the alternating conducting and insulating layers cross the width of the surface (FIG. 2b). FIG. 2c shows a magnified view of part of the length of the surface showing the alternating conducting layers A and insulating layers B. The cleaved surface comprises alternating strips with atomically sharp interfaces. To gain electrical control over the binding capacity of the artificial receptor of the invention, the conducting layers are independently electrifiable layers. Thus, the user can set up any desired electrical field over the surface by controlling the electricity passed through each electrifiable layer.

FIG. 2d illustrates an insulating coating layer 32, which may be applied on the surface of the artificial receptor. Cavitations 34, which are holes in the insulating coating allow binding of the molecules to the surface. An example of coating layer 32 is a glass. Preferably cavitations 34 are in the Angstrom or nanometer scale.

The glass is preferably passivated against protein binding. Using conventional methods in microelectronics the A layers are all contacted electrically away from the cleaved edge. The result is a large array of cavitations in the coating layer, each over an A/B interface. The conducting, A side of all spots can then be biased relative to the solution. The exposed A/B interface is the target for the antibodies. Since the peptide binding sites are typically either charged or polarized, the local electrostatic potential created by a different biasing of the A electrode should affect differently various antibody molecules.

The surface of the artificial receptor may comprise zero dimension, one dimension, two dimensions and three dimensions.

The surface of the artificial receptor may comprise electronically controllable hydrophobic coating to allow controllable hydrophobic properties for each independently electrifiable layer.

According to preferred embodiments of the invention, variable electrical fields are applied to the regions. Such electrical fields can be controlled by adjusting the voltage and/or current supplied to the electrode or the layer as described hereinabove and those of skills in the art are capable of controlling the electrical fields.

Thus, the electrically biased artificial receptor is capable of binding various targets depending on the resultant electrical field provided at each time.

According to preferred embodiments of the invention, the surface comprises switchable wiring, such wiring being switchable to provide the unique electrical properties. Preferably, such wiring is variably switchable, thereby providing specific binding to different target biological moieties as desired.

Reference is now made to FIG. 3, which is a simplified diagram showing a preferred switching device for switching the different layers as desired.

Preferably, the wafer layers are connected to the switching device or selector 38, which allows voltage levels to be electronically selected for each of the independently electrifiable layers. The electrical field may thus be varied to provide specific binding to different targeted biological moieties. Typically an overall power source 40, which may be a battery or a main fed power supply, supplies a series of voltage regulated power sources 42.1 . . . 42._n_, each set at different voltage levels. A switching matrix 44 then connects any one of the layers 46.1 . . . 46._n_ to any one of the regulated power sources. Preferably the switching matrix is controlled by software. It will be appreciated that the switching device described with respect to FIG. 3 is merely an example and other alternatives will occur to the skilled person.

An alternative approach to control the microscopic electric field landscape of the artificial receptor of the invention relies on the use of materials which upon application of an electric field, their unit cell or molecular structure is changed, resulting in a change in the electric field produced thereon. Such materials are for example, ferroelectric substances (e.g., PLZT) which exhibit high dielectric constants and are therefore changeable following application of changes in their electric field.

One example for a ferroelectric material is a Perovskite-like crystal, in which a high valence cation is encapsulated in an oxygen octahedron. The oxygen together with the A atoms form a face center cubic (fcc) crystal with the latter atoms at the corners. The high temperature phase is cubic and, hence, lacks electric moments. As the temperature is reduced the material may undergo a series of structural phase transitions to lower symmetry structures accompanied by large local electric moments. Since the central cation has a large charge and relatively broad energy minima, the electrical susceptibility is very large and the dielectric constant can approach values as high as 1000-5000. The corresponding polarization fields are enormous. One such crystal, PLZT, is particularly attractive for the scope of the invention. At a ratio of 9/65/35 the virgin ceramics maintains an isotropic cubic phase. An application of a moderate electric field shifts the crystal to the rhombohedral or tetragonal phases characterized by enormous local electric dipoles. When the external field is removed the polar phase relaxes instantaneously back to its unpolarized cubic phase. The magnitude of the generated dipoles depends on the applied field. The large dielectric constant guarantees extremely large local electric moments.

For example, as described in FIG. 5, PLZT crystal 64 can be placed between a metal cathode 60 and a metal anode 62. Antibodies which selectively bind to PLZT subjected to a certain field can be easily identified.

In the preferred embodiment, different target molecules (e.g., antibodies) bind selectively to the same crystal under different applied fields and released under other fields.

The physics of PLZT is fully understood and the phase diagram as a function of composition, temperature, and applied field is tabulated.

It will be appreciated that the surface of the artificial receptor of the invention can be further modified by attaching materials or molecules capable of modifying the electrical property of the surface, as well as the hydrophilic or hydrophobic properties of the surface which may affect the capacity of the surface to form hydrophobic interactions, hydrogen bonding and van der Waals interactions with biological moieties.

Several types of substances, molecules and/or monolayers of molecules can be used to change the electric field of the surface according to this aspect of the invention. These include molecules and materials which following the application of an electric field, mechanical stress and/or change in a temperature are capable of modifying the electric field generated thereupon. Substances which may affect the hydrophobic or hydrophilic properties of the surface may be, for example, charged peptides, phospholipids and the like, which following the application of an electric field can fold or change their relative orientation with respect to the surface.

For example, organic molecules such as hydroquinone, Rotaxane and charged organic (e.g., ferrocene) or biological polymers, undergo atomic and/or molecular changes following the application of an electric field. FIGS. 6 and 7 illustrate the molecular and structural changes occurring following the application of an electric field on hydroquinone and Rotaxane, respectively.

Hydroquinone looses two hydrogen atoms following the application of an electric filed. The hydroquinone molecule may be attached to a substrate via an alkane tail. In either case the molecule may be switched between two stable states by electro-protonation. An antibody molecule selective to one of the configurations is attracted or released from the Hydroquinone depending on its state. The Hydroquinone transduces in this case the electronic signal to a change that is readily recognizable by antibodies.

Rotaxane is a linear dumbbell shaped molecule inserted into a mobile molecular ring having two redox states. The ring may rest in one of two positions along the molecule depending on the oxidation state. The latter is controlled by application of a bias between the substrate to which the dumbbell molecule is bound and the solution. It is very likely that antibodies can be selected to the two different configurations of the molecule, namely for the two positions of the ring along the molecule, hence providing an electrical control over which antibody binds the surface.

The ferroelectric materials (e.g., PLZT) which are described hereinabove represent an example of non-organic materials which upon the application of electric field exhibit structural changes that affect the electric field and, hence, the target for antibodies and other bio-molecules.

Pyroelectric materials can also be used to modify the electric field of the surface of the artificial receptor of the invention. Following the application of a temperature change, the material undergoes structural changes of the unit cell or a molecular change which result in a modified electric field. Non-limiting examples for such materials which can be used along with the invention include, Li—Ta—$O_3$ and triglycine sulfate (TGS).

Piezoelectric materials can also be used to modify the electric field of the surface of the artificial receptor of the invention. Following the application of electric voltage, the material undergoes conformational changes which result in a change in the unit cell. Reversal to the original conformation usually requires the application of an opposite voltage since the material is somewhat hysteretic. Non-limiting examples for such materials which can be used along with the invention include, PZT and polyvinylidene fluoride (PVDF).

Ferroelastic materials can be also used to modify the electric field landscape of the surface of the artificial receptor of the invention. Following the application of mechanical stress, the material undergoes conformational changes which result in a change in the electric field. A non-limiting example for such materials which can be used along with the invention is $LaAlO_3$.

It will be appreciated that several biological moieties can be also attached to the surface of the artificial receptor of the invention in order to modify its electric field. For example, peptides can be attached to the surface and following the application of an electric field the peptide can change its configuration, e.g., can form a cyclic molecule or can attach along the surface. Such a change in configuration results in a change of the electrical properties of the surface or hydrophobic nature, or display of certain groups which can be used to selectively bind biological moieties.

It will be appreciated that such materials and substances which following structural and molecular changes (as a result of mechanical stress, temperature change and/or electric field change) are capable of modifying their electric field can be used to form the regions of the artificial receptor instead of the crystals or semiconductors.

While further reducing the invention to practice, the present inventors have devised an artificial receptor having a surface with switchable electrical conductive tracks, the conductive tracks being switchable to configure an electrical field about the surface to provide specific binding for a target moiety (e.g., a target biological moiety).

According to preferred embodiments of the invention, the artificial receptor further comprises a switching control for switching the conductive tracks.

Reference is now made to FIG. 4, which is a simplified diagram illustrating a further preferred embodiment of the invention. The device of FIG. 4, like the device of FIGS. 2a-d is a programmable device so that the electrical fields produced can be changed during use. Device 50 comprises a conventional semiconductor wafer surface 52 on which are patterned conductive tracks 54 using conventional semiconductor manufacturing techniques. The conductive tracks are switched using transistors in the conventional manner. It is stressed that in a standard semiconductor integrated circuit, electrical fields are produced and are generally a nuisance, giving rise to various unwanted phenomena as stray or parasitic capacitance, which slow down the propagation rates of the leads, and introduce noise and interference between the components. The present embodiments however make use of the field to target the desired molecules.

Device 50 may include additional elements such as a covering layer over the semiconductor surface, as described above.

Elaborate Artificial Receptor (Electrode) Set

It will be appreciated that for activation or suppression of a single bio-process or even for the selection between two bio-processes a single electrode with two states is enough. For selection between multiple pathways or activation/suppression of multiple processes an elaborate electrode set with numerous biasing configurations may be required. The electrode size and separation may vary according to the application. Electrodes larger than ~10 nanometer may be fabricated by conventional methods of micro and nanoelectronics such as electron beam lithography and focused ion beam. Smaller electrodes and/or smaller spacing between electrodes, still with an individual electrical contact to each of the electrodes can be realized by the utilization of metal/metal oxide alternating layers grown by molecular beam epitaxy. Separate contacts to the individual layers can be achieved by using a moving shutter during growth and later use of photolithography to contact the exposed metallic layers, this being illustrated in FIGS. 8a-d. FIGS. 8a-d depict successive stages in the manufacture of the electrode layers, showing how the individual conducting layers can each have independent electrical connections. FIG. 8a shows an initial stage in which shutter 70 is located at the far left side of wafer 72, allowing deposition of a pair 74 of successive conducting and insulating layers. Moving to FIG. 8b and the shutter 70 is moved, say by 100 micrometers to the right and a further pair 76 of conducting and insulating layers is deposited. The shutter 70 is then moved further to the right in FIG. 8c and two more layers 78 are deposited. In FIG. 8d, a further pair 80 of layers is deposited with the shutter 70 moved even further to the right. The resulting structure has terraces spaced by say 100 micrometer, each exposing a conducting layer. Using conventional photolithography, each such layer can be electrically contacted independently. Upon cleavage of the substrate perpendicular to the deposition direction, the layers are exposed in the form of thin lines, each contacted separately. Modern Molecular Beam Epitaxy technology facilitates fabrication of layers as thin as two monolayers spaced by an insulating layer of a comparable thickness. After cleavage these dimensions translate to conducting or electrode layers which are two monolayers thick, separated by similar insulating layers.

An alternative approach relies on extension of the distance between the biological binding sites. The simplest construction would be an IgG antibody composed of two halves, each selective to a different bias. Such a construction should be selective to two electrodes spaced by a few nanometers. If two antibodies are fused at their tails (as occurs naturally with IgA) that distance can increase to 10-20 nm. The latter distance is easily accessible by present nanotechnology and it should be possible to contact independently two interfaces spaced by such a distance. One may obviously utilize other artificial or natural constructs like IgM pentamers.

Floating Electrodes

The electrodes as described above need not necessarily be fabricated on a supporting substrate nor need they be exclusively biased by an external power supply, although in several preferred embodiments they are so biased. In one embodiment the electrodes may comprise a microscopic p-n junction realized in a semiconducting nanocrystal. Due to the rectifying nature of such a junction, application of radiation to the nanocrystal results in generation of bias between the two poles of the p-n junction. This bias is equivalent to an external bias applied to electrodes by connecting them to an external source. The possibility to apply bias from a distance by radiation at a desired timing facilitates, for instance, drug release by external radiation. For that the drug is fused to the antibody and the latter is released by the induced voltage as described above.

Other bias sources include, e.g. a microscopic battery or even a chemical cell whose output depends on certain biochemical parameters, such as pH. A source like that may trigger antibody binding or release from the electrodes based on the presence of certain chemicals. Such an arrangement facilitates e.g. localized drug release depending on certain biochemical conditions.

The devices (or the electrodes) described hereinabove can be connected together in any desired way in order to provide three-dimensional fields. Furthermore, numerous devices (or electrodes) may be connected together to form arrays. Thus, the electrodes in the array may be identical, designed to fish out the maximum number of a target molecule, or the arrays may comprise electrodes with different fields or electrodes programmed differently, so that a range of target molecules can be searched for.

The following section describes possible embodiments of the electrodes set. The processes mentioned in the text are known to practitioners in the fields of micro and nanoelectronics, crystal growth, surface chemistry, etc.

Electrodes material—The electrode material used by the method of the invention can be any type of material or materials combination. Following is a list of preferred materials:

(a) Metal electrodes—deposited on an insulating substrate (planar geometry) on a substrate such as glass, alumina, sapphire, etc. Examples for metals include gold, platinum, silver, aluminum, etc. The electrodes may be defined either by first depositing or epitaxially growing a metal layer (e.g. by molecular beam epitaxy, chemical vapor deposition, atomic layer deposition, electrochemistry) and then patterning it by e.g. electron beam lithography or focused ion beam (FIB). Alternatively, the electrodes may be deposited or grown on the substrate already in their patterned form, for instance by patterned epitaxial growth or by FIB deposition.

(b) Semiconductor electrodes—deposited on an insulating substrate (planar geometry) on a substrate such as glass, alumina, sapphire, etc. Examples for semiconductors include silicon, GaAs, InAs, CuO, etc. The electrodes may be defined either by first depositing or epitaxially growing a semiconductor layer (e.g. by molecular beam epitaxy, chemical vapor deposition, atomic layer deposition, electrochemistry) and then patterning it by e.g. electron beam lithography or focused ion beam (FIB). Alternatively, the electrodes may be deposited or grown on the substrate already in their patterned form, for instance by patterned epitaxial growth or by FIB deposition.

(c) Conducting polymers electrodes—deposited on an insulating substrate (planar geometry) on a substrate such as glass, alumina, sapphire, etc. Examples for conducting polymers include PPV, polyanilin, etc. The electrodes may be defined either by first depositing or epitaxially growing a polymer layer (e.g. by molecular beam epitaxy, chemical vapor deposition, atomic layer deposition, electrochemistry) and then patterning it by e.g. electron beam lithography or focused ion beam (FIB). Alternatively, the electrodes may be deposited or grown on the substrate already in their patterned form, for instance by patterned epitaxial growth or by FIB deposition. The conducting polymers may be deposited or grown either parallel to the surface or angled to it.

(d) Semiconductor superlattice (vertical geometry)—Alternating layers of various semiconductor materials are grown on a substrate. In the simplest embodiment depicted in FIGS. 1a-d the superlattice comprises two alternating layers of conducting and insulating semiconductors. In another realization the structure may comprise an elaborate sandwich of different materials. The structure may be grown by molecular beam epitaxy (MBE), chemical vapor deposition (CVD), metalo-organic molecular beam epitaxy (MOMBE), liquid phase epitaxy (LPE), chemical deposition, electrochemistry, atomic layer deposition, etc. The wafer is then cleaved as described in FIG. 1b and the layers exposed by the cleavage serve as electrodes. The layers may be crystalline, amorphous, polycrystalline, or combinations of the above.

(e) Metal/insulator superlattice (vertical geometry)—Alternating layers of various metals and insulating layers, e.g. metal oxides or ceramics, are grown on a substrate. In the simplest embodiment depicted in FIG. 5 the superlattice comprises two alternating layers of metal and insulating metal oxide. In another realization the structure may comprise an elaborate sandwich of different materials. The structure may be grown by molecular beam epitaxy (MBE), chemical vapor deposition (CVD), metalo-organic molecular beam epitaxy (MOMBE), liquid phase epitaxy (LPE), chemical deposition, electrochemistry, atomic layer deposition, etc. The wafer is then cleaved as described in FIGS. 1a-d and the layers exposed by the cleavage serve as electrodes. The layers may be crystalline, amorphous, polycrystalline, or combinations of the above.

(f) Conducting polymers (vertical geometry)—Alternating layers of various conducting polymers and insulating layers, e.g. metal oxides, ceramics, or insulating molecules and polymers are grown on a substrate. The structure may be grown by molecular beam epitaxy (MBE), chemical vapor deposition (CVD), metalo-organic molecular beam epitaxy (MOMBE), liquid phase epitaxy (LPE), chemical deposition, electrochemistry, atomic layer deposition, etc. The wafer is then cleaved as described in FIGS. 1a-d and the layers exposed by the cleavage serve as electrodes. The layers may be crystalline, amorphous, polycrystalline, or combinations of the above.

(g) Molecular conductors and semiconductors—like carbon and other nanotubes provide in a natural way nanometer scale electrodes. Carbon nanotubes can be spin coated on an insulating layer or grown from metal catalysts. A particular attractive approach in the growth of multiple tubes from patterned catalysts islands. Other molecular conductors like semiconductor nanowires, nanorods, and dots can be used. The latter include also self assembled semiconductor dots defined by strain on a semiconductor substrate.

(h) Functionalized or unfunctionalized biomolecules—see E. Braun, Y. Eichen, U. Sivan and G. Ben Yoseph, DNA templated assembly and electrode attachment of conducting silver wire, *Nature,* 391, 775 (1998); K. Keren, M. Krueger, R. Gilad, G. Ben-Yoseph, U. Sivan and E. Braun, Sequence-Specific Molecular Lithography on Single DNA Molecules, *Science,* 297, 72 (2002); and K. Keren, R. S. Berman, E. Buchstab, U. Sivan, and E. Braun, DNA-Templated Carbon-Nanotube Field Effect Transistor, *Science* 302, 1382 (2003), which are fully incorporated herein by reference.

Ferroelectric and high dielectric constant electrodes—Ferroelectric and high dielectric constant ceramics and organics provide an efficient way for the creation of large local electric moments. The principle is presented hereinabove and in FIG. 5. Multiple electrode sets can be fabricated either in a planar geometry or a vertical geometry as described hereinabove.

Electrode functionalization and coating—The electrodes can be functionalized by biological, non-biological, or organic molecules. The latter may serve to modify the surface properties such as hydrophobicity/hydrophilicity, charge, stability, roughness, compatibility with the solutions and the molecules in solution, non-specific binding, etc. Functionalization may also provide an electronic control over surface properties as detailed e.g. in Frechette and Vanderlick, Langmuir 17, 7620 (2001); Barten et al. Langmuir 19, 1133 (2003). The electrodes can also be coated with polymers, gels, etc. for protecting them or the antibodies against chemical processes such as oxidation or reaction and for increasing the effective electrode area. Certain substances such as agarose provide a convenient environment to the biomolecules. The electrodes can also be modified with thin insulating layers such as silica and alumina. They can also be covered with colloids and beads.

Contacting individual electrodes—Individual electrodes are contacted by conventional microelectronics techniques. In the case of semiconductor superlattice access to the individual conducting layers may be provided either by post-growth selective etching or by masking parts of the layers during the crystal growth as depicted in FIG. 8. The exposed conducting layers are contacted by well-established methods in microelectronics.

Thus, as described hereinabove, the artificial receptor of the invention can be configured using any material/substance and method known in the art.

As mentioned, the artificial receptor surfaces of the invention can interact with biological moieties (binding molecules). Such interaction can be monitored by an atomic force microscope (AFM) adapted for force measurements. For example, the antibody or peptide are attached to the AFM tip and substrate, respectively, and the tip deflection is monitored as a function of the separation between the tip and the artificial receptor for different fields applied between the substrate and/or tip and the solution. Since the tip spring constant is measured independently, the deflection can be translated directly to force.

It will be appreciated that the artificial receptor of the invention can specifically bind a biological moiety. As is shown in Table 2 and is described in Example 3 of the Examples section which follows, while the GaAs (100) surface specifically bound the F10 and D3 clones, the GaAs (111A) surface specifically bound the E1, F1, C7 and EB clones. Thus, the predetermined electrostatic field of the GaAs crystal when cut at the 100 plane is different than that formed on the 111A plane and thus, various biological moieties specifically bind to each predetermined electrostatic field.

It will be appreciated that variation of the electrical field as described hereinabove is likely to alter the binding capacity of the surface, thus resulting in different biological moieties attaching thereto.

Thus, the teachings of the invention can be used to gain electrical control over biological processes, namely, to trigger or suppress a selected biological pathway by an electronic signal presented to the system. A given antibody can bind a given set of electrodes biased to a certain voltage pattern and avoid binding to the same electrode set when biased in a different pattern. The latter pattern may, in turn, attract a different antibody. The same set of electrodes biased in different ways thus specifically bind different target molecules from the solution and, hence, act as a programmable artificial receptor.

Thus, the artificial receptor of the invention can be used to provide specific binding for a target moiety (e.g., a biological moiety).

The phrase "specific binding" as used herein, refers to binding of a biological moiety via electrostatic, hydrophobic, hydrogen bonds and van der Waals interactions to an artificial receptor having a surface with unique electrical properties.

As used herein, the phrase "biological moiety" refers to any naturally occurring or synthetic macromolecule having a biological function. Examples include, but are not limited to DNA, RNA, protein, peptide (e.g., antigen, epitope), carbohydrate, antibodies and fragments thereof. It will be appreciated that the biological moiety used by the invention can be isolated or included in a prokaryotic (e.g., bacteria, viruses) or eukaryotic organism (e.g., mammals). Non-limiting examples of biological moieties which can be used along with the invention, include, growth factors, cytokines, transcription repressors, transcriptions enhancers, promoters (e.g., DNA, RNA and/or proteins), and any other molecule which can trigger, suppress, control or regulate any biological process.

The term "antibody" as used in this invention includes intact molecules as well as functional fragments thereof, such as Fab, F(ab')2, Fv or single domain molecules such as VH and VL to an epitope of an antigen. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')$_2$, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; (5) Single chain antibody ("SCA"), a genetically engineered molecule containing the variable region of the light chain and the variable region of the heavy chain, linked by a suitable polypeptide linker as a genetically fused single chain molecule; and (6) Single domain antibodies are composed of a single VH or VL domains which exhibit sufficient affinity to the antigen.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

The term "peptide" as used herein encompasses native peptides (either degradation products, synthetically synthesized peptides, or recombinant peptides), peptidomimetics (typically, synthetically synthesized peptides), and the peptide analogues peptoids and semipeptoids, and may have, for example, modifications rendering the peptides more stable while in a body or more capable of penetrating into cells. Such modifications include, but are not limited to: N-terminus modifications; C-terminus modifications; peptide bond modifications, including but not limited to $CH_2$—NH, $CH_2$—S, $CH_2$—S=O, O=C—NH, $CH_2$—O, $CH_2$—$CH_2$, S=C—NH, CH=CH, and CF=CH; backbone modifications; and residue modifications. Methods for preparing peptidomimetic compounds are well known in the art and are specified, for example, in Ramsden, C. A., ed. (1992), Quantitative Drug Design, Chapter 17.2, F. Choplin Pergamon Press, which is incorporated by reference as if fully set forth herein. Further details in this respect are provided hereinbelow.

The peptides of the invention may be synthesized by any techniques that are known to those skilled in the art of peptide synthesis. For solid phase peptide synthesis, a summary of the many techniques may be found in: Stewart, J. M. and Young, J. D. (1963), "Solid Phase Peptide Synthesis," W. H. Freeman Co. (San Francisco); and Meienhofer, J (1973). "Hormonal Proteins and Peptides," vol. 2, p. 46, Academic Press (New York). For a review of classical solution synthesis, see Schroder, G. and Lupke, K. (1965). The Peptides, vol. 1, Academic Press (New York).

Further description of peptide synthesis is disclosed in U.S. Pat. No. 6,472,505. A preferred method of preparing the peptide compounds of the invention involves solid-phase peptide synthesis, utilizing a solid support. Large-scale peptide synthesis is described by Andersson Biopolymers 2000, 55(3), 227-50.

The DNA or RNA molecules of the invention can be used in the form of oligonucleotide or polynucleotide molecules.

The term "oligonucleotide" refers to a single-stranded or double-stranded oligomer or polymer of ribonucleic acid (RNA) or deoxyribonucleic acid (DNA) or mimetics thereof. This term includes oligonucleotides composed of naturally occurring bases, sugars, and covalent internucleoside linkages (e.g., backbone), as well as oligonucleotides having non-naturally occurring portions, which function similarly to respective naturally occurring portions.

Oligonucleotides designed according to the teachings of the invention can be generated according to any oligonucleotide synthesis method known in the art, such as enzymatic synthesis or solid-phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example: Sambrook, J. and Russell, D. W. (2001), "Molecular Cloning: A Laboratory Manual"; Ausubel, R. M. et al., eds. (1994, 1989), "Current Protocols in Molecular Biology," Volumes I-III, John Wiley & Sons, Baltimore, Md.; Perbal, B. (1988), "A Practical Guide to Molecular Cloning," John Wiley & Sons, New York; and Gait, M. J., ed. (1984), "Oligonucleotide Synthesis"; utilizing solid-phase chemistry, e.g. cyanoethyl phosphoramidite followed by deprotection, desalting, and purification by, for example, an automated trityl-on method or HPLC.

The oligonucleotide of the invention is of at least 5, at least 6, at least 7, at least 8, at least 9, at least 10, at least 11, at least 12, at least 13, at least 14, at least 15, at least 16, at least 17, at least 18, at least 19, at least 20, at least 22, at least 25, at least 30 or at least 40, bases specifically hybridizable with sequence alterations known in the art.

The oligonucleotides of the invention may comprise heterocylic nucleosides consisting of purines and the pyrimidines bases, bonded in a 3'-to-5' phosphodiester linkage.

Oligonucleotides may be modified either in backbone, internucleoside linkages, or bases, using methods known in the art.

For example, the teachings of the invention can be used to identify ligands of specific artificial receptors.

Thus, according to yet another aspect of the invention there is provided a method and a kit for typing ligands.

As used herein, the phrase "typing ligands" refers to identifying ligands, i.e., biological moieties as described hereinabove which are capable of binding a specific surface or region of the artificial receptor of the invention.

"Identifying" according to this aspect of the invention refers to determining the amino acid sequence, nucleic acid sequence, and/or carbohydrate structure of the biological moiety which binds to the artificial receptor of the invention. It will be appreciated when phage display libraries are utilized, determination of the DNA sequence of the clones generating the displayed peptide or protein molecules is preferably effected.

The method is effected by (a) exposing a plurality of biological moieties to the artificial receptor of the invention; and (b) isolating at least one biological moiety of the plurality of biological moieties capable of the specific binding to the artificial receptor, the at least one biological moiety being the ligand capable of specifically binding the artificial receptor; thereby typing the ligands.

Preferably, the method is effected by subjecting the biological moieties (the ligands) to a plurality of surfaces of the artificial receptor of the invention using conventional screening or panning methods which are optimized to fit the artificial receptor of the invention. Thus, the kit for typing ligands further includes reagents (as described hereinbelow) for qualifying binding of the ligands to the plurality of artificial receptors.

Preferably, the method of this aspect of the invention further comprising step (c): exposing the plurality of biological moieties to an additional surface of the artificial receptor, the additional surface having a unique surface electrical properties enabling a specific binding of an additional ligand thereto.

Preferably, step (c) may be effected prior to or following step (a).

It will be appreciated that step (c) is performed in order to increase the specificity of binding to the artificial receptor of the invention. Thus, by exposing the plurality of the biological moieties to an additional surface of the artificial receptor, the non-specific binders of the artificial receptor of the invention (e.g., molecules which bind to the material consisting the receptor and not to the specific electrical property of its surface) are depleted from the plurality of biological moieties exposed to the desired artificial receptor (i.e., the artificial receptor whose ligands are to be typed). A description of such a depletion step is provided under "General Materials and Experimental Methods" and in Examples 1-5 of the Examples section which follows.

Preferably, step (c) is performed at least twice, more preferably, at least three times, more preferably, at least four times, even more preferably, step (c) (i.e., the depletion step) is performed prior to each panning cycle. For depletion (binding to another surface of the artificial receptor), the electrodes of the artificial receptor are preferably switched or biased with a different voltage than provided for the panning. As for the semiconductor surfaces described in Example 1 of the Examples section which follows, no wash step is needed between the depletion step and the subsequent panning step.

Phage display is a powerful technology designed to evolve, from an initial library, peptides and antibody fragments having high affinity to a certain antigen. The most widely used library methodology is based on the filamentous phage, a bacteriophage that infects male *Escherichia coli*. Filamentous phage display is based on cloning DNA fragments encoding millions of variants of certain ligands (e.g. peptides, proteins or fragments thereof) into the phage genome, fused to the gene encoding one of the phage coat proteins (usually pIII, but also pIV, pVI or pVIII). Upon expression, the coat protein fusion is incorporated into new phage particles that are assembled in the periplasmic space of the bacterium. Expression of the gene fusion product and its subsequent incorporation into the mature phage coat results in the ligand being presented on the phage surface, while its genetic material resides within the phage particle. This connection between genotype and phenotype allows the enrichment of specific phage by selection on an immobilized affinity target. The phages are caused to interact with the target antigen while the latter is immobilized. Phages that display a relevant ligand are retained by virtue of their binding to the target, while non-adherent phages are washed away. Bound phages are recovered from the surface, used to re-infect bacteria and reproduced for further enrichment followed by another affinity assay. With an appropriate starting library, several such cycles usually lead to satisfactory selectivity and binding affinity.

Antibodies selected from phage libraries may not be optimal for direct application. In many cases, manipulation of the antibody affinity, valency, specificity, or stability is required. In this case, phage display technology is applied in a manner similar to the production of synthetic libraries and selection of the best binders from them. Such secondary libraries contain variants of the antibodies isolated initially with mutations introduced either randomly or following a rational design. Mutations are introduced into the antibody genes using one of several methods: site-directed mutagenesis, error-prone PCR, chain shuffling, DNA shuffling, or mutator *E. coli* strains. Using one of these approaches it is possible to obtain antibodies having high affinities, (for biological antigens these methods yield affinities well below 100 pM) and good selectivity.

Any method that separates phages that bind from those that do not, can be used for phage selection, and indeed, many different selection methods can be used. The popular selection methods include affinity selection (also called biopanning) on immobilized antigen coated onto solid supports, columns or BIAcore sensor chips.

Antibodies in the form of recombinant antibody fragments were the first proteins to be successfully displayed on the surface of a phage. This was achieved by fusing the coding sequence of the antibody variable (V) regions encoding for a single-chain Fv (scFv) fragment to the amino terminus of the phage gene III, coding for the phage minor coat protein pIII. Initial attempts to display Fab' fragments fused to pVIII, the phage major coat protein, were also successful. However, the pVIII site, although very popular for peptide phage display, is not suitable for the efficient display of large polypeptides such as antibodies. For this reason, most antibody phage-display systems utilize the pIII site.

Antibodies were first displayed using a phage vector, based on the genome of fd-tet and its gene III as fusion partner. In this vector, the genes coding for antibody scFv fragments were cloned in-frame with gene III and downstream of the gene III signal sequence, which normally directs the export of the phage-coat protein to the periplasm. Here, the antibody VH and VL domains may fold correctly, both stabilized by an intramolecular disulfide bridge, and pair to form a functional scFv.

The success of ligand phage display hinges on the synthesis of a large combinatorial repertoire on the phage and efficient selection and enrichment strategies.

Affinity Selection of Initial Library (Biopanning)

For affinity selection, the phage display antibody library is exposed to the artificial receptor or the array of electrodes described hereinabove. The following description refers to one embodiment of the invention. In a first step, antibodies selective to the artificial receptor of the invention such as the structure depicted in FIG. 2d, under a given bias relative to the solution, are selected from the phage display library described hereinabove. For example, the selection preferably contains a collection of molecules each selective to either the A material, the B material, or the A/B interface, all under the given bias. Antibodies specific for either A or B are selected by interacting the same library with pure A or pure B crystals under the same biasing condition. Antibodies selective to the A/B interface are selected by reacting the antibodies selected on the structure depicted in FIG. 2d with pure A and then pure B biased crystals. Specific binding to these crystals depletes the collection from A and B binders, leaving mostly A/B specific binders. More than one selection round may be needed.

It will be appreciated that blocking of non-specific binding to the artificial receptor of the invention can be achieved by incubating the artificial receptor with conventional blocking reagents such as bovine serum albumin, goat serum albumin or milk (e.g., 1%).

In addition, in order to increase the specificity of binding to the artificial receptor of the invention, at least one depletion cycle (as described hereinabove) is effected prior to panning.

Tuning washing times and stringency helps to determine the selection efficiency and to discriminate between phages with different affinities for the target. At times it pays to perform the initial rounds of selection under low stringency, so as not to lose rare binders, and to employ more stringent conditions in later rounds.

Elution of bound phages from the artificial surfaces of the invention can be effected using basic (e.g., TEA at pH 12) or acidic (e.g., Glycine-HCl, at pH 2.2) conditions, depending on the surfaces used (for details see "General Materials and Experimental Methods" of the Examples section which follows). Alternatively, elution of bound phages from the electrifiable electrodes or the biased artificial receptor of the invention can be effected by simply switching the wiring or varying the voltage supplied to the electrodes. Thus, a specific biased surface which specifically binds a ligand can be biased to release such ligand into the solution to thereby elute the desired phage display antibody.

Binding of monoclonal scFv-displaying phage in ELISA can be conventionally detected by primary rabbit anti-M13 antisera in combination with a horseradish peroxidase (HRP) conjugated anti-rabbit antibody. Alternatively, an HRP-anti-M13 conjugate may be used. As is shown in Examples 1 and 2 of the Examples section which follows, the same methods can be used on the artificial receptor surfaces of the invention. Polyclonal phage ELISA on biased A, B, and A/B crystals can be performed to differentiate between specific and non-specific binders as well as for identification and quantification of the various selective binders.

Monoclonal Phage ELISA

To identify monoclonal phage antibodies the phagemids need to be rescued individually. Growth of phagemid containing cells and helper phage rescue is carried out in sterile 96 well, flat bottomed tissue-culture plates, essentially as described under "General Materials and Experimental Methods" of the Examples section which follows. In principle, colonies picked from the last panning cycle are expected to yield the most positive binders. However, it will be appreciated that since in the late cycles the phage population becomes dominated by a few (or even one) binders, clones from the outputs of earliest panning cycles that test positive in the polyclonal phage ELISA are also preferably selected for further analysis.

Production and ELISA Analysis of Soluble scFvs

This test is carried out in parallel with phage ELISAs to analyze individual clones for antigen binding. The phages is infected into HB2151, that does not carry an amber suppressor tRNA and then induced to give soluble expression of antibody fragments for ELISA.

Second Generation Libraries

Antibodies selected from phage libraries may not be optimal for direct application. In many cases, manipulation of the antibody affinity, valency, specificity, or stability is required. In this case, phage display technology is applied in a manner similar to the production of synthetic libraries and selection of the best binders from them. Such secondary libraries contain variants of the antibodies isolated initially with mutations introduced either randomly or following a rational design. Mutations can be introduced here into the antibody genes using one of several methods: site-directed mutagenesis, error-prone PCR, chain shuffling, DNA shuffling, or mutator $E.$ $coli$ strains. Using one of these approaches it should be possible to obtain antibodies having high affinities, (for biological antigens these methods yield affinities well below 100 pM) and good selectivity.

Antibodies for Different Bias Values

The same procedure is applied to the same multi-layer structure biased at different potentials relative to the solution. An optimal antibody for a certain bias might turn an excellent starting point for the generation of a phage display library to be screened by the same interface biased differently. At each bias, antibodies for the A and B crystals as well as for the A/B interface are evolved as described above. The binding regions are sequenced and compared. The sequences displayed by antibodies optimized for different bias values differ from each other. It is extremely interesting to test how large the bias difference should be in order to obtain two different binding regions for two bias values. Strong affinity to a certain bias value is just one aspect of the desired antibodies. The complimentary aspect is selectivity which can be improved by interacting good binders for a certain bias with the same structure biased to a different value. Antibodies that bind also to a different bias can be depleted this way from the library (for further description of depletion steps, see "General Materials and Experimental Methods" of the Examples section which follows).

It will be appreciated that the end result of the screening described hereinabove is a collection of vials, each containing monoclonal antibodies with optimal selectivity to one of the biased surfaces of the artificial receptor of the invention, e.g., the A, B, or A/B structures as described in FIG. 2 or the PLZT crystal described in FIG. 5 when subjected to a given electric field.

Screening of Carbohydrate Ligands Using the Artificial Receptors of the Invention Due to their inherent bond type complexity, synthesizing complex carbohydrate combinatorial libraries necessitates a plurality of distinct synthesis reactions. Carbohydrate libraries can be synthesized employing the "one bead-one molecule" approach, in which the diversity is created by a split-and-pool synthesis or the dynamic combinatorial chemistry (DCC) approach (see for example, Schullek J R, et al., 1997, Anal. Biochem. 246: 20-9; U.S. Pat. Appl. No. 20040146941 to Zhang Biliang et al; Ramstrom O, Lehn J M. Chembiochem. 2000 1: 41-8, which are fully incorporated herein by reference). Such libraries can be screened on the artificial surface of the invention such that the carbohydrate structures interact with a specific surface are identified, isolated and analyzed for composition.

It will be appreciated that the ligands and corresponding artificial receptors can be used in various biological applications. For example, such a ligand and artificial receptor can be used for targeting delivery of a drug molecule.

Thus, according to an additional aspect of the invention there is provided a method of controlling a delivery of a drug molecule or any molecule-of-interest to a tissue of a subject. The method is effected by (a) contacting the tissue with a device body including at least one electrode configured capable of a unique surface electrical property enabling a specific binding of a ligand (e.g., the antibody of the invention) thereto, the ligand being attached to the drug; (b) modifying the unique surface electrical property to thereby control a binding or a release of the ligand and thereby controllably deliver the drug molecule to the tissue.

The term "contacting" encompasses administering, implanting or incubating the artificial receptor with cells, tissues, intracellular space of a subject in need thereof, i.e., a subject, a mammal, a human being, having a pathology requiring the treatment of the drug molecule.

Implanting is effected by surgically or minimally invasively inserting the device body within a human body, e.g., subcutaneously, subdermally, intramuscularly, intraperitoneally, intra brain, and the like.

As used herein the term "ligand" refers to any biological moiety (e.g., polypeptide) which specifically binds to the artificial receptor or an electrode thereof and which can be attached to a molecule-of-interest (e.g., drug). Such a ligand can be, for example, any of the antibodies disclosed herein (e.g., the B7, A3, SR, EB scFv antibodies).

As used herein the phrase "molecule-of-interest" refers to any molecule which delivery thereof to the tissue of a subject is beneficial (e.g., can be used to treat a pathology of a subject). For example, such a molecule can be a drug, a toxic moiety (e.g., which is designed to kill cells), a chemotherapeutic agent (which is designed to kill cancerous cells), a detectable molecule (e.g., an identifiable agent such as biotin, digoxeginin, enzymatic moiety which can be used to detect cells or cellular components), and a radio-isotope (which is capable of labeling and/or killing cells).

As used herein, the term "drug" refers to any substance which can be used to trigger, enhance, suppress, control or regulate any biological process (e.g., cell proliferation, differentiation, expansion, apoptosis, secretion, absorption, transmission and the like). For example, such a drug can be a chemical, a chemotherapeutic drug, an organic molecule, a biological moiety (e.g., which is made of nucleic acids, ribonucleic acids, oligosaccharides, carbohydrates, fatty acids, amino acids), a receptor agonist, an antagonist, a hormone, an antibiotic molecule, an anti-inflammatory agent, a pro-inflammatory agent, a birth control drug, a fertility drug and the like.

Examples of toxins which can be fused to the ligand (e.g., antibody) of the invention include, but are not limited to, enzymatically active toxins of bacterial, fungal, plant, or animal origin, or fragments thereof [e.g., diphteria toxin, exotoxin A chain of *Pseudomonas aeruginosa*, ricin A chain, abrin A chain, modeccin A chain, α-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes].

Examples of radioisotopes which can be fused to the ligand (e.g., antibody) of the invention include, but are not limited to, $^{125}$I, $^{131}$I, $^{90}$Y, $^{212}$Bi, $^{198}$Re, $^{188}$Re, $^{186}$Re, $^{211}$At, $^{67}$Cu, and $^{212}$Pb.

Fusions between the ligand (e.g., antibody) of the invention and the above described molecule-of-interest can be generated using a variety of bifunctional protein-coupling agents, such as N-succinimidyl-3-(2-pyridyldithiol) propionate (SPDP) (e.g., essentially as described in Cumber et al. 1985, Methods of Enzymology 112: 207-224), iminothiolane (IT), bifunctional derivatives of imidoesters (such as dimethyl adipimidate HCL), active esters (such as disuccinimidyl suberate), aldehydes (such as glutareldehyde; essentially as described in G. T. Hermanson, 1996, "Antibody Modification and Conjugation, in Bioconjugate Techniques, Academic Press, San Diego), bisazido compounds (such as bis-(p-azidobenzoyl) hexanediamine), bis-diazonium derivatives (such as bis-(p-diazoniumbenzoyl)-ethylenediamine), diisocyanates (such as tolyene 2,6-diisocyanate), bis-active fluorine compounds (such as 1,5-difluoro-2,4-dinitrobenzene) or carbodiimide conjugation procedure (as described in J. March, Advanced Organic Chemistry: Reaction's, Mechanism, and Structure, pp. 349-50 & 372-74 (3d ed.), 1985; B. Neises et al. 1978, Angew Chem., Int. Ed. Engl. 17:522; A. Hassner et al. Tetrahedron Lett. 4475; E. P. Boden et al. 1986, J. Org. Chem. 50:2394 or and L. J. Mathias 1979, Synthesis 561). For example, a ricin fusion can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the peptide. See WO94/11026; U.S. Pat. No. 6,426,400; Laske, D. W., Youle, R. J., and Oldfield, E. H. (1997) Tumor regression with regional distribution of the targeted toxin TF-CRM107 in patients with malignant brain tumors. Nature Medicine 3:1362-1368.

Additionally or alternatively, when a polypeptide molecules is to be conjugated to the ligand (e.g., antibody) of the invention, recombinant DNA technology can be employed by constructing an expression vector which comprises the coding sequence of the polypeptide molecule (e.g., toxin such as the PE38 KDEL truncated form of pseudomonas exotoxin A) translationally fused to the coding sequence of the ligand of the invention and expressing the construct in a host cell (e.g., a prokaryotic or eukaryotic cell) for the production of a recombinant fusion peptide comprising the amino acids of the toxin and the antibody of the invention.

For example, a drug molecule capable of treating a heart disease is covalently attached to a ligand capable of binding a specific surface (electrical property) of the artificial receptor of the invention. Then, the artificial receptor of the invention is implanted in the subject. For example, the artificial receptor (i.e., the electrode) can be subcutaneously implanted near the heart, similar to a heart pacemaker. Following implantation, the drug molecule is intravenously or orally administered to the subject. However, due to the specific electrical properties configured on the electrode of the artificial receptor of the invention, the drug molecule preferably binds the implanted electrode. A release of the drug molecule is further effected by modifying the unique surface electrical property of the artificial receptor. As a result, the drug molecule is released in situ (i.e., at the site to be treated) and is thus far more efficient in treating the pathology.

The device preferably includes an internal power source and a micro receiver and an acoustic transducer. Modification of the unique surface electrical property can be effected essentially as described in U.S. Pat. No. 6,628,989 to Penner et al., by transmission of one or more external acoustic energy waves or signals from an external source into the subject's body, e.g., generally towards the location of the implanted device until the signal is received by the acoustic transducer. Upon excitation by the acoustic wave(s), the acoustic transducer produces an electrical output configured to generate a voltage capable of modifying the electrical properties of the electrodes in the artificial receptor. It will be appreciated that other types of activation of EM energy can also be used, such as RF, etc.

In one possible application, a variation of the present embodiments is used to provide controlled drug release. A quantity of the drug to be released is held in a reservoir, and in the meantime a molecule for which the artificial receptor has an affinity is released into the bloodstream. The molecule that is released has a magnetic particle attached thereto, thus enabling the attachment of the particle to be sensed at the device. The molecule with the magnetic particle reaches the artificial receptor and binds thereto. The magnetic particle is detected via its magnetic field. Detection of the magnetic particle triggers release of the drug. The reservoirs can be placed with the devices deep inside the body at the points where drug administration is required. The particles can then be systematically administered to control release of the drug at the device. The particles can be used to ensure that a given quantity of the drug is released using timing based say on the half-life of the drug within the body. An example is provided in FIG. 11.

In a further possible application, an endogenous ligand binds to the artificial receptor. Binding of the ligand affects the electric field of the device temporarily and may cause a temporary signal spike which may be detected following suitable noise reduction. The ligand may be selected to be representative of biological activity that it is desired to monitor. For example the ligand may be an antibody, and the presence or level of too many of the antibodies may indicate a certain condition. The condition may be treatable with a given drug which can be part of a controllable release feature as before. An example is provided in FIG. 12.

Thus detection of binding of the given ligand may be used to trigger controlled drug release as in the previous application. Assuming that the drug operates to calm down the condition and reduce the number of the given ligands, a system of negative feedback in fact becomes available for the condition.

It will be appreciated that the artificial receptor of the invention can be also used to identify small molecules capable of mimicking large molecules (e.g., proteins) or cells.

Thus, according to yet an additional aspect of the invention, there is provided a method of identifying a small molecule capable of mimicking a binding function of a ligand.

As used herein, the phrase "binding function" refers to the result of binding of a ligand (e.g., an antibody or any other biological moiety) to the artificial receptor of the invention.

The method is effected by (a) exposing the ligand to at least one electrode configured capable of a unique surface electrical property enabling a specific binding of the ligand thereto, thereby identifying at least one electrode capable of specifically binding the ligand; and (b) identifying a small molecule of a plurality of small molecules capable of binding the at least one electrode being identified as capable of specifically binding the ligand, the small molecule being capable of mimicking the binding function of the ligand.

The method is based on the specific binding of a ligand which is any biological moiety as described hereinabove (e.g., an antibody) to the artificial receptor of the invention (e.g., at least one electrode as described hereinabove). Following the identification of a specific surface or region in the artificial receptor which bind the ligand, the same region or surface is exposed to a plurality of small molecules, e.g., peptides, using for example, a phage display peptide library as described in Example 5 of the Examples section which follows. Thus, a small molecule which specifically binds to the same surface or region as the ligand is capable of mimicking the ligand binding function.

Thus the teachings of the method according to this aspect of the invention can be used to identify the binding domains responsible for interactions between antibodies to foreign intruding antigen molecules, hormones and receptors, proteins capable of binding specific receptors on cancer cells and the like.

For example, a peptide, identified as described hereinabove, which is capable of mimicking the binding of a large protein (e.g., a hormone) to a receptor present on a cancer cell (e.g., estrogen receptor present in breast cancer cells) can be used as a targeting vehicle to deliver a drug molecule to the cancer cells, thus preventing and/or treating the subject having cancer. Briefly, a drug molecule (e.g., an agent capable of preventing cell division) is covalently attached to the peptide mimicking the large protein and is administering to the subject (e.g., using intravenous administration). The peptide is specifically recognized by the receptor on the cancer cells and the drug molecule enters the cancer cell and prevents cell proliferation.

Similarly, peptides mimicking the binding of proteins such as growth factors and cytokines can be used as agents for controlling the proliferation and/or differentiation of cells in vivo (for determination of factor effects), ex vivo (for preparation of cells prior to transplantation in a body) and even in vivo (for direct effect in the body).

It will be appreciated that peptides mimicking proteins which are capable of binding specific cell receptors, such as receptors on heart cells, can be used in facilitating the homing of stem cells to specific cells expressing such receptors. Briefly, the peptides are expressed on ex vivo expanded pluripotent or partially committed progenitor cells using an expression vector and known molecular biology techniques. The ex vivo expanded cells are then transplanted in a recipient subject and the peptide, which is displayed on the transplanted cell membrane as part of a cellular receptor is likely to home to heart cells which present the specific electric field generated by the artificial receptor used in the identification of such a peptide.

Once specific antibodies or peptides with appropriate specificity and affinity are generated, such antibodies or peptides can be engineered to contain a fused moiety that triggers or suppresses a biochemical or biological reaction.

To demonstrate triggering of a biochemical reaction, chimeric proteins are preferably prepared by fusing an enzyme such as peroxidase or alkaline phosphatase to the recombinant antibody and expressing such a construct in E. coli. Alternatively, the antibody is engineered with a specific peptide tag at the C-terminus for site specific biotinylation which enables further manipulation through biotin-streptavidin interaction. To demonstrate activation of a biological process the selected antibodies are fused with antigens capable of triggering different immune responses. Alternatively they are fused with a DNA binding protein and used to affect in-vitro gene expression.

It will be appreciated that the artificial receptor of the invention can be can be used to characterize a binding site of a ligand. Briefly, such characterization can be achieved by first exposing the ligand to a plurality or an array of electrodes of the artificial receptor of the invention and isolating and electrically characterizing at least one electrode exhibiting specific binding to the ligand.

As used herein the phrase "electrically characterizing" refers to determining the electric field generated by a surface of the at least one electrode. Such an electric field can be characterized in terms of field strength and/or field shape or spatial distribution on or above the surface (two dimensional or three dimensional).

Altogether, in contrast to a conventional (chemical or biological) receptor, the electronic or artificial receptor of the invention can be reconfigured in real time to select a desired molecule out of a certain collection. Since each of the antibodies can be fused to an additional molecule having a certain biological function, elution of the bound molecules after rinsing all other molecules may be designed to trigger a desired process corresponding uniquely to the original electrode biasing pattern. Alternatively, binding of selected antibodies to the electrodes removes these molecules from the solution and blocks their corresponding biological processes. The invention thus takes the interface between manmade electronics and molecular biology a giant leap forward. The teachings of the invention can be used to facilitate activation or suppression of specific biological pathways based on electronically programmable signals.

Thus, according to an additional aspect of the invention there is provided a method of activating or suppressing a biological pathway in cells of a subject. The method is effected by: (a) contacting the cells of the subject with a device body including at least one electrode configured capable of a unique surface electrical property enabling a specific binding of a ligand or the antibody of the invention thereto, the ligand, the antibody or a molecule-of-interest attached thereto being capable of activating or suppressing the biological pathway; (b) modifying the unique surface electrical property to thereby control a binding or a release of the ligand or the antibody and thereby controllably activating or suppressing the biological pathway in the cells of the subject.

Preferably, modifying is effected using a remote switching unit as described hereinabove.

It will be appreciated that the ligand can be an endogenous molecule (present in the cells of the subject) or can be an exogenous molecule which is further administered to the subject.

The implications of such an interface are far reaching. At one end of the spectrum it can be harnessed to electrically control biological processes. For instance, the fused segments may comprise antigens that activate a certain immune response or gene expression. One may envision sensors that probe several biological parameters and feed these signals into electronics that processes the data and activates the required biological pathway using the proposed artificial receptor. The ease of computation by electronic logic provides unparalleled flexibility compared with pure biology alternatives. Moreover, since electronic signals can be generated in the electrodes in response to an electronically transmitted signal, the proposed approach also facilitates remote activation of biological processes. At the other end of the spectrum the scheme provides a promising strategy for closing feedback loops from electronic functionality of biologically constructed nanoelectronics to the construction process itself. To clarify the latter point consider the efforts in recent years to harness molecular biology for the self-assembly of molecular scale electronics. DNA molecules and related proteins were used to scaffold the assembly of a functional transistor made out of non-biological ingredients. Once the transistor was made, there was no way to test its electronic functionality in situ and feedback to the biological assembly process. Without such feedback it is hard to imagine self-assembly of significantly more complex circuits. Feedback from electronic functionality to the assembly process is hence the bottleneck for large scale integration.

The presently preferred embodiments add a new dimension to the interface between nano-electronics and biology and may dramatically affect both fields. The electrode device of FIGS. 2a-d embodies an artificial receptor whose target antibodies can be changed in real time. Such flexibility is unmatched in biology. Further fascinating possibilities are associated with the potential of electrical control over the bound antibody activity and the extent of control over the bound protein activity which can be achieved by bias of the electrical properties of the artificial receptor of the present invention.

While further reducing invention to practice, the present inventors have uncovered specific antibodies capable of binding the artificial receptor of the invention which comprises gold (e.g., the SR scFv antibody) or a hydroquinone (e.g., the 12A scFv antibody).

Thus, according to yet another aspect of the invention there is provided an antibody comprising an antigen binding domain which comprises complementarity determining regions (CDRs) as set forth by SEQ ID NOs:99-104 (e.g., the 12A scFv described in Example 7 of the Examples section which follows).

According to yet additional aspect of the invention there is provided an antibody comprising an antigen binding domain which comprises complementarity determining regions (CDRs) as set forth by SEQ ID NOs:87-92 (e.g., the SR antibody described in Example 6 of the Examples section which follows).

As is shown in the Examples section which follows, the present inventors have uncovered that while the 12A antibody binds to the artificial receptor which comprises a hydroquinone monolayer with a specific binding activity (see ELISA results in Table 10, Examples 7 and 8 of the Examples section which follows and FIG. 20), such an antibody is incapable of binding the artificial receptor of the invention following the application of electrical pulses which change the unique electrical surface of the receptor and consequently, the conformation of hydroquinone to benzoquinone (FIGS. 17, 20 and 21 and Example 8 of the Examples section which follows). These results suggest the use of such antibodies (e.g., the 12A scFv) as a ligand used for controlled delivery of a drug to a tissue.

Thus, according to yet another aspect of the invention, there is provided a system for controllable delivery of a molecule-of-interest to a tissue, comprising: (i) the molecule-of-interest conjugated to the antibody of the invention (e.g., the 12A antibody) and (ii) an artificial receptor which comprises a surface having an extent, the surface comprises a hydroquinone and a switching functionality for controllably modifying unique electrical properties of the surface; wherein the antigen binding domain of the antibody is capable of binding the surface.

The hydroquinone may be conjugated directly or indirectly (e.g., via gold) to the artificial receptor or electrodes thereof (see the Examples section which follows).

Thus, there is provided a method of controlling a delivery of a molecule-of-interest to a tissue of a subject. The method is effected by (a) contacting the tissue of the subject with the system of the invention a subject in need thereof, and (b) modifying the unique electrical properties of the surface to thereby control a binding or a release of the antibody from the artificial receptor, thereby controlling the delivery of the molecule-of-interest to the tissue.

It will be appreciated that for implantation into a subject the system may include or be coated with biocompatible and/or non-immunogenic components.

Systems and antibodies of some embodiments of the present invention may be configured as or in microfluidics devices. Microfluidics has emerged as a revolutionizing technology for a "lab-on-a-chip" with numerous applications. The perspectives have recently been described in a series of review articles [see for example, Craighead, H. Future lab-on-a-chip technologies for interrogating individual molecules. Nature 442, 387-393 (2006); deMello, A. J. Control and detection of chemical reactions in microfluidic systems. Nature 442, 394-402 (2006); El-Ali, J., Sorger, P. K. & Jensen, K. F. Cells on chips. Nature 442, 403-411 (2006); Janasek, D., Franzke, J. & Manz, A. Scaling and the design of miniaturized chemical-analysis systems. Nature 442, 374-380 (2006); Psaltis, D., Quake, S. R. & Yang, C. H. Developing optofluidic technology through the fusion of microfluidics and optics. Nature 442, 381-386 (2006); Whitesides, G. M. The origins and the future of microfluidics. Nature 442, 368-373 (2006); Yager, P. et al. Microfluidic diagnostic technologies for global public health. Nature 442, 412-418 (2006), each of which is fully incorporated herein by reference].

It is expected that during the life of this patent many relevant switching devices and field carrying materials will be developed and the scopes of the corresponding terms herein are intended to include all such new technologies a priori.

As used herein the term "about" refers to ±10%.

Additional objects, advantages, and novel features of the invention will become apparent to one ordinarily skilled in the art upon examination of the following examples, which are not intended to be limiting. Additionally, each of the various embodiments and aspects of the invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., Ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (Eds.) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes 1-111 Cellis, J. E., Ed. (1994); "Culture of Animal Cells—A Manual of Basic Technique" by Freshney, Wiley-Liss, N.Y. (1994), Third Edition; "Current Protocols in Immunology" Volumes 1-111 Coligan J. E., Ed. (1994); Stites et al. (Eds.), "Basic and Clinical Immunology" (8th Edition), Appleton & Lange, Norwalk, Conn. (1994); Mishell and Shiigi (Eds.), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., Ed. (1984); "Nucleic Acid Hybridization" Hames, B. D., and Higgins S. J., Eds. (1985); "Transcription and Translation" Hames, B. D., and Higgins S. J., Eds. (1984); "Animal Cell Culture" Freshney, R. I., Ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Semiconductor crystals—Galium Arsenite (GaAs) (American Xtal technology Cat. No. 5129327) or silicone (Wacker chmitronic GMBH) crystals, were cut through two planes: The 100 plane which is parallel to one of the surface plane of the crystal and the 111 plane of the crystal. The semiconductor crystals used were: silicon (100), GaAs (100), GaAs (111A) and GaAs (111B). The crystals at the 100 plane were round with a diameter of about 5 cm; The crystals at the 111 plane were triangles. The width of all crystal wafers was 0.5 mm, regardless of its plane.

For panning (i.e., selecting for antibodies or peptides which bind the semiconductor surface), each crystal disc of the 100 crystals was cut into a square of 1×1 cm$^2$ and each of the 111 crystals was cut to a 1 cm long triangle. The four rounds of panning were performed in Eppendorf tubes using a 360° C. tube rotator (Labquake Labotal).

For the ELISA assay, the crystal wafers were cut into small squares which fit the 96-well ELISA plate.

Selection of antibody molecules against specific crystal facets of semiconductor—A human phage display library, Ronit 1, was used for the selection. The library was constructed by Ronit Azriel and Itai Benhar from the faculty of life sciences at Tel Aviv University, Israel (kindly provided by Prof. Itai Benhar) and contains 1×10$^9$ independent scFv clones [Azriel-Rosenfeld, R., Valensi, M.& Benhar, I., A human synthetic combinatorial library of arrayable single-chain antibodies based on shuffling in vivo formed CDRs into general framework regions, JMB 335, 177-192, (2003)]. The library is composed of different human synthetic single chain Fv fragments, with variable VH and VL genes in the CDR3 region and is known to generate specific binders to a host of biological targets. The RONIT 1 library consists of a principal in which in vivo formed complementarity determining regions were shuffled combinatorially onto germline-derived human variable-region frameworks. The arraying of library-derived scFvs is facilitated by a unique display/expression system, where scFvs are expressed as fusion proteins with a cellulose-binding domain. This library was screened against a number of peptides, proteins, and peptide-protein complexes and yielded antibody fragments exhibiting dissociation constants in the low nanomolar range.

In principle, the selection protocol was similar to that used for selecting biological targets (e.g., as described for the antibodies against the scMHC-peptide complexes) as detailed in Denkberg G., et al., 2002; The J. of Immunology 169: 4399-4407, except that some optimization was performed to adjust for the semiconductor surfaces.

Optimization of the Scanning Conditions for the Semiconductor Surfaces

Crystal specific pH elution conditions—For the GaAs (100) and GaAs (111A), elution was superior in basic conditions (e.g., TEA at pH 12) rather than acidic conditions. On the other hand, for the silicone crystals (both 100 and 111), elution was performed under acidic conditions (e.g., Glycine-HCl, at pH 2.2).

Blocking of non-specific binding to semiconductor surfaces—GaAs substrates [GaAs (111A), (111B), (100)] showed extensive non-specific binding of the phages to the substrate via their coat proteins. Although the binding energy per protein was small, their excess number when compared to the number of expressed antibodies dominated the panning assay. To reduce the non-specific binding, the semiconductor surfaces were blocked for 1 hour at room temperature in Tris-buffered saline (TBS), 1% milk and then rinsed six times in TBS to wash excess milk.

Depletion cycles—In order to isolate specific binders for specific semiconductor surfaces, the phage display library was exposed to one type of surface [e.g., GaAs (111)] prior to being exposed to another surface [e.g., GaAs (100)], thus the clones capable of binding the first surface [e.g., GaAs (111)] were depleted from the library. It is worth mentioning that no wash step was performed between the depletion step [e.g., panning on the GaAs (111)] and the following panning step [e.g., panning on the GaAs (100)].

Selection of Phage-Antibodies—naïve library—Bound phages were eluted from surfaces using TEA at pH 12 [for GaAs (100) and GaAs (111A)] or Glycine-HCl, at pH 2.2 (for the silicone crystals). Eluted phages were used to infect TG1 E. coli cells (at $OD_{600\ nm}$=0.5) for 60 minutes at 37° C., following which the infected bacteria were plated on 2YT plates containing 100 µg/ml ampicilin (2YT/A/G) and 1% glucose (Sigma G5767).

Panning—The semiconductor substrates were exposed to the Ronit1 library (which includes about 50% of the M13KO7) or to M13KO7 helper phage (devoid of scFv, as a control experiment) in TBS, 1% milk. After rocking for 1 hour at room temperature, the surfaces were washed 10 times with TBS, 0.1% TWEEN-20.

Elution—The phages were eluted from the surfaces by adding tri-ethyl amine (pH 12, 0.1M) for 10 minutes, transferred to a fresh tube and then neutralized with Tris (HCl) (pH 7).

Quantification—The eluted phages were titrated in dilution series on solid agar and colonies were counted to estimate the number of adsorbed phages. Briefly, for each panning step colonies from bound phages were collected from the 2YT/A/G plates and diluted 1:100 in 25 ml of 2YT/A/G medium. Cells were grown to $O.D_{600\ nm}$=0.5 and M13KO7 helper phage [5×10$^{11}$ colony forming unit (cfu)] was added to 25 ml of the culture. After incubation for 60 minutes at 37° C., the cells were centrifuged, resuspended in 25 ml of 2YT/Ampicillin (100 µg/ml)/Kanamycin (50 µg/ml) and grown overnight at 30° C. Phages were collected from culture supernatants and purified for the next round of panning by PEG precipitation. This procedure repeated 4 times. The diversity of the selected antibodies was determined by DNA fingerprinting (using restriction enzymes such as BstNI). Non-specific binding was estimated by titrating the Kanamycin resistant M13KO7 helper phages on Kanamycin plates.

Rescue of phages from individual colonies—To rescue phage, single ampicillin-resistant colonies resulting from infection of TG1 bacteria with phages, were inoculated into 100 µl of 2×TY containing 100 µg/ml Ampicillin and 1% glucose (2×TY-Amp-glucose) in 96-well plates and grown overnight at 37° C. Five to twenty microlitters of the overnight cultures were inoculated into 150 µl fresh 2×TY-Amp, to an $OD_{600}$ nm=0.5 (about 1.5-2 hours). The M13KO7 helper phage [25 µl of 2×TY-Amp-glucose containing $10^9$ plaque forming unit (p.f.u.)] was then added to each well, and the plate was incubated without agitation for 60 minutes at 37° C. The plate was then shaken at 37° C. for one hour after which the cells were pelletted at 4000 rpm for 15 minutes. The cells were then resuspended in 200 µl 2×TY containing 100 µg/ml Amp and 25 µg/ml Kan (2×TY-Amp-Kan) and grown overnight at 30° C. The cells were pelletted as above, and the supernatants containing the phages (monoclonal scFv-displaying phages) were tested for their binding to the semiconductor surface using the ELISA assay.

ELISA conditions of monoclonal scFv-displaying phages on semiconductor surfaces—For ELISA assay, the semiconductor surfaces [GaAs (111A) and GaAs (100)] were cut into small squares of 4×4 mm to fit the 96-well ELISA plate, incubated for 60 minutes with 4% milk in TBS, and washed 6 times with TBS (200 µl each wash). In each well, about 60 µl of a monoclonal phage suspension (isolated following 4 panning as described above) was mixed with TBS to reach a final volume of 150 µl/well. The reaction (between the monoclonal scFv-displaying phages and the semiconductor surfaces) was incubated for one hour at room temperature while shaking. To remove unbound monoclonal scFv-displaying phages, the fluid was aspirated, and the wells including the semiconductor surfaces were washed 6 times in TBS containing 0.1% of Tween-20. To reveal antibody-bound surfaces, an anti M13 monoclonal antibody conjugate (Amersham 27-9421-01) (which is capable of specifically binding to the monoclonal scFv-displaying M13 phages) was added (0.125 µl per well), incubated for 1 hour in the presence of 1% milk, following which the wells were washed 6 times with TBS and the TMB One Step Substrate (S-159985 DAKO Cytomation, Denmark) was added. The ELISA reactions were read at 450 nm. The DNA of positive phage clones (i.e., phage clones displaying OD values of 0.750 or higher in the ELISA assay) was further characterized by BstNI restriction analysis and/or sequencing.

Expression and purification of soluble scFv antibodies—The scFv gene is rescued from the phage clone by PCR and is then subcloned into the phagemid vector pCANTAB6 by using the SfiI-NotI cloning sites. A Myc and hexahistidine tags are fused to the C-terminus of the scFv gene. The scFv antibody is expressed in BL21 λDE3 cells and purified from the periplasmic fraction by metal-ion affinity chromatography:

Soluble ScFv are purified from the periplasmic fraction of BL21 cells using the hexahistidine tag. An overnight starter culture of Fab specific clones is grown at 30° C. Bacterial cells are diluted 1:100 into 500 ml of 2YT/A/G, grown to $OD_{600\ nm}$=0.8-1.0 and induced to express the recombinant ScFv antibody by the addition of 1 mM IPTG for 3 hours at 30° C. The bacterial cells are centrifuged and the pellet is resuspended in 5 ml of a B-PER solution (Pierce) to release periplasmatic content. After 30 minutes of rotated incubation at room temperature, the solution is centrifuged (15000 rpm, 15 minutes) and the supernatant is incubated with 0.5 ml of pre-washed TALON beads suspension (Clontech) for 45 minutes at room temperature. The solution is applied onto a BioRad (Hercules, Calif.) disposable column, and after sedimentation the beads are washed three times with 10 ml of PBS/0.1% Tween 20 (pH 8.0). The bound ScFvs are eluted using 0.5 ml of 100 mM Imidazole in PBS. To remove residual imidazole, the eluted scFv are dialyzed twice against PBS (overnight, 4° C.). The homogeneity and purity of the purified ScFv/Fabs is determined by analysis on non-reduced and reduced SDS-PAGE.

ELISA assay of soluble scFv antibodies on semiconductor surfaces—4×4 mm squares of GaAs (111A) and GaAs (100) were placed in a 96 well ELISA plate with 4% milk for 60 minutes and then washed 6 times with PBS. The soluble scFv antibodies were then added in PBS containing 2% milk, and allowed to complex with the surface. Unbound soluble scFv antibodies were washed away and labeled secondary anti human HRP (Goat anti Human IgG F(ab)$_2$—HRP; Jackson ImmunoResearch Laboratories. Inc. Cat. No. 109035097) were added to the wells. Binding of the scFv to the substrates was quantified by reaction with TMB calorimetric substrate.

GaAs etching—GaAs (100) was etched in $H_3PO_4:H_2O_2$: $H_2O$ 1:13.8:13.2 mixture in a −12° C. bath for 30 minutes.

Panning of semiconductor surfaces with a phage display peptide library—The Ph.D.-7 Phage Display Peptide Library Kit (New England Bio Labs Inc., Beverly, Mass., USA) was used to screen for positive phages displaying peptides capable of binding to the following semiconductor surfaces: GaAs (100), and GaAs (111A). The panning protocol was exactly as recommended by the kit's manufacturer except that panning was performed on crystal surfaces as described hereinabove for panning of scFv phages.

Preparation of gold substrates—Gold substrates were prepared by vacuum deposition of titanium (50° A) and subsequent gold (500° A) onto silicon (100) wafers.

Preparation of Hydroquinone (HQ) and Benzoquinone (BQ) Monolayer—Gold substrates were prepared by vacuum deposition of titanium (50° A) and subsequent gold (500° A) onto silicon (100) wafers. Clean gold-coated silicon substrates were further immersed for 18 hours at room temperature in ethanolic solutions of a Hydroquinone-terminated alkanethiol and a methyl-terminated alkanethiol, in 1:10 ratios. After incubation, the gold electrode was washed for 15 minutes in ethanol and 15 minutes in PBS. Cyclic voltammetry was used to determine the density of hydroquinone groups in the monolayer. Integration of the voltammetric wave for reduction of the Hydroquinone show that the density of Hydroquinone groups is $2.5 \times 10^{14}$ molecule/$cm^2$.

Panning of Hydroquinone (HQ) and Benzoquinone (BQ) monolayer coated surfaces—For panning (i.e., selecting for antibodies or peptides which bind the monolayer surface), the Gold wafer with the HQ monolayer on him was cut into a square of 1×1 $cm^2$. The four rounds of panning were performed in Eppendorf tubes using a 360° C. tube rotator (Labquake Labotal), essentially as described hereinabove.

For the ELISA assay, the crystal wafers were cut into small squares which fit the 96-well ELISA plate.

Example 1

A Depletion Step Prevents Non-Specific Binding of Phages to Semiconductors

Studies by Whaley, S. R., (2000, Supra), have shown that phage display peptides bind GaAs (100) preferentially to GaAs (111A) and (111B). However, when one of these peptides was later synthesized and applied to GaAs, no selectivity was found between the (100) and (110) facets [Goede, K., 2004 (Supra)]. To test the reasons for such a discrepancy the present inventors have studied the non-specific binding of M13 phages, carrying no peptides or antibodies, to GaAs (100), GaAs (111A) and GaAs (111B), as follows.

Experimental Results

Binding of helper phage to semi conductors—Phages and the GaAs substrates were interacted and following panning and elution the density of phages was estimated from a count of colonies on agar plates. As is shown in FIG. 13, in the absence of a depletion step the non-specific binding of the M13KO7 helper phage is higher on GaAs (100) as compared to GaAs (111A). Thus, these results demonstrate that the M13 phage preferentially binds to the GaAs (100) facet through its coat protein. Since these phages are identical to the library phages used in Whaley et al., [Whaley, 2000 (Supra)] and given the lack of selectivity displayed by the only free peptide tested so far Goede, K., et al. [Goede, 2004 (Supra)], these results may explain the false binding specificity obtained when phage display peptides were applied to the GaAs facets [Whaley, 2000 (Supra)].

Thus, these results demonstrate that a panning protocol which includes a depletion step can be used to prevent non-specific binding of phages to a semiconductor facet, similar to the depletion step used in other screening methods. In addition, these results may suggest that experiments with free peptides are needed in order to confirm or disprove semiconductor facet recognition by short peptides.

Example 2

Enrichment of scFv Binders Depends on Panning Cycles and Depletion Steps

To test the possibility that a human antibody library (e.g., scFv library) contains binders with preferred selectivity to a specific surface of a seminconductor such as GaAs, the present inventors have performed several cycles of panning and counted the number of phages eluted following each panning step, as follows.

Experimental Results

Selection of scFv binders to GaAs (111A)—To select scFv phage binders to GaAs (111A), about $10^{11}$ phages (~100 copies of each library clone) were applied to the semiconductor crystal (the panning step). After washing the unbound phages, the bound ones were recovered by rinsing the sample in an alkaline solution. The recovered phages were then quantified by infecting bacteria and plating dilution series on Petri dishes. The amplified sub-library was applied again to the target crystal facet and so on. It typically took three to four panning rounds to isolate excellent binders to the target. As evident from FIG. 15, the number of bound phages retrieved from the semiconductor grew 300 fold when panning was repeated three times. For comparison, the non-specific binding of identical phages (M13) carrying no scFv fragments remained low throughout the selection process. Interestingly, as shown in FIG. 13, in the absence of blocking against non-specific binding [a step missing in Whaley, S. R., (2000, Supra)], the non-specific binding of phages through their coat protein to GaAs (100) was larger than to GaAs (111A). FIG. 15 thus proves selection of increasingly better binders to GaAs (111A), yet, it provides no indication of selectivity with respect to GaAs (100). Indeed, as indicated by the columns 1 and 2 of FIG. 9, application of the polyclonal population of binders selected on GaAs (111A) to GaAs (100) shows similar binding to the latter crystalline facet.

A depletion step enables selective binding of antibodies to semiconductor facets—Preferential binding to a given crystalline facet was achieved by a slight modification of the process which includes a depletion step. Thus, the phages recovered from the first panning on GaAs (111A) were amplified in *E. coli* bacteria and subsequently applied to GaAs (100). The unbound phages [which were not bound to GaAs (100)] were collected and applied in a second panning step to GaAs (111A).

Table 1, hereinbelow, summarizes the panning results.

TABLE 1

Enrichment of binders to GaAs (100), GaAs (111A) and Silicon vs. panning round

| Panning round | GaAs 100 (phage/ml) | | GaAs 111A (phage/ml) | | Silicon (phage/ml) |
|---|---|---|---|---|---|
| | With depletion on GaAs (111A) | Without depletion on GaAs (111A) | With depletion on GaAs (100) | Without depletion on GaAs (100) | |
| 1 | $3 * 10^5$ | $3 * 10^5$ | $3 * 10^4$ | $3 * 10^4$ | $6. * 10^4$ |
| 2 | $1 * 10^5$ | $6 * 10^3$ | $3 * 10^6$ | $1 * 10^4$ | $7. * 10^6$ |
| 3 | $1 * 10^7$ | $2 * 10^6$ | $9 * 10^6$ | $1 * 10^6$ | $1. * 10^8$ |

Table 1: The No. of phage clones eluted at each panning round is presented. Note the effect of a depletion panning on the selectivity of binding to a specific surface.

Depletion cycles on a certain semiconductor facet increased binding affinity of phage display antibodies towards the other facet—As is shown in Table 1, hereinabove, at the second and third rounds of panning, the selectivity of binding to the GaAs (111A) surface increased by about an order of magnitude following depletion steps over the GaAs (100) surface. Similarly, at the second and third rounds of panning on the GaAs (100) surface, the selectivity of binding to the GaAs (100) surface increased by an order of magnitude following depletion steps on the GaAs (111A) surface.

In addition, when the pool of the phage display antibodies was depleted by panning on cycle 2 and 3 on the GaAs (100) surface, the phage display antibodies selected following the forth panning on the GaAs (111) exhibited a significant higher binding efficacy towards the GaAs (111) surface than towards the GaAs (100) surface. As evident from the results presented in FIG. 9, following two depletion steps on GaAs (100) the number of phage clones (i.e., the binders in this case) which bind GaAs (111A) increases (compare column 3 to column 1 in FIG. 9), while the number of phage clones which bind to the GaAs (100) facet decreases (compare column 4 to column 2 in FIG. 9). Binding of the selected phages to the (111A) facet was this time almost 100 times higher than to the (100) facet. This discrimination is as high as the maximal discrimination of a short peptide between very different materials (Goede, K. et al., 2004).

Thus, these results demonstrate that a significant increase in binders to a specific GaAs facet can be achieved by increasing the panning cycle and including at least one depletion step between the panning cycles.

Altogether, these unexpected results demonstrate that phage display antibodies which specifically bind to semiconductor surfaces (i.e., binders) can be isolated, preferably following one or two depletion cycles. Thus, specific binders to the GaAs (111A) were isolated following 2 depletions on the GaAs (100) surface.

Example 3

Binding of Monoclonal scFv Phages to Semiconductor Facets

The polyclonal population of selected phages contains different scFv fragments, each characterized by different affinity and selectivity to the two crystalline facets. To correlate specificity with a specific amino acid sequence, the binding selectivity of individual clones was analyzed. Monoclonal binders were isolated by infecting *E. coli* bacteria with the sub-library and plating them on solid agar. Since each bacterium can be infected by a single phage, all bacteria in a given colony carry DNA coding for the same scFv fragment. Infection of the colony with helper phages resulted in release of phages displaying the same scFv on their PIII coat proteins. The isolated monoclonal phages were then analyzed by ELISA against GaAs (111A) and (100), as follows.

Experimental Results

ELISA analysis confirmed selectivity of phage display antibodies to the semiconductor surfaces—After 4 rounds of panning and 2 rounds of depletion, several clones (monoclonal scFv-displaying phages) were subject to an ELISA assay. About 60% of the clones showed markedly enhanced binding to their target compared to the control group. The readings for the monoclonal scFv-displaying phages are summarized in Table 2, hereinbelow.

TABLE 2

ELISA analysis of selected phage display antibodies

| Clone | GaAS 111A | GaAS 100 |
|---|---|---|
| E1 | 0.984 | 0.204 |
| F1 | 0.849 | 0.234 |
| F10 | 0.142 | 0.890 |
| B7 | 1.236 | 0.942 |
| C7 | 0.826 | 0.206 |
| E11 | 0.939 | 1.385 |
| D11 | 0.570 | 0.426 |
| A3 | 0.314 | 0.187 |
| D3 | 0.205 | 0.809 |

Table 2: Shown are ELISA readings of scFv monoclonal phages measured at 450 nm in 96-well plates.

The ELISA results for a soluble scFv antibody of clone EB (which was found in another scFv phage library) are presented in FIG. 16. The background ELISA signal, depicted by bars 7-9, accounts for most of the GaAs (100) signal in columns 1-6. Subtraction of this background from columns 1-6 demonstrated a remarkable preference to GaAs (111A) compared with (100). Interestingly, the binding of the secondary antibody to GaAs (100) is almost twice as large compared with its binding to GaAs (111A), just opposite to the selectivity of the isolated scFv fragments.

Altogether, clones E1, F1, C7 and EB were selective to GaAs (111A), clones F10 and D3 were selective to GaAs (100), and clones B7, E11, D11 and A3 bind GaAs (111A) and (100) equally well.

To further confirm the specificity of binding to the surface, the DNA of all ten clones (including EB) was sequenced for the $V_H$ CDR3 and $V_L$ CDR3 genes. Table 3, hereinbelow, presents the sequences of the $V_L$ and $V_H$ CDR3 genes of the isolated clones.

TABLE 3

CDR3 of the light and heavy chains of scFv phage clones

| $V_L$ CDR3 | SEQ ID NO: | $V_H$ CDR3 | SEQ ID NO: | Clone |
|---|---|---|---|---|
| QQYGNSPHT | 1 | GGLGKRGADCPDY | 11 | c7 |
| NSRDSSGNRVV | 2 | DRTAGYFDY | 12 | b7 |
| QTSDSRLDA | 3 | DEGTF | 13 | e1 |
| QSYDSRLSA | 4 | REKIGCGGDCLDL | 14 | f1 |
| QAWDSDT | 5 | RRRGATAFDY | 15 | f10 |
| QSYDSNDYVF | 6 | DRANSGGWFGGDS | 16 | e11 |
| QQSYSTPW | 7 | GTSGWYGIDY | 17 | d11 |
| QQSYSAPP | 8 | ADDLWIDNHPPNHYSFDS | 18 | a3 |
| QQYGRSPTGG | 9 | PREMNATYPFDS | 19 | d3 |
| NSRDSSGNHVV | 10 | RRYALDY | 20 | EB |

Table 3: Presented are the CDR3 of the light ($V_L$ CDR3) (SEQ ID NOs: 1-10) and heavy ($V_H$ CDR3) (SEQ ID NOs: 11-20) chains of 10 scFv phage clones. The nature of the presented amino acids is as follows: P (cyclic amino acid residues); Y, W and F (aromatic amino acid residues); S, N, T, Q and C (polar uncharged amino acid residues); G, V, A, L, I and M (non-polar aliphatic amino acid residues); D and E (negatively charged amino acid residues) and H, R and K (positively charged amino acid residues).

The sequences of CDR1 and 2 can be found in Table 4, hereinbelow.

Table 4

CDR1 and CDR2 of the light and heavy chains of scFv phage clones

| | | SEQ ID NO: | |
|---|---|---|---|
| $V_H$ CDR1 | A3 | 41 | LSSYDLS |
| | c7 | 42 | FTVNSNYMN |
| | d11 | 43 | RQAPGKGLE |
| | e11 | 44 | TSDDHAMH |
| | f10 | 45 | DDYAMS |
| | b7 | 46 | RRYGMH |
| | d3 | 47 | RQAPGKGLE |
| | e1 | 48 | TDYYMS |
| | f1 | 49 | SSSALQ |
| | EB | 50 | DDYGMS |
| $V_H$ CDR2 | A3 | 51 | RINGDGSSTSYADSVKG |
| | c7 | 52 | IETNGITSYADSVKG |
| | d11 | 53 | AISAGGDAPWYAGSARG |
| | e11 | 54 | RINSDGSSTIYADSAKG |
| | f10 | 55 | AISGSGGTTYYADSVKG |
| | b7 | 56 | AITTGGGSPNYADSVKG |
| | d3 | 57 | GISGSGGSTNYADSVKG |
| | e1 | 58 | YINPSSRYTDYADSVKG |
| | f1 | 59 | YVSPGSDDTYYADSVKG |
| | EB | 60 | GINWNGGSTGYADSVKG |
| $V_L$ CDR1 | A3 | 21 | RASQSVSSNLA |
| | c7 | 22 | HPSP |
| | d11 | 23 | RASQTVSSRYLA |
| | e11 | 24 | GSNSNIGSNTVN |
| | f10 | 25 | SGSTSNIAANTVH |
| | b7 | 26 | GSSSNIGSNTVN |
| | d3 | 27 | RASQSVRSNYLA |
| | e1 | 28 | GSSPNIGSNTVK |
| | f1 | 29 | GSSSNIGSNTVN |
| | EB | 30 | QGDSLRSYYAS |
| $V_L$ CDRW | A3 | 31 | DASIRATGIP |
| | c7 | 32 | GASTRATGIP |
| | d11 | 33 | DASSRAPGIP |
| | e11 | 34 | GVTNRPS |
| | f10 | 35 | SNNQRPS |
| | b7 | 36 | RDNQRPS |
| | d3 | 37 | DASKRAPGIP |
| | e1 | 38 | DNNQRPS |

Table 4-continued

CDR1 and CDR2 of the light and heavy chains of scFv phage clones

| | SEQ ID NO: | |
|---|---|---|
| f1 | 39 | DNYKRPSGVPD |
| EB | 40 | GKNNRP |

Table 4: Presented are the CDR1 and 2 of the light ($V_L$ CDR1-SEQ ID NOs: 21-30; $V_L$ CDR2-SEQ ID NOs: 31-40) and heavy ($V_H$ CDR1-SEQ ID NOs: 41-50; $V_H$ CDR2-SEQ ID NO: 51-60) chains of 10 scFv phage clones. The nature of the presented amino acids is as follows: P (cyclic amino acid residues); Y, W and F (aromatic amino acid residues); S, N, T, Q and C (polar uncharged amino acid residues); G, V, A, L, I and M (non-polar aliphatic amino acid residues); D, N and E (negatively charged amino acid residues) and H, R and K (positively charged amino acid residues).

Monoclonal binders of semiconductor facets share sequence homology—The sequences of CDR1, 2, and 3 of the monoclonal scFv-displaying phages was obtained and is presented in Tables 3 and 4, hereinabove. It should be noted, that although the EB clone is derived from another library, the sequence of the $V_H$ CDR3 of this clone (the EB clone) shares similarities with the same region in the Ronit1 library clones. The sequence of the EB $V_L$ CDR3 is identical, except a single amino acid, to the $V_L$ of b7. Inspection of the sequences reveals significant similarities between the different clones, some of which can be traced to conserved amino acids in the library. However, other similarities are attributed to the selection process itself, most notably; the abundance of positively charged amino acids in the $V_H$ CDR3 is twice as high compared with the frequency of such residues at those positions in a random sample of library clones. Out of 47 clones sampled randomly from the library, only one $V_H$ contained a positively charged amino acid in the first position and only eleven displayed such an amino acid in the second position. The 10 selected binders, on the other hand, contained three positively charged amino acids in the first position and five in the second position. The sequences presented in Table 3, hereinabove, were further compared to those of scFv selected on gold [the SR scFv (screened on gold, SEQ ID NOs:87-89 for CDRs 1, 2 and 3, respectively, of the $V_L$, and SEQ ID NOs:90-92 for CDRs 1, 2 and 3, respectively, of the $V_H$; the B7 scFv (screened on GaAs, also binds to gold, SEQ ID NOs:93-95 for CDRs 1, 2 and 3, respectively, of the $V_L$, and SEQ ID NOs: 96-98 for CDRs 1, 2 and 3, respectively, of the $V_H$) in Example 6, hereinbelow]. The abundance of positively charged amino acids in CDR3 $V_H$, CDR1 $V_H$, CDR1 $V_L$ of the latter was less than half compared with the former and no negatively charged amino acid was found in the first six positions of CDR3 $V_L$. Those were replaced by polar uncharged amino acids, predominantly serine. The comparison with the library and anti-gold scFv sequences thus indicates the importance of positively charged amino acids in positions 1-3 of CDR3$V_H$ and the negatively charged amino acids in CDR3$V_L$ for binding GaAs.

Altogether, in contrast to Whaley et al., [Whaley, 2000 (Supra)] the antibody used in the present study was also tested and found selective to crystal orientation when detached from the phage (i.e., as a soluble scFv antibody).

Using phage display technology the present inventors demonstrate in vitro isolation of scFv that bind GaAs (111A) facets almost hundred times better than GaAs (100). Thus, the findings presented here demonstrate the remarkable selectivity of antibodies to the very simple structure of semiconductors compared with bio-molecules. More generally, these findings imply that antibody molecules may find application in the assembly of nanoelectronics (Keren, K. et. al., 2002; Keren, K., et al., 2003; Braun, E., et al., 1998), in producing templates for localizing nanoparticles (Seeman, N. C., 2003), or for biosensors (Mirkin, C. A., et al., 1996).

Example 4

Soluble scFv Antibodies can Differentially Bind to Specific Facets of GaAs Semiconductor Crystals The present inventors have tested the capability of the soluble EB scFv antibodies isolated from the monoclonal EB scFv-phage clone to discriminate between different crystalline facets of a GaAs semiconductor crystal, an almost flat target, unfamiliar to the immune system, as follows.
Experimental Results Binding of soluble scFv antibodies to the semiconductors facets—Using conventional photolithography and $H_3PO_4$: $H_2O_2$:$H_2O$ etch, a long trench has been defined on a GaAs (100) substrate in the (110) direction (FIG. 14a). Due to the slow etching rate of phosphoric acid in the (111A) direction, the process leads to slanted (111A) side walls and a flat (100) trench floor (FIG. 14a). FIG. 14b depicts a SEM image of a cut across the trench, proving the slanted walls are indeed tilted in the (111A) direction [54.7 degrees relative to the (100) direction]. When the isolated soluble scFv antibodies (of clone EB) are applied to the GaAs substrate they selectively attach to the (111A) slopes. To image the bound antibody molecules they were targeted with anti-human secondary antibodies conjugated to a fluorescent dye, Alexa Fluor. As seen in FIG. 14c, fluorescence is limited solely to the (111A) slopes with practically no background signal coming from the (100) surfaces. Control experiments depleted of the scFv fragments exclude possible artifacts such as natural fluorescence of the (111A) facets, selective binding of the fluorescent dye or secondary antibodies to that facet, etc.

Altogether, the results presented in FIGS. 9 and 15 which correspond to scFv fragments displayed on phage particles demonstrate specific binding on phage display scFv antibodies to specific facets of the GaAs semiconductor. For practical applications, such as the one demonstrated in FIGS. 14a-c, it is desired to have soluble monoclonal scFv fragments detached from the phage coat proteins.

Thus, the results presented in FIGS. 14a-c prove that the selected soluble scFv antibody molecules recognize and bind selectively GaAs (111A) as opposed to GaAs (100). In addition, these results suggest the use of the labeled antibodies to localize practically any microscopic object on (111A) surfaces with negligible attachment to other crystalline facets.

Example 5

Selection of Phage Display Peptides which Bind to Semiconductor Surfaces

Prior studies applied specific crystal facets of metals, oxides, minerals, and semiconductors for the selective binding of peptides. The present inventors screen a phage display peptide library for selective binders of the GaAs (100) and GaAs (111A) surfaces, as follows.

It should be noted that in contrast to the panning process performed by Whaley, 2000 (Supra), which did not include a depletion step, the panning process employed to screen for phage display peptides included at least one depletion step as described under "General Materials and Experimental Methods", hereinabove.
Experimental Results Selection of peptides against specific crystal facets of semiconductors—The New England Biolabs random peptide library is an exhaustive collection of linear heptapeptide (1.28×10⁹ different peptides). The randomized peptide sequences are expressed at the N-terminus of the minor coat protein pIII, resulting in a valency of 5 copies of the displayed peptide per virion.

The GaAs (100) and GaAs (111A) were screened using the Ph.D-7 phage display peptide library using 4 rounds of panning. FIG. 10 depicts the enrichment of binders to GaAs (100) and GaAs (111A) vs. panning round.

Clones selected following panning on the GaAs 100 surface—Clones were sequenced after each panning cycle on the GaAs (100) crystal. As seen in Tables 5, 6, and 7, hereinbelow, the third panning round (Table 7) produced 10 identical clones (which an amino acid sequence as set forth in SEQ ID NO:86) and another subset of two identical clones. Hence, the binding of other peptides to GaAs (100) must be significantly less efficient.

TABLE 5

Clones from panning 1 on GaAs 100 surface

| | SEQ ID NO: | |
|---|---|---|
| GGGSSSTSHRSHS | 61 | Out1_100-4_02 |
| GGGMQTYTNSSHS | 62 | Out1_100-5_04 |

Table 5: Presented are the amino acid sequences of the specific peptides displayed on the phage clones isolated following a first panning cycle on GaAs (100). Out1_100-4_02 (SEQ ID NO: 61); Out1_100-5_04 (SEQ ID NO: 62).

TABLE 6

Clones from panning 2 on GaAs 100 surface

| | SEQ ID NO: | |
|---|---|---|
| GGGRSVQLTLSHS | 63 | Out2_100-6_09 |
| GGGSRAQTYASHS | 64 | Out2_100-1_16 |
| GGGPSEALHWSHS | 65 | Out2_100-3_03 |
| GGGFLQSTIHSHS | 66 | Out2_100-2_01 |
| GGGRLNHEHSSHS | 67 | Out2_100-5_07 |

Table 6: Presented are the amino acid sequences of the specific peptides displayed on the phage clones isolated following a second panning cycle on GaAs (100). Out2_100-6_09 (SEQ ID NO: 63); Out2_100-1_16 (SEQ ID NO: 64); Out2_100-3_03 (SEQ ID NO: 65); Out2_100-2_01 (SEQ ID NO: 66); Out2_100-5_07 (SEQ ID NO: 67).

TABLE 7

Clones from panning 3 on GaAs 100 surface

| | SEQ ID NO: | |
|---|---|---|
| GGGYTYMAPLSHS | 86 | 10 identical clones |
| GGGSRKLPMYSHS | 68 | Out3_100-4_10 |
| GGGSRKLPMYSHS | 69 | Out3_100-1_04 |
| GGGDPWEITTSHS | 70 | Out3_100-3_08 |
| GGGLLTTTTGSHS | 71 | Out3_100-6_14 |

Table 7: Presented are the amino acid sequences of the specific peptides displayed on the phage clones isolated following a third panning cycle on GaAs (100). The sequence of the 10 identical clones is set forth by SEQ ID N0: 86; Out3_100-4_10 (SEQ ID NO: 68); Out3_100-1_04 (SEQ ID NO: 69); Out3_100-3_08 (SEQ ID NO: 70); Out3_100-6_14 (SEQ ID NO: 71).

Clones selected following panning on the GaAs 111A surface—Clones were sequenced after each panning cycle on the GaAs (111) crystal. As seen in Tables 8 and 9, hereinbelow, the sequences selected to GaAs (111) show a clear consensus sequence.

TABLE 8

Clones from panning 3 on GaAs 111A surface

| GGGLPPPTYTSHS | Out3_111_1 |
|---|---|
| GGGDSIPSHVSHS | Out3_111_2 |
| GGGPSSEYQWSHS | Out3_111_3 |
| VSLPSVA | Out3_111_4 |
| GGGTIITHHQSHS | Out3_111_5 |
| GGGTIITHHQSHS | Out3_111_6 |
| GGGTIITHHQSHS | Out3_111_7 |
| GGGIPWSHPDSHS | Out3_111_8 |
| GGGIPWSHPDSHS | Out3_111_9 |

Table 8: Presented are the amino acid sequences of the specific peptides displayed on the phage clones isolated following a third panning cycle on GaAs (111A). Out3_111_1 (SEQ ID NO: 72); Out3_111_2 (SEQ ID NO: 73); Out3_111_3 (SEQ ID NO: 74); Out3_111_4 (SEQ ID NO: 75); Out3_111_5 (SEQ ID NO: 76); Out3_111_6 (SEQ ID NO: 77); Out3_111_7 (SEQ ID NO: 78); Out3_111_8 (SEQ ID NO: 79); Out3_111_9 (SEQ ID NO: 80).

TABLE 9

Clones from panning 4 on GaAs 111A surface

| GGGPLHRPTHSHS | Out4_111A-1 |
|---|---|
| GGGTAWLPTWSHS | Out4_111A-2 |
| GGGRQLELQASHS | Out4_111A-3 |
| GGGRFDHQATSHS | Out4_111A-4 |
| GGGAMPQRPLSHS | Out4_111A-5 |

Table 9: Presented are the amino acid sequences of the specific peptides displayed on the phage clones isolated following a forth panning cycle on GaAs (111A). Out4_111A-1 (SEQ ID NO: 81); Out4_111A-2 (SEQ ID NO: 82); Out4_111A-3 (SEQ ID NO: 83); Out4_111A-4 (SEQ ID NO: 84); Out4_111A-5 (SEQ ID NO: 85).

These results clearly demonstrate that both the GaAs 111A and GaAs 100 surfaces are capable of selectively binding specific phage display peptides sharing a consensus sequence.

Example 6

Screening for Binders to a Gold Surface

The SR scFv was isolated by screening for scFv antibodies (binders) on a gold substrate as described under "General Materials and Experimental Methods". Following are the CDRs of the $V_L$ and $V_H$ of the SR scFv.

$V_L$ CDRs
CDR1-SSYVLH            (SEQ ID NO: 87)
CDR2-GISGSGATAYYADSVKG (SEQ ID NO: 88)
CDR3-NDGGGLLDF         (SEQ ID NO: 89)

$V_H$ CDRs
CDR1-GSNSIGNNSVN       (SEQ ID NO: 90)
CDR2-RNTNRPS           (SEQ ID NO: 91)
CDR3-SSYASNRDVLF       (SEQ ID NO: 92)

The B7 scFv was isolated by screening for binders on GaAs 100 surface, also binds to gold. Following are the CDRs of the $V_L$ and $V_H$ of the SR scFv.

```
V_H CDRs
CDR1-RRYGMH                    (SEQ ID NO: 93)
CDR2-AITTGGGSPNYADSVKGR        (SEQ ID NO: 94)
CDR3-DRTAGYFDY                 (SEQ ID NO: 95)

V_L CDRs
CDR1 GSSSNIGSNTVN              (SEQ ID NO: 96)
CDR2 RDNQRPS                   (SEQ ID NO: 97)
CDR3 NSRDSSGNRVVFGG            (SEQ ID NO: 98)
```

Example 7

Selection of an Antibody to a Hydroquinone (HQ) Monolayer

Experimental Results

Modulation of the oxidation state of the HQ to BQ by electrical control—Although the preferred state of the molecule is HQ, the monolayer can be electrically converted to its benzoquinone form as seen in FIG. 17.

Isolation of scFv antibodies which specifically bind to an electrically controlled monolayer—A monoclonal scFv-displaying phage was isolated after 4 rounds of panning and the scFv-displaying phage was subjected to an ELISA assay.

ELISA analysis confirmed selectivity of phage display antibodies to the monolayer surfaces—ELISA assay confirmed the specificity of the scFv-displaying phage to the HQ monolayer. The readings for the monoclonal scFv-displaying phage are summarized in Table 10, hereinbelow.

TABLE 10

| ELISA analysis of selected phage display antibodies | | |
|---|---|---|
| Clone | Hydroquinone monolayer on Gold | Gold |
| 12A | 0.593 | 0.291 |

Table 10: Shown are ELISA readings of the 12A scFv monoclonal phage measured at 450 nm in 96-well plates.

To further confirm the specificity of binding to the surface, the $V_H$ and $V_L$ genes of the 12A clone DNA were sequenced.

Following are the CDRs of the $V_H$ and $V_L$ genes of clone 12A scFv, which is specific to the HQ-monolayer.

```
V_H CDRs of clone 12A
CDR1 TTYNMNW                   (SEQ ID NO: 99)
CDR2 RINTDGSNTGYADSVKG         (SEQ ID NO: 100)
CDR3 DFFGRRGAYFYSGMDV          (SEQ ID NO: 101)

V_L CDRs of clone 12A
CDR1 NVNSNLA                   (SEQ ID NO: 102)
CDR2 GASSRATGIP                (SEQ ID NO: 103)
CDR3 QHRGTFGG                  (SEQ ID NO: 104)
```

Example 8

The Chip Design

The original chip consists of a prism on which two continuous polycrystalline layers are evaporated. The first is a 10 nm thick chromium layer; the second is a 50 nm thick gold layer. The chromium acts as wetting layer that improves the stability of the gold layer on top of it. The chip's area is 22 mm×22 mm. The monitoring is performed on a 16 mm² area at the center of the chip. In this region, a solution containing the absorbed material flows in six parallel channels on the face of the chip. This configuration is achieved in the following way. A room temperature vulcutation (RTV) casting of six channels [micro channel module (MCM)] is attached tightly to the chip. Each channel is 450 μm in width and 100 μm in height. The casting is shown in FIGS. 18*a-b*.

Each channel is connected through the RTV casting to a 160 μm—diameter hose at one terminal and a 10 μm diameter hose at the other. The solution flows from the thick hose to the thin hose. FIGS. 19*a-d* depict this configuration. Along each channel, there are six 300 μm² spots on the surface of the chip which are being monitored. These spots are called Area Of Interest (AOI). In total, there are 36 AOIs.

In order to carry out the electrical measurements, the continuous layer on the chip was divided to three isolated areas. The first is the working electrode on which the adsorption and desorption is monitored; the second is a counter electrode and the third is the reference electrode. The separation to three electrodes is achieved in the following way. An RTV casting, similar to that of the surface plasmon resonance (SPR) instrument, is attached tightly to the chip. Then, four 160 μm—diameter hoses are connected to each terminal of the first and third channels. To these hoses, a gold etching solution followed by a chrome etching solution are injected. These solutions are pumped through the hoses to the RTV channels and exit through the hoses at the other side. When flowing on top of the chip, the solutions etch the gold and chromium layers and thus form two slits. The distance between the slits is approximately 1 mm. This defines the width of the reference electrode. The separation into three electrodes is completed by extending the slits to the edge of the chip with a scriber. The middle electrode on the chip is then modified into an Ag/AgCl reference electrode. This is done by silver electroplating followed by electrolytic oxidation. The electroplating is performed by exposing the center of the middle electrode to an AgNO₃ solution and applying −10 mA with respect to a platinum electrode for 20 seconds. The oxidation is accomplished by immersing the chip in an HCl solution and applying 20 V with respect to a platinum electrode for 30 seconds. The resultant is a modified chip that consists of three insulated electrodes as depicted in FIGS. 19*a-d*.

Like the chip itself, the monitored area is divided to three parts. The working electrode covers approximately one half of the area. The counter and reference electrode covers the other half. Originally, every channel contained 6 AOI's. In electrochemical—SPR experiments were the modified chip is used, however, only half of the AOI's are inspected since only 18 AOI's out of the 36 are placed on the working electrode. As there is no interest in monitoring absorption on the other two electrodes, the AOI's covering them are ignored. The data presented, therefore, consists of six channels each with only 3 AOI's.

Experimental Setup

The experimental setup consists of the SPR containing the modified chip, and the electrochemical system. The wiring of the chip is done by connecting the working counter and reference electrodes on the chip to their corresponding terminals on the electrochemical system using. The sense terminal is short circuited to the working electrode. The data collected in these experiments come from both the SPR and the electrochemical system. Like every SPR experiment, the absorption of material on the chip is monitored and presented as a plot of response unit (R.U.) vs. time. Data from every channel is presented separately. The electrochemical system is set to the chronoamperometric mode. The data obtained from this mode is current vs. time. Unlike the SPR, this instrument does not distinguish between various regions on the working electrode, that is, it is not possible to monitor the current from each AOI. For this reason, data obtained from the electrochemical system is less important. It is mainly used as an accurate function generator. Prior to the experiment the modified chip is sonicated in double distilled water (DDW) and ethanol for 10 minutes each. The wiring of the chip to the electrochemical instrumentation is done through a copper board. At one end it has the three terminals that connect the parastat, the other end is connected to three 0.5 mm wires attached the three electrodes on the chip. Attaching the wires to the chip is done in the following way. A small amount of silver paint is spread from the edge of the three electrodes of the gold layer to one of the perpendicular faces of the chip. Than, the 0.5 mm wires are connected to the three silver spreading using a copper tape. The connection is done on the perpendicular face and not on the gold layer itself. A regular tape is than applied to cover the perpendicular face to strengthen the electrical connections. Finally, the chip is placed in the SPR instrument and the parastat terminals are connected to the copper board.

Result-On Chip with HQ Monolayer

The binding of the 12A antibody is specific to the HQ monolayer on the chip—The binding of the soluble 12A scFv antibody to the HQ monolayer was determined using SPR. Briefly, the four binding channels were injected at t=0 seconds with the soluble 12A scFv antibody solution, in PBS pH 7.2. At t=230 seconds, antibody injection was terminated and a decline had set when pure PBS buffer pH 7.2 was injected instead. As seen in FIG. 20, after the washing (with PBS) the antibodies remained bound to the hydroquinone monolayer.

Lack of binding of the 12A antibody to the BQ monolayer—As is further shown in FIG. 21, following application of potential pulses of +0.6 V (for 30 seconds), the HQ monolayer changed conformation into the BQ monolayer. Antibody injected to the BQ monolayer failed to bind the BQ monolayer on the chip.

These results conclusively show that the 12A antibody is specific to the HQ monolayer and not to the BQ monolayer and demonstrate the generation of antibodies which can bind to or release from the chip monolayer by the application of electrical control.

Analysis and Discussion

Phage display is a powerful technology designed to isolate from an initial library peptides or antibody fragments having high affinity to a certain antigen. The most widely used library methodology is based on the filamentous phage M13 (Smith, G. P., 1985), a bacteriophage infecting male *Escherichia coli*. Filamentous phage display is based on cloning DNA fragments encoding billions of variants of certain ligands into the phage genome, fused to the gene encoding one of the phage coat proteins. Expression of the gene fusion product and its subsequent incorporation into the mature phage coat, results in the ligand being presented on the phage surface, while its genetic material resides within the phage particle.

The Ronit1 scFv antibody phage library Azriel-Rosenfeld, R., et al., 2003), used in the present study, is a phagemid library comprising $2 \times 10^9$ different human semi-synthetic single chain Fv fragments, where in vivo formed complementarity determining regions (CDR loops) were shuffled combinatorially onto germline-derived human variable region framework regions of the heavy ($V_H$) and light ($V_L$) domains.

Little is known on the interaction between bio-molecules and inorganic surfaces, let alone recognition of such surfaces by antibody molecules. The GaAs surface is modified by surface reconstruction, oxidation, and possibly other chemical reactions. Moreover, it displays atomic steps and possibly surface defects. It is therefore difficult to estimate how much of the underlying crystalline order manifests itself in the recognition process. Unfortunately, no experimental tools capable of determining these parameters with atomic resolution exist for the moment. The recognition mechanism is hence unclear except the indications for the importance of structural rigidity discussed in the introduction. The discrimination between the two crystalline facets may reflect the different underlying crystalline structure, may stem from the different surface chemistry of the two facets or may result from global properties such as atom density and different electro-negativity. The latter factor has been found to be important for the differential binding of specific peptides to different semiconductors (Goede, K., 2004). The unusually high abundance of positively charged amino acids in the heavy chain of CDR1 and CDR3 and the light chain of CDR1 may indicate affinity to the exposed Gallium atoms. The negatively charged amino acid in $CDR3V_L$ (missing in anti-gold scFv isolated from the same library) combined with the positively charged $CDR3V_H$ may match the polar nature of GaAs. may also be provided separately or in any suitable subcombination.

The 7 and 12 mer peptides used in most in vitro selection of binders to inorganic crystals are typically too short to assume a stable structure. Antibodies on the other hand, display a rigid 3D structure which is potentially essential for high affinity selective binding (Perl-Treves, D., et al., 1996; Bromberg, R., et al., 1998). Moreover, the recognition site in the latter case involves six amino acid sequences grouped in three complementarity determining regions (CDR). Altogether these CDRs form a large, structured binding site spanning 3×3 nm.

On a more fundamental level it should be noted that the remarkable selectivity reported here may hint to the importance of a rigid 3D structure for surface selectivity.

Another hint to the importance of rigidity for facet recognition is provided by the rigid structure characterizing antifreeze peptides that target specific ice facets (Knight C. A., et al., 1991). It has also been shown that the stable helical structure of a 31 mer peptide catalyzing calcite crystallization is essential for inducing directed crystal growth along a preferred axis (DeOliviera D. B. and Laursen R. A., 1997), possibly due to its differential binding to the various facets. Structure rigidity may thus turn central to facet recognition by biomolecules, underscoring the importance of antibody libraries as a promising source for selective binders.

Selective binding to specific crystalline facets can be directly utilized for numerous micro and nanotechnological applications including positioning of nanocrystals at a well defined orientation, governing crystal growth and forcing it to certain directions, and positioning nanometer scale objects at specific sites on a substrate marked by certain crystalline facets. An application of one of the soluble antibodies identified by the present study to the latter task is demonstrated in FIGS. 14a-c.

In summary, the remarkable variety of binding sequences produced by the immune system, as represented in a semi-synthetic antibody library displayed on the surface of phages, were shown to include single chain Fv discriminating between different facets of the same semiconductor. This finding generates an intimate interface between manmade materials and biology. Beyond applications to the positioning of nanometer scale objects at desired sites or direction of crystal growth, the effect of semiconductor binding on the antibody may be harnessed to trigger biological processes, similar to those resulting from binding of biological antigens.

In that respect, antibody binding is biologically more accessible than peptide binding. Imagine for instance the task of localizing a semiconductor nanocrystal at a given site. In a free running process confirmation of such assembly is practically impossible. However, the triggering of a certain biological process by the binding of the nanocrystal to the antibody may be engineered to signal successful assembly and even trigger the next assembly step.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the invention.

What is claimed is:

1. An isolated antibody comprising an antigen binding domain which comprises complementarity determining regions (CDRs) as set forth by SEQ ID NOs:99-101 for CDRs 1-3, respectively of the heavy chain, and SEQ SEQ ID NOs: 102-104 for CDRs 1-3, respectively of the light chain.

2. A system for controllable delivery of a molecule-of-interest to a tissue comprising:

(i) the molecule-of-interest conjugated to the antibody of claim 1, and;

(ii) an artificial receptor which comprises a surface having an extent, said surface comprises a hydroquinone and a switching functionality for controllably modifying electrical properties of said surface, wherein said antigen binding domain of said antibody is capable of binding said hydroquinone, and wherein said switching functionality controls a binding or a release of said antibody from said hydroquinone.

3. The system of claim 2, configured for implantation in a subject in need thereof.

4. A method of controlling a delivery of a molecule-of-interest to a tissue of a subject, comprising:

(a) contacting the system of claim 2 with the tissue of the subject, and;

(b) modifying said electrical properties of said surface to thereby control a binding or a release of said antibody from said artificial receptor;

thereby controlling the delivery of the molecule-of-interest to the tissue.

5. The method of claim 4, wherein the molecule-of-interest is selected from the group consisting of a drug, a toxin and a detectable moiety.

6. The method of claim 4, wherein said modifying said electrical properties of said surface is effected using a remote switching unit.

7. The method of claim 4, wherein said hydroquinone comprises a hydroquinone monolayer.

8. The method of claim 4, wherein said surface further comprises gold, and whereas said hydroquinone is attached to said surface by conjugating to said gold.

9. The method of claim 4, wherein modification of said electrical properties of said surface results in a conformation change of said hydroquinone to a benzoquinone and whereas said antibody is incapable of binding said surface following said modification.

10. The method of claim 4, wherein said switching functionality is obtained by carbon nanotubes and/or silicone nanowires.

11. The method of claim 4, wherein said artificial receptor further comprises a laminate including a plurality of independently electrifiable layers, said surface being formed from a cross-section of said laminate.

12. The method of claim 11, wherein said switching functionality comprises a selector for selecting a voltage level for each of said independently electrifiable layers, to thereby allow change in an electrical field of said surface.

13. A system comprising:

(i) the antibody of claim 1, and;

(ii) a surface comprising hydroquinone;

wherein the antibody is capable of binding said hydroquinone.

* * * * *

SEQUENCE LISTING

```
<160> NUMBER OF SEQ ID NOS: 104

<210> SEQ ID NO 1
<211> LENGTH: 9
<212> TYPE: PRT
<213> ORGANISM: Artificial sequence
<220> FEATURE:
<223> OTHER INFORMATION: C7 ScFv VL CDR3

<400> SEQUENCE: 1

Gln Gln Tyr Gly Asn Ser Pro His Thr
1               5

<210> SEQ ID NO 2
<211> LENGTH: 11
<212> TYPE: PRT
<213> ORGANISM: Artificial sequence
<220> FEATURE:
<223> OTHER INFORMATION: B7 ScFv VL CDR3

<400> SEQUENCE: 2

Asn Ser Arg Asp Ser Ser Gly Asn Arg Val Val
1               5                   10

<210> SEQ ID NO 3
<211> LENGTH: 9
<212> TYPE: PRT
<213> ORGANISM: Artificial sequence
<220> FEATURE:
<223> OTHER INFORMATION: E1 ScFv VL CDR3

<400> SEQUENCE: 3

Gln Thr Ser Asp Ser Arg Leu Asp Ala
1               5

<210> SEQ ID NO 4
<211> LENGTH: 9
<212> TYPE: PRT
<213> ORGANISM: Artificial sequence
<220> FEATURE:
<223> OTHER INFORMATION: F1 ScFv VL CDR3

<400> SEQUENCE: 4

Gln Ser Tyr Asp Ser Arg Leu Ser Ala
1               5

<210> SEQ ID NO 5
<211> LENGTH: 7
```

```
<212> TYPE: PRT
<213> ORGANISM: Artificial sequence
<220> FEATURE:
<223> OTHER INFORMATION: F10 ScFv VL CDR3

<400> SEQUENCE: 5

Gln Ala Trp Asp Ser Asp Thr
1               5

<210> SEQ ID NO 6
<211> LENGTH: 10
<212> TYPE: PRT
<213> ORGANISM: Artificial sequence
<220> FEATURE:
<223> OTHER INFORMATION: E11 ScFv VL CDR3

<400> SEQUENCE: 6

Gln Ser Tyr Asp Ser Asn Asp Tyr Val Phe
1               5                   10

<210> SEQ ID NO 7
<211> LENGTH: 8
<212> TYPE: PRT
<213> ORGANISM: Artificial sequence
<220> FEATURE:
<223> OTHER INFORMATION: D11 ScFv VL CDR3

<400> SEQUENCE: 7

Gln Gln Ser Tyr Ser Thr Pro Trp
1               5

<210> SEQ ID NO 8
<211> LENGTH: 8
<212> TYPE: PRT
<213> ORGANISM: Artificial sequence
<220> FEATURE:
<223> OTHER INFORMATION: A3 ScFv VL CDR3

<400> SEQUENCE: 8

Gln Gln Ser Tyr Ser Ala Pro Pro
1               5

<210> SEQ ID NO 9
<211> LENGTH: 10
<212> TYPE: PRT
<213> ORGANISM: Artificial sequence
<220> FEATURE:
<223> OTHER INFORMATION: D3 ScFv VL CDR3

<400> SEQUENCE: 9

Gln Gln Tyr Gly Arg Ser Pro Thr Gly Gly
1               5                   10

<210> SEQ ID NO 10
<211> LENGTH: 11
<212> TYPE: PRT
<213> ORGANISM: Artificial sequence
<220> FEATURE:
<223> OTHER INFORMATION: EB ScFv VL CDR3

<400> SEQUENCE: 10

Asn Ser Arg Asp Ser Ser Gly Asn His Val Val
1               5                   10

<210> SEQ ID NO 11
<211> LENGTH: 13
<212> TYPE: PRT
<213> ORGANISM: Artificial sequence
```

```
<220> FEATURE:
<223> OTHER INFORMATION: C7 ScFv VH CDR3

<400> SEQUENCE: 11

Gly Gly Leu Gly Lys Arg Gly Ala Asp Cys Pro Asp Tyr
1               5                   10

<210> SEQ ID NO 12
<211> LENGTH: 9
<212> TYPE: PRT
<213> ORGANISM: Artificial sequence
<220> FEATURE:
<223> OTHER INFORMATION: B7 ScFv VH CDR3

<400> SEQUENCE: 12

Asp Arg Thr Ala Gly Tyr Phe Asp Tyr
1               5

<210> SEQ ID NO 13
<211> LENGTH: 5
<212> TYPE: PRT
<213> ORGANISM: Artificial sequence
<220> FEATURE:
<223> OTHER INFORMATION: E1 ScFv VH CDR3

<400> SEQUENCE: 13

Asp Glu Gly Thr Phe
1               5

<210> SEQ ID NO 14
<211> LENGTH: 13
<212> TYPE: PRT
<213> ORGANISM: Artificial sequence
<220> FEATURE:
<223> OTHER INFORMATION: F1 ScFv VH CDR3

<400> SEQUENCE: 14

Arg Glu Lys Ile Gly Cys Gly Gly Asp Cys Leu Asp Leu
1               5                   10

<210> SEQ ID NO 15
<211> LENGTH: 10
<212> TYPE: PRT
<213> ORGANISM: Artificial sequence
<220> FEATURE:
<223> OTHER INFORMATION: F10 ScFv VH CDR3

<400> SEQUENCE: 15

Arg Arg Arg Gly Ala Thr Ala Phe Asp Tyr
1               5                   10

<210> SEQ ID NO 16
<211> LENGTH: 13
<212> TYPE: PRT
<213> ORGANISM: Artificial sequence
<220> FEATURE:
<223> OTHER INFORMATION: E11 ScFv VH CDR3

<400> SEQUENCE: 16

Asp Arg Ala Asn Ser Gly Gly Trp Phe Gly Gly Asp Ser
1               5                   10

<210> SEQ ID NO 17
<211> LENGTH: 10
<212> TYPE: PRT
<213> ORGANISM: Artificial sequence
<220> FEATURE:
<223> OTHER INFORMATION: D11 ScFv VH CDR3
```

-continued

<400> SEQUENCE: 17

Gly Thr Ser Gly Trp Tyr Gly Ile Asp Tyr
1               5                   10

<210> SEQ ID NO 18
<211> LENGTH: 18
<212> TYPE: PRT
<213> ORGANISM: Artificial sequence
<220> FEATURE:
<223> OTHER INFORMATION: A3 ScFv VH CDR3

<400> SEQUENCE: 18

Ala Asp Asp Leu Trp Ile Asp Asn His Pro Pro Asn His Tyr Ser Phe
1               5                   10                  15

Asp Ser

<210> SEQ ID NO 19
<211> LENGTH: 12
<212> TYPE: PRT
<213> ORGANISM: Artificial sequence
<220> FEATURE:
<223> OTHER INFORMATION: D3 ScFv VH CDR3

<400> SEQUENCE: 19

Pro Arg Glu Met Asn Ala Thr Tyr Pro Phe Asp Ser
1               5                   10

<210> SEQ ID NO 20
<211> LENGTH: 7
<212> TYPE: PRT
<213> ORGANISM: Artificial sequence
<220> FEATURE:
<223> OTHER INFORMATION: EB ScFv VH CDR3

<400> SEQUENCE: 20

Arg Arg Tyr Ala Leu Asp Tyr
1               5

<210> SEQ ID NO 21
<211> LENGTH: 11
<212> TYPE: PRT
<213> ORGANISM: Artificial sequence
<220> FEATURE:
<223> OTHER INFORMATION: A3 ScFv VL CDR1

<400> SEQUENCE: 21

Arg Ala Ser Gln Ser Val Ser Ser Asn Leu Ala
1               5                   10

<210> SEQ ID NO 22
<211> LENGTH: 4
<212> TYPE: PRT
<213> ORGANISM: Artificial sequence
<220> FEATURE:
<223> OTHER INFORMATION: C7 ScFv VL CDR1

<400> SEQUENCE: 22

His Pro Ser Pro
1

<210> SEQ ID NO 23
<211> LENGTH: 12
<212> TYPE: PRT
<213> ORGANISM: Artificial sequence
<220> FEATURE:
<223> OTHER INFORMATION: D11 ScFv VL CDR1

-continued

<400> SEQUENCE: 23

Arg Ala Ser Gln Thr Val Ser Ser Arg Tyr Leu Ala
1               5                   10

<210> SEQ ID NO 24
<211> LENGTH: 12
<212> TYPE: PRT
<213> ORGANISM: Artificial sequence
<220> FEATURE:
<223> OTHER INFORMATION: E11 ScFv VL CDR1

<400> SEQUENCE: 24

Gly Ser Asn Ser Asn Ile Gly Ser Asn Thr Val Asn
1               5                   10

<210> SEQ ID NO 25
<211> LENGTH: 13
<212> TYPE: PRT
<213> ORGANISM: Artificial sequence
<220> FEATURE:
<223> OTHER INFORMATION: F10 ScFv VL CDR1

<400> SEQUENCE: 25

Ser Gly Ser Thr Ser Asn Ile Ala Ala Asn Thr Val His
1               5                   10

<210> SEQ ID NO 26
<211> LENGTH: 12
<212> TYPE: PRT
<213> ORGANISM: Artificial sequence
<220> FEATURE:
<223> OTHER INFORMATION: B7 ScFv VL CDR1

<400> SEQUENCE: 26

Gly Ser Ser Ser Asn Ile Gly Ser Asn Thr Val Asn
1               5                   10

<210> SEQ ID NO 27
<211> LENGTH: 12
<212> TYPE: PRT
<213> ORGANISM: Artificial sequence
<220> FEATURE:
<223> OTHER INFORMATION: D3 ScFv VL CDR1

<400> SEQUENCE: 27

Arg Ala Ser Gln Ser Val Arg Ser Asn Tyr Leu Ala
1               5                   10

<210> SEQ ID NO 28
<211> LENGTH: 12
<212> TYPE: PRT
<213> ORGANISM: Artificial sequence
<220> FEATURE:
<223> OTHER INFORMATION: E1 ScFv VL CDR1

<400> SEQUENCE: 28

Gly Ser Ser Pro Asn Ile Gly Ser Asn Thr Val Lys
1               5                   10

<210> SEQ ID NO 29
<211> LENGTH: 12
<212> TYPE: PRT
<213> ORGANISM: Artificial sequence
<220> FEATURE:
<223> OTHER INFORMATION: F1 ScFv VL CDR1

<400> SEQUENCE: 29

```
Gly Ser Ser Asn Ile Gly Ser Asn Thr Val Asn
1               5                   10

<210> SEQ ID NO 30
<211> LENGTH: 11
<212> TYPE: PRT
<213> ORGANISM: Artificial sequence
<220> FEATURE:
<223> OTHER INFORMATION: EB ScFv VL CDR1

<400> SEQUENCE: 30

Gln Gly Asp Ser Leu Arg Ser Tyr Tyr Ala Ser
1               5                   10

<210> SEQ ID NO 31
<211> LENGTH: 10
<212> TYPE: PRT
<213> ORGANISM: Artificial sequence
<220> FEATURE:
<223> OTHER INFORMATION: A3 ScFv VL CDR2

<400> SEQUENCE: 31

Asp Ala Ser Ile Arg Ala Thr Gly Ile Pro
1               5                   10

<210> SEQ ID NO 32
<211> LENGTH: 10
<212> TYPE: PRT
<213> ORGANISM: Artificial sequence
<220> FEATURE:
<223> OTHER INFORMATION: C7 ScFv VL CDR2

<400> SEQUENCE: 32

Gly Ala Ser Thr Arg Ala Thr Gly Ile Pro
1               5                   10

<210> SEQ ID NO 33
<211> LENGTH: 10
<212> TYPE: PRT
<213> ORGANISM: Artificial sequence
<220> FEATURE:
<223> OTHER INFORMATION: 11 ScFv VL CDR2

<400> SEQUENCE: 33

Asp Ala Ser Ser Arg Ala Pro Gly Ile Pro
1               5                   10

<210> SEQ ID NO 34
<211> LENGTH: 7
<212> TYPE: PRT
<213> ORGANISM: Artificial sequence
<220> FEATURE:
<223> OTHER INFORMATION: E11 ScFv VL CDR2

<400> SEQUENCE: 34

Gly Val Thr Asn Arg Pro Ser
1               5

<210> SEQ ID NO 35
<211> LENGTH: 7
<212> TYPE: PRT
<213> ORGANISM: Artificial sequence
<220> FEATURE:
<223> OTHER INFORMATION: F10 ScFv VL CDR2

<400> SEQUENCE: 35

Ser Asn Asn Gln Arg Pro Ser
```

```
<210> SEQ ID NO 36
<211> LENGTH: 7
<212> TYPE: PRT
<213> ORGANISM: Artificial sequence
<220> FEATURE:
<223> OTHER INFORMATION: B7 ScFv VL CDR2

<400> SEQUENCE: 36

Arg Asp Asn Gln Arg Pro Ser
1               5

<210> SEQ ID NO 37
<211> LENGTH: 10
<212> TYPE: PRT
<213> ORGANISM: Artificial sequence
<220> FEATURE:
<223> OTHER INFORMATION: D3 ScFv VL CDR2

<400> SEQUENCE: 37

Asp Ala Ser Lys Arg Ala Pro Gly Ile Pro
1               5                   10

<210> SEQ ID NO 38
<211> LENGTH: 7
<212> TYPE: PRT
<213> ORGANISM: Artificial sequence
<220> FEATURE:
<223> OTHER INFORMATION: E1 ScFv VL CDR2

<400> SEQUENCE: 38

Asp Asn Asn Gln Arg Pro Ser
1               5

<210> SEQ ID NO 39
<211> LENGTH: 11
<212> TYPE: PRT
<213> ORGANISM: Artificial sequence
<220> FEATURE:
<223> OTHER INFORMATION: F1 ScFv VL CDR2

<400> SEQUENCE: 39

Asp Asn Tyr Lys Arg Pro Ser Gly Val Pro Asp
1               5                   10

<210> SEQ ID NO 40
<211> LENGTH: 6
<212> TYPE: PRT
<213> ORGANISM: Artificial sequence
<220> FEATURE:
<223> OTHER INFORMATION: EB ScFv VL CDR2

<400> SEQUENCE: 40

Gly Lys Asn Asn Arg Pro
1               5

<210> SEQ ID NO 41
<211> LENGTH: 7
<212> TYPE: PRT
<213> ORGANISM: Artificial sequence
<220> FEATURE:
<223> OTHER INFORMATION: A3 ScFv VH CDR1

<400> SEQUENCE: 41

Leu Ser Ser Tyr Asp Leu Ser
1               5
```

```
<210> SEQ ID NO 42
<211> LENGTH: 9
<212> TYPE: PRT
<213> ORGANISM: Artificial sequence
<220> FEATURE:
<223> OTHER INFORMATION: C7 ScFv VH CDR1

<400> SEQUENCE: 42

Phe Thr Val Asn Ser Asn Tyr Met Asn
1               5

<210> SEQ ID NO 43
<211> LENGTH: 9
<212> TYPE: PRT
<213> ORGANISM: Artificial sequence
<220> FEATURE:
<223> OTHER INFORMATION: D11 ScFv VH CDR1

<400> SEQUENCE: 43

Arg Gln Ala Pro Gly Lys Gly Leu Glu
1               5

<210> SEQ ID NO 44
<211> LENGTH: 8
<212> TYPE: PRT
<213> ORGANISM: Artificial sequence
<220> FEATURE:
<223> OTHER INFORMATION: E11 ScFv VH CDR1

<400> SEQUENCE: 44

Thr Ser Asp Asp His Ala Met His
1               5

<210> SEQ ID NO 45
<211> LENGTH: 6
<212> TYPE: PRT
<213> ORGANISM: Artificial sequence
<220> FEATURE:
<223> OTHER INFORMATION: F10 ScFv VH CDR1

<400> SEQUENCE: 45

Asp Asp Tyr Ala Met Ser
1               5

<210> SEQ ID NO 46
<211> LENGTH: 6
<212> TYPE: PRT
<213> ORGANISM: Artificial sequence
<220> FEATURE:
<223> OTHER INFORMATION: B7 ScFv VH CDR1

<400> SEQUENCE: 46

Arg Arg Tyr Gly Met His
1               5

<210> SEQ ID NO 47
<211> LENGTH: 9
<212> TYPE: PRT
<213> ORGANISM: Artificial sequence
<220> FEATURE:
<223> OTHER INFORMATION: D3 ScFv VH CDR1

<400> SEQUENCE: 47

Arg Gln Ala Pro Gly Lys Gly Leu Glu
1               5

<210> SEQ ID NO 48
```

```
<211> LENGTH: 6
<212> TYPE: PRT
<213> ORGANISM: Artificial sequence
<220> FEATURE:
<223> OTHER INFORMATION: E1 ScFv VH CDR1

<400> SEQUENCE: 48

Thr Asp Tyr Tyr Met Ser
1               5

<210> SEQ ID NO 49
<211> LENGTH: 6
<212> TYPE: PRT
<213> ORGANISM: Artificial sequence
<220> FEATURE:
<223> OTHER INFORMATION: F1 ScFv VH CDR1

<400> SEQUENCE: 49

Ser Ser Ser Ala Leu Gln
1               5

<210> SEQ ID NO 50
<211> LENGTH: 6
<212> TYPE: PRT
<213> ORGANISM: Artificial sequence
<220> FEATURE:
<223> OTHER INFORMATION: EB ScFv VH CDR1

<400> SEQUENCE: 50

Asp Asp Tyr Gly Met Ser
1               5

<210> SEQ ID NO 51
<211> LENGTH: 17
<212> TYPE: PRT
<213> ORGANISM: Artificial sequence
<220> FEATURE:
<223> OTHER INFORMATION: A3 ScFv VH CDR2

<400> SEQUENCE: 51

Arg Ile Asn Gly Asp Gly Ser Ser Thr Ser Tyr Ala Asp Ser Val Lys
1               5                   10                  15

Gly

<210> SEQ ID NO 52
<211> LENGTH: 15
<212> TYPE: PRT
<213> ORGANISM: Artificial sequence
<220> FEATURE:
<223> OTHER INFORMATION: C7 ScFv VH CDR2

<400> SEQUENCE: 52

Ile Glu Thr Asn Gly Ile Thr Ser Tyr Ala Asp Ser Val Lys Gly
1               5                   10                  15

<210> SEQ ID NO 53
<211> LENGTH: 17
<212> TYPE: PRT
<213> ORGANISM: Artificial sequence
<220> FEATURE:
<223> OTHER INFORMATION: D11 ScFv VH CDR2

<400> SEQUENCE: 53

Ala Ile Ser Ala Gly Gly Asp Ala Pro Trp Tyr Ala Gly Ser Ala Arg
1               5                   10                  15

Gly
```

```
<210> SEQ ID NO 54
<211> LENGTH: 17
<212> TYPE: PRT
<213> ORGANISM: Artificial sequence
<220> FEATURE:
<223> OTHER INFORMATION: E11 ScFv VH CDR2

<400> SEQUENCE: 54

Arg Ile Asn Ser Asp Gly Ser Ser Thr Ile Tyr Ala Asp Ser Ala Lys
 1               5                  10                  15
Gly

<210> SEQ ID NO 55
<211> LENGTH: 17
<212> TYPE: PRT
<213> ORGANISM: Artificial sequence
<220> FEATURE:
<223> OTHER INFORMATION: F10 ScFv VH CDR2

<400> SEQUENCE: 55

Ala Ile Ser Gly Ser Gly Gly Thr Thr Tyr Tyr Ala Asp Ser Val Lys
 1               5                  10                  15
Gly

<210> SEQ ID NO 56
<211> LENGTH: 17
<212> TYPE: PRT
<213> ORGANISM: Artificial sequence
<220> FEATURE:
<223> OTHER INFORMATION: B7 ScFv VH CDR2

<400> SEQUENCE: 56

Ala Ile Thr Thr Gly Gly Gly Ser Pro Asn Tyr Ala Asp Ser Val Lys
 1               5                  10                  15
Gly

<210> SEQ ID NO 57
<211> LENGTH: 17
<212> TYPE: PRT
<213> ORGANISM: Artificial sequence
<220> FEATURE:
<223> OTHER INFORMATION: D3 ScFv VH CDR2

<400> SEQUENCE: 57

Gly Ile Ser Gly Ser Gly Gly Ser Thr Asn Tyr Ala Asp Ser Val Lys
 1               5                  10                  15
Gly

<210> SEQ ID NO 58
<211> LENGTH: 17
<212> TYPE: PRT
<213> ORGANISM: Artificial sequence
<220> FEATURE:
<223> OTHER INFORMATION: E1 ScFv VH CDR2

<400> SEQUENCE: 58

Tyr Ile Asn Pro Ser Ser Arg Tyr Thr Asp Tyr Ala Asp Ser Val Lys
 1               5                  10                  15
Gly

<210> SEQ ID NO 59
<211> LENGTH: 17
<212> TYPE: PRT
<213> ORGANISM: Artificial sequence
```

```
<220> FEATURE:
<223> OTHER INFORMATION: F1 ScFv VH CDR2

<400> SEQUENCE: 59

Tyr Val Ser Pro Gly Ser Asp Asp Thr Tyr Tyr Ala Asp Ser Val Lys
1               5                   10                  15

Gly

<210> SEQ ID NO 60
<211> LENGTH: 17
<212> TYPE: PRT
<213> ORGANISM: Artificial sequence
<220> FEATURE:
<223> OTHER INFORMATION: EB ScFv VH CDR2

<400> SEQUENCE: 60

Gly Ile Asn Trp Asn Gly Gly Ser Thr Gly Tyr Ala Asp Ser Val Lys
1               5                   10                  15

Gly

<210> SEQ ID NO 61
<211> LENGTH: 13
<212> TYPE: PRT
<213> ORGANISM: Artificial sequence
<220> FEATURE:
<223> OTHER INFORMATION: Phage displayed peptide

<400> SEQUENCE: 61

Gly Gly Gly Ser Ser Ser Thr Ser His Phe Ser His Ser
1               5                   10

<210> SEQ ID NO 62
<211> LENGTH: 13
<212> TYPE: PRT
<213> ORGANISM: Artificial sequence
<220> FEATURE:
<223> OTHER INFORMATION: Phage displayed peptide

<400> SEQUENCE: 62

Gly Gly Gly Met Gln Thr Tyr Thr Asn Ser Ser His Ser
1               5                   10

<210> SEQ ID NO 63
<211> LENGTH: 13
<212> TYPE: PRT
<213> ORGANISM: Artificial sequence
<220> FEATURE:
<223> OTHER INFORMATION: Phage displayed peptide

<400> SEQUENCE: 63

Gly Gly Gly Arg Ser Val Gln Leu Thr Leu Ser His Ser
1               5                   10

<210> SEQ ID NO 64
<211> LENGTH: 13
<212> TYPE: PRT
<213> ORGANISM: Artificial sequence
<220> FEATURE:
<223> OTHER INFORMATION: Phage displayed peptide

<400> SEQUENCE: 64

Gly Gly Gly Ser Arg Ala Gln Thr Tyr Ala Ser His Ser
1               5                   10

<210> SEQ ID NO 65
<211> LENGTH: 13
```

```
<212> TYPE: PRT
<213> ORGANISM: Artificial sequence
<220> FEATURE:
<223> OTHER INFORMATION: Phage displayed peptide

<400> SEQUENCE: 65

Gly Gly Gly Pro Ser Glu Ala Leu His Trp Ser His Ser
1               5                   10

<210> SEQ ID NO 66
<211> LENGTH: 13
<212> TYPE: PRT
<213> ORGANISM: Artificial sequence
<220> FEATURE:
<223> OTHER INFORMATION: Phage displayed peptide

<400> SEQUENCE: 66

Gly Gly Gly Phe Leu Gln Ser Thr Ile His Ser His Ser
1               5                   10

<210> SEQ ID NO 67
<211> LENGTH: 13
<212> TYPE: PRT
<213> ORGANISM: Artificial sequence
<220> FEATURE:
<223> OTHER INFORMATION: Phage displayed peptide

<400> SEQUENCE: 67

Gly Gly Gly Arg Leu Asn His Glu His Ser Ser His Ser
1               5                   10

<210> SEQ ID NO 68
<211> LENGTH: 13
<212> TYPE: PRT
<213> ORGANISM: Artificial sequence
<220> FEATURE:
<223> OTHER INFORMATION: Phage displayed peptide

<400> SEQUENCE: 68

Gly Gly Gly Ser Arg Lys Leu Pro Met Tyr Ser His Ser
1               5                   10

<210> SEQ ID NO 69
<211> LENGTH: 13
<212> TYPE: PRT
<213> ORGANISM: Artificial sequence
<220> FEATURE:
<223> OTHER INFORMATION: Phage displayed peptide

<400> SEQUENCE: 69

Gly Gly Gly Ser Arg Lys Leu Pro Met Tyr Ser His Ser
1               5                   10

<210> SEQ ID NO 70
<211> LENGTH: 13
<212> TYPE: PRT
<213> ORGANISM: Artificial sequence
<220> FEATURE:
<223> OTHER INFORMATION: Phage displayed peptide

<400> SEQUENCE: 70

Gly Gly Gly Asp Pro Trp Glu Ile Thr Thr Ser His Ser
1               5                   10

<210> SEQ ID NO 71
<211> LENGTH: 13
<212> TYPE: PRT
<213> ORGANISM: Artificial sequence
```

```
<220> FEATURE:
<223> OTHER INFORMATION: Phage displayed peptide

<400> SEQUENCE: 71

Gly Gly Gly Leu Leu Thr Thr Thr Thr Gly Ser His Ser
1               5                   10

<210> SEQ ID NO 72
<211> LENGTH: 13
<212> TYPE: PRT
<213> ORGANISM: Artificial sequence
<220> FEATURE:
<223> OTHER INFORMATION: Phage displayed peptide

<400> SEQUENCE: 72

Gly Gly Gly Leu Pro Pro Pro Thr Tyr Thr Ser His Ser
1               5                   10

<210> SEQ ID NO 73
<211> LENGTH: 13
<212> TYPE: PRT
<213> ORGANISM: Artificial sequence
<220> FEATURE:
<223> OTHER INFORMATION: Phage displayed peptide

<400> SEQUENCE: 73

Gly Gly Gly Asp Ser Ile Pro Ser His Val Ser His Ser
1               5                   10

<210> SEQ ID NO 74
<211> LENGTH: 13
<212> TYPE: PRT
<213> ORGANISM: Artificial sequence
<220> FEATURE:
<223> OTHER INFORMATION: Phage displayed peptide

<400> SEQUENCE: 74

Gly Gly Gly Pro Ser Ser Glu Tyr Gln Trp Ser His Ser
1               5                   10

<210> SEQ ID NO 75
<211> LENGTH: 7
<212> TYPE: PRT
<213> ORGANISM: Artificial sequence
<220> FEATURE:
<223> OTHER INFORMATION: Phage displayed peptide

<400> SEQUENCE: 75

Val Ser Leu Pro Ser Val Ala
1               5

<210> SEQ ID NO 76
<211> LENGTH: 13
<212> TYPE: PRT
<213> ORGANISM: Artificial sequence
<220> FEATURE:
<223> OTHER INFORMATION: Phage displayed peptide

<400> SEQUENCE: 76

Gly Gly Gly Thr Ile Ile Thr His His Gln Ser His Ser
1               5                   10

<210> SEQ ID NO 77
<211> LENGTH: 13
<212> TYPE: PRT
<213> ORGANISM: Artificial sequence
<220> FEATURE:
<223> OTHER INFORMATION: Phage displayed peptide
```

<400> SEQUENCE: 77

Gly Gly Gly Thr Ile Ile Thr His His Gln Ser His Ser
1               5                   10

<210> SEQ ID NO 78
<211> LENGTH: 13
<212> TYPE: PRT
<213> ORGANISM: Artificial sequence
<220> FEATURE:
<223> OTHER INFORMATION: Phage displayed peptide

<400> SEQUENCE: 78

Gly Gly Gly Thr Ile Ile Thr His His Gln Ser His Ser
1               5                   10

<210> SEQ ID NO 79
<211> LENGTH: 13
<212> TYPE: PRT
<213> ORGANISM: Artificial sequence
<220> FEATURE:
<223> OTHER INFORMATION: Phage displayed peptide

<400> SEQUENCE: 79

Gly Gly Gly Ile Pro Trp Ser His Pro Asp Ser His Ser
1               5                   10

<210> SEQ ID NO 80
<211> LENGTH: 13
<212> TYPE: PRT
<213> ORGANISM: Artificial sequence
<220> FEATURE:
<223> OTHER INFORMATION: Phage displayed peptide

<400> SEQUENCE: 80

Gly Gly Gly Ile Pro Trp Ser His Pro Asp Ser His Ser
1               5                   10

<210> SEQ ID NO 81
<211> LENGTH: 13
<212> TYPE: PRT
<213> ORGANISM: Artificial sequence
<220> FEATURE:
<223> OTHER INFORMATION: Phage displayed peptide

<400> SEQUENCE: 81

Gly Gly Gly Pro Leu His Arg Pro Thr His Ser His Ser
1               5                   10

<210> SEQ ID NO 82
<211> LENGTH: 13
<212> TYPE: PRT
<213> ORGANISM: Artificial sequence
<220> FEATURE:
<223> OTHER INFORMATION: Phage displayed peptide

<400> SEQUENCE: 82

Gly Gly Gly Thr Ala Trp Leu Pro Thr Trp Ser His Ser
1               5                   10

<210> SEQ ID NO 83
<211> LENGTH: 13
<212> TYPE: PRT
<213> ORGANISM: Artificial sequence
<220> FEATURE:
<223> OTHER INFORMATION: Phage displayed peptide

<400> SEQUENCE: 83

Gly Gly Gly Arg Gln Leu Glu Leu Gln Ala Ser His Ser
1               5                   10

<210> SEQ ID NO 84
<211> LENGTH: 13
<212> TYPE: PRT
<213> ORGANISM: Artificial sequence
<220> FEATURE:
<223> OTHER INFORMATION: Phage displayed peptide

<400> SEQUENCE: 84

Gly Gly Gly Arg Phe Asp His Gln Ala Thr Ser His Ser
1               5                   10

<210> SEQ ID NO 85
<211> LENGTH: 13
<212> TYPE: PRT
<213> ORGANISM: Artificial sequence
<220> FEATURE:
<223> OTHER INFORMATION: Phage displayed peptide

<400> SEQUENCE: 85

Gly Gly Gly Ala Met Pro Gln Arg Pro Leu Ser His Ser
1               5                   10

<210> SEQ ID NO 86
<211> LENGTH: 13
<212> TYPE: PRT
<213> ORGANISM: Artificial sequence
<220> FEATURE:
<223> OTHER INFORMATION: Phage displayed peptide

<400> SEQUENCE: 86

Gly Gly Gly Tyr Thr Tyr Met Ala Pro Leu Ser His Ser
1               5                   10

<210> SEQ ID NO 87
<211> LENGTH: 6
<212> TYPE: PRT
<213> ORGANISM: Artificial sequence
<220> FEATURE:
<223> OTHER INFORMATION: SR scFv VL CDR1

<400> SEQUENCE: 87

Ser Ser Tyr Val Leu His
1               5

<210> SEQ ID NO 88
<211> LENGTH: 17
<212> TYPE: PRT
<213> ORGANISM: Artificial sequence
<220> FEATURE:
<223> OTHER INFORMATION: SR scFv VL CDR2

<400> SEQUENCE: 88

Gly Ile Ser Gly Ser Gly Ala Thr Ala Tyr Tyr Ala Asp Ser Val Lys
1               5                   10                  15

Gly

<210> SEQ ID NO 89
<211> LENGTH: 9
<212> TYPE: PRT
<213> ORGANISM: Artificial sequence
<220> FEATURE:
<223> OTHER INFORMATION: SR scFv VL CDR3

<400> SEQUENCE: 89

Asn Asp Gly Gly Gly Leu Leu Asp Phe
1               5

<210> SEQ ID NO 90
<211> LENGTH: 12
<212> TYPE: PRT
<213> ORGANISM: Artificial sequence
<220> FEATURE:
<223> OTHER INFORMATION: SR scFv VH CDR1

<400> SEQUENCE: 90

Gly Ser Asn Ser Asn Ile Gly Asn Asn Ser Val Asn
1               5                   10

<210> SEQ ID NO 91
<211> LENGTH: 7
<212> TYPE: PRT
<213> ORGANISM: Artificial sequence
<220> FEATURE:
<223> OTHER INFORMATION: SR scFv VH CDR2

<400> SEQUENCE: 91

Arg Asn Thr Asn Arg Pro Ser
1               5

<210> SEQ ID NO 92
<211> LENGTH: 11
<212> TYPE: PRT
<213> ORGANISM: Artificial sequence
<220> FEATURE:
<223> OTHER INFORMATION: SR scFv VH CDR3

<400> SEQUENCE: 92

Ser Ser Tyr Ala Ser Asn Arg Asp Val Leu Phe
1               5                   10

<210> SEQ ID NO 93
<211> LENGTH: 6
<212> TYPE: PRT
<213> ORGANISM: Artificial sequence
<220> FEATURE:
<223> OTHER INFORMATION: B7 scFv VH CDR1

<400> SEQUENCE: 93

Arg Arg Tyr Gly Met His
1               5

<210> SEQ ID NO 94
<211> LENGTH: 18
<212> TYPE: PRT
<213> ORGANISM: Artificial sequence
<220> FEATURE:
<223> OTHER INFORMATION: B7 scFv VH CDR2

<400> SEQUENCE: 94

Ala Ile Thr Thr Gly Gly Gly Ser Pro Asn Tyr Ala Asp Ser Val Lys
1               5                   10                  15

Gly Arg

<210> SEQ ID NO 95
<211> LENGTH: 9
<212> TYPE: PRT
<213> ORGANISM: Artificial sequence
<220> FEATURE:
<223> OTHER INFORMATION: B7 scFv VH CDR3

<400> SEQUENCE: 95

Asp Arg Thr Ala Gly Tyr Phe Asp Tyr
1               5

<210> SEQ ID NO 96
<211> LENGTH: 12
<212> TYPE: PRT
<213> ORGANISM: Artificial sequence
<220> FEATURE:
<223> OTHER INFORMATION: B7 scFv VL CDR1

<400> SEQUENCE: 96

Gly Ser Ser Ser Asn Ile Gly Ser Asn Thr Val Asn
1               5                   10

<210> SEQ ID NO 97
<211> LENGTH: 7
<212> TYPE: PRT
<213> ORGANISM: Artificial sequence
<220> FEATURE:
<223> OTHER INFORMATION: B7 scFv VL CDR2

<400> SEQUENCE: 97

Arg Asp Asn Gln Arg Pro Ser
1               5

<210> SEQ ID NO 98
<211> LENGTH: 14
<212> TYPE: PRT
<213> ORGANISM: Artificial sequence
<220> FEATURE:
<223> OTHER INFORMATION: B7 scFv VL CDR3

<400> SEQUENCE: 98

Asn Ser Arg Asp Ser Ser Gly Asn Arg Val Val Phe Gly Gly
1               5                   10

<210> SEQ ID NO 99
<211> LENGTH: 7
<212> TYPE: PRT
<213> ORGANISM: Artificial sequence
<220> FEATURE:
<223> OTHER INFORMATION: 12A scFv VL CDR1

<400> SEQUENCE: 99

Thr Thr Tyr Asn Met Asn Trp
1               5

<210> SEQ ID NO 100
<211> LENGTH: 17
<212> TYPE: PRT
<213> ORGANISM: Artificial sequence
<220> FEATURE:
<223> OTHER INFORMATION: 12A scFv VL CDR2

<400> SEQUENCE: 100

Arg Ile Asn Thr Asp Gly Ser Asn Thr Gly Tyr Ala Asp Ser Val Lys
1               5                   10                  15
Gly

<210> SEQ ID NO 101
<211> LENGTH: 16
<212> TYPE: PRT
<213> ORGANISM: Artificial sequence
<220> FEATURE:
<223> OTHER INFORMATION: 12A scFv VL CDR3

<400> SEQUENCE: 101

-continued

```
Asp Phe Phe Gly Arg Arg Gly Ala Tyr Phe Tyr Ser Gly Met Asp Val
1               5                   10                  15

<210> SEQ ID NO 102
<211> LENGTH: 7
<212> TYPE: PRT
<213> ORGANISM: Artificial sequence
<220> FEATURE:
<223> OTHER INFORMATION: 12A scFv VH CDR1

<400> SEQUENCE: 102

Asn Val Asn Ser Asn Leu Ala
1               5

<210> SEQ ID NO 103
<211> LENGTH: 10
<212> TYPE: PRT
<213> ORGANISM: Artificial sequence
<220> FEATURE:
<223> OTHER INFORMATION: 12A scFv VH CDR2

<400> SEQUENCE: 103

Gly Ala Ser Ser Arg Ala Thr Gly Ile Pro
1               5                   10

<210> SEQ ID NO 104
<211> LENGTH: 8
<212> TYPE: PRT
<213> ORGANISM: Artificial sequence
<220> FEATURE:
<223> OTHER INFORMATION: 12A scFv VH CDR3

<400> SEQUENCE: 104

Gln His Arg Gly Thr Phe Gly Gly
1               5
```